United States Patent
Horowitz et al.

(10) Patent No.: US 11,752,197 B2
(45) Date of Patent: Sep. 12, 2023

(54) MACROPHAGE STIMULATING 1 RECEPTOR (MST1R) VARIANTS AND USES THEREOF

(71) Applicant: Regeneron Pharmaceuticals, Inc., Tarrytown, NY (US)

(72) Inventors: Julie Horowitz, Tarrytown, NY (US); Aris Baras, Tarrytown, NY (US); Manuel Allen Revez Ferreira, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 103 days.

(21) Appl. No.: 16/990,744

(22) Filed: Aug. 11, 2020

(65) Prior Publication Data

US 2021/0046157 A1     Feb. 18, 2021

Related U.S. Application Data

(60) Provisional application No. 62/885,402, filed on Aug. 12, 2019.

(51) Int. Cl.

| | | |
|---|---|---|
| *A61K 38/18* | (2006.01) | |
| *A61K 38/17* | (2006.01) | |
| *A61P 1/00* | (2006.01) | |
| *A61K 31/12* | (2006.01) | |
| *A61K 31/4741* | (2006.01) | |
| *A61K 38/48* | (2006.01) | |
| *C07K 16/22* | (2006.01) | |
| *C07K 16/28* | (2006.01) | |
| *C12Q 1/6883* | (2018.01) | |
| *G01N 33/68* | (2006.01) | |
| *G01N 33/48* | (2006.01) | |
| *G01N 33/53* | (2006.01) | |
| *C12Q 1/6827* | (2018.01) | |
| *C12Q 1/68* | (2018.01) | |

(52) U.S. Cl.
CPC ............. *A61K 38/18* (2013.01); *A61K 31/12* (2013.01); *A61K 31/4741* (2013.01); *A61K 38/177* (2013.01); *A61K 38/1709* (2013.01); *A61K 38/1796* (2013.01); *A61K 38/482* (2013.01); *A61K 38/4846* (2013.01); *A61K 38/4853* (2013.01); *A61P 1/00* (2018.01); *C07K 16/22* (2013.01); *C07K 16/2863* (2013.01); *C12Q 1/6883* (2013.01); *G01N 33/6893* (2013.01); *C12Q 1/68* (2013.01); *C12Q 1/6827* (2013.01); *C12Q 2600/118* (2013.01); *C12Q 2600/156* (2013.01); *G01N 33/48* (2013.01); *G01N 33/53* (2013.01); *G01N 2333/475* (2013.01); *G01N 2333/71* (2013.01); *G01N 2800/065* (2013.01)

(58) Field of Classification Search
None
See application file for complete search history.

(56) References Cited

U.S. PATENT DOCUMENTS

| | | |
|---|---|---|
| 7,691,997 B2 | 4/2010 | Khvorova et al. |
| 7,838,234 B2 | 11/2010 | Buggy et al. |
| 7,919,084 B2 * | 4/2011 | Breit ............... C07K 16/22 514/1.9 |
| 8,669,091 B2 | 3/2014 | Gentschev et al. |
| 8,725,426 B2 | 5/2014 | Shak et al. |
| 8,933,230 B2 | 1/2015 | Yun et al. |
| 9,006,252 B2 | 4/2015 | Hsieh et al. |
| 9,089,580 B1 | 7/2015 | Garcia et al. |
| 9,103,837 B2 | 8/2015 | Nikrad et al. |
| 9,128,096 B2 | 9/2015 | Buggy et al. |
| 9,186,318 B2 | 11/2015 | Yun et al. |
| 9,353,415 B2 | 5/2016 | Nikolsky et al. |
| 9,403,909 B2 | 8/2016 | Kawaida et al. |
| 9,415,117 B2 | 8/2016 | Howard |
| 9,423,403 B2 | 8/2016 | Nikrad et al. |
| 9,429,565 B2 | 8/2016 | Chenchik et al. |
| 9,433,629 B2 | 9/2016 | Garcia et al. |
| 9,481,668 B2 | 11/2016 | Schadt et al. |
| 9,669,074 B2 | 6/2017 | Garcia et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,889,207 B2 | 2/2018 | Howard |
| 9,919,056 B2 | 3/2018 | Berkel et al. |
| 9,931,414 B2 | 4/2018 | Berkel et al. |
| 9,931,415 B2 | 4/2018 | Berkel et al. |
| 9,950,078 B2 | 4/2018 | Howard et al. |
| 9,956,298 B2 | 5/2018 | Howard et al. |
| 9,956,299 B2 | 5/2018 | Howard et al. |
| 10,010,624 B2 | 7/2018 | Howard et al. |
| 10,029,018 B2 | 7/2018 | Howard et al. |

(Continued)

FOREIGN PATENT DOCUMENTS

| | | |
|---|---|---|
| CN | 102228666 | 11/2011 |
| KR | 20100011620 | 2/2010 |

(Continued)

OTHER PUBLICATIONS

Goyette et al., 2008, Mucosal Immunology 1(2):131-138.*
Feldman, 2002, Molecular Pharmacology. 61(4): 707-709.*
Kempf et al., 2007, Clin. Chem. 53:284-291.*
Kempf et al., 2006, Cir. Res. 98:351-360.*
Xu et al., 2006, Circ. Res. 98:342-350.*
Tobin et al., 2006, Drug Discovery Today 11:405-411.*

(Continued)

*Primary Examiner* — Elizabeth C. Kemmerer
(74) *Attorney, Agent, or Firm* — Armstrong Teasdale LLP

(57) ABSTRACT

Methods of treating patients having inflammatory bowel disease (IBD) or primary sclerosing cholangitis (PSC) are provided herein.

23 Claims, 20 Drawing Sheets

Specification includes a Sequence Listing.

(56) References Cited

U.S. PATENT DOCUMENTS

| | | | |
|---|---|---|---|
| 10,125,114 B2 | 11/2018 | Bradner et al. |
| 10,188,746 B2 | 1/2019 | Howard |
| 10,196,634 B2 | 2/2019 | Chenchik et al. |
| 10,233,503 B2 | 3/2019 | Badosa et al. |
| 10,335,497 B2 | 7/2019 | Howard |
| 10,420,777 B2 | 9/2019 | Howard et al. |
| 10,464,925 B2 | 11/2019 | Bradner et al. |
| 10,473,667 B2 | 11/2019 | Vu et al. |
| 10,543,279 B2 | 1/2020 | Howard et al. |
| 10,607,717 B2 | 3/2020 | Staudt et al. |
| 10,619,210 B2 | 4/2020 | Ahuja et al. |
| 10,646,584 B2 | 5/2020 | Howard |
| 10,669,253 B2 | 6/2020 | Bradner et al. |
| 10,695,433 B2 | 6/2020 | Berkel et al. |
| 10,695,439 B2 | 6/2020 | Howard et al. |
| 10,722,594 B2 | 7/2020 | Howard et al. |
| 10,736,903 B2 | 8/2020 | Berkel et al. |
| 2003/0216306 A1* | 11/2003 | Sabbadini | A61K 38/4853 424/94.64 |
| 2007/0037186 A1 | 2/2007 | Jiang et al. |
| 2008/0255025 A1* | 10/2008 | Ladner | A61P 29/00 506/17 |
| 2009/0208461 A1 | 8/2009 | Hotz et al. |
| 2009/0226442 A1 | 9/2009 | Huet et al. |
| 2011/0320392 A1 | 12/2011 | Black et al. |
| 2012/0040855 A1 | 2/2012 | Pan et al. |
| 2012/0171672 A1* | 7/2012 | Barken | G01N 33/564 435/7.1 |
| 2013/0064901 A1 | 3/2013 | Tan et al. |
| 2013/0089554 A1 | 4/2013 | Blankenship et al. |
| 2013/0095097 A1 | 4/2013 | Blankenship et al. |
| 2013/0129723 A1 | 5/2013 | Blankenship et al. |
| 2014/0137274 A1 | 5/2014 | Ishikawa |
| 2014/0212890 A1 | 7/2014 | Vu et al. |
| 2014/0303002 A1 | 10/2014 | Shak et al. |
| 2015/0259751 A1 | 9/2015 | Uppaluri et al. |
| 2015/0273077 A1 | 10/2015 | Berkel et al. |
| 2015/0274844 A1 | 10/2015 | Blankenship et al. |
| 2015/0283258 A1 | 10/2015 | Berkel et al. |
| 2016/0031887 A1 | 2/2016 | Howard |
| 2016/0160286 A1 | 6/2016 | Buggy et al. |
| 2016/0251718 A1 | 9/2016 | Giudice et al. |
| 2016/0256561 A1 | 9/2016 | Howard et al. |
| 2017/0159128 A1 | 6/2017 | Lazar |
| 2017/0298443 A1 | 10/2017 | Dai et al. |
| 2018/0045727 A1 | 2/2018 | Spetzler et al. |
| 2018/0064821 A1 | 3/2018 | Hemachand et al. |
| 2018/0085465 A1 | 3/2018 | Bradner et al. |
| 2018/0092985 A1 | 4/2018 | Berkel et al. |
| 2018/0153975 A1 | 6/2018 | Fritsch et al. |
| 2018/0193480 A1 | 7/2018 | Berkel et al. |
| 2018/0202004 A1 | 7/2018 | Knudsen |
| 2018/0250417 A1 | 9/2018 | Berkel et al. |
| 2018/0273642 A1 | 9/2018 | Blankenship et al. |
| 2018/0356402 A1 | 12/2018 | Fairchild et al. |
| 2018/0362624 A1 | 12/2018 | Gouilleux-Gruart et al. |
| 2019/0076542 A1 | 3/2019 | Phillips et al. |
| 2019/0085397 A1 | 3/2019 | Fairchild et al. |
| 2019/0151457 A1 | 5/2019 | Bradner et al. |
| 2019/0231795 A1 | 8/2019 | Knudsen et al. |
| 2019/0241633 A1 | 8/2019 | Fotin-Mleczek et al. |
| 2019/0282705 A1 | 9/2019 | Howard et al. |
| 2019/0302117 A1 | 10/2019 | Parker et al. |
| 2019/0307890 A1 | 10/2019 | Howard et al. |
| 2019/0315738 A1 | 10/2019 | Choi et al. |
| 2019/0358295 A1 | 11/2019 | Socolovsky et al. |
| 2020/0081012 A1 | 3/2020 | Vu et al. |
| 2020/0115390 A1 | 4/2020 | Howard et al. |
| 2020/0143906 A1 | 5/2020 | Staudt et al. |
| 2020/0190199 A1 | 6/2020 | Chuang et al. |

FOREIGN PATENT DOCUMENTS

| | | | |
|---|---|---|---|
| WO | WO 00/53232 A1 * | 9/2000 |
| WO | 2011078778 | 6/2011 |
| WO | 2011093675 | 8/2011 |
| WO | 2014057118 | 4/2014 |
| WO | 2014071218 | 5/2014 |
| WO | 2015085351 | 6/2015 |
| WO | 2015087259 | 6/2015 |
| WO | 2015179729 | 11/2015 |
| WO | 2016087625 | 6/2016 |
| WO | 2017137553 | 8/2017 |
| WO | 2017191274 | 11/2017 |
| WO | 2018183928 | 10/2018 |
| WO | 2018227023 | 12/2018 |
| WO | 2019018440 | 1/2019 |
| WO | 2019060917 | 4/2019 |
| WO | 2019068007 | 4/2019 |
| WO | 2019140380 | 7/2019 |
| WO | 2019197602 | 10/2019 |
| WO | 2019232485 | 12/2019 |
| WO | 2020007234 | 1/2020 |
| WO | 2020015615 | 1/2020 |
| WO | 2020018019 | 1/2020 |
| WO | 2020036437 | 2/2020 |
| WO | 2020065406 | 7/2020 |

OTHER PUBLICATIONS

Lajer et al., 2010, Diabetes Care 33:1567-1572.*
Database WPI, Week 201230, Thompson Scientific, XP002800521.
Database WPI, Week 201050, Thompson Scientific, XP002800522.
Annex to Invitation to Pay Additional Fees dated Oct. 9, 2020 in International Patent Application No. PCT/US2020/045784.
Ma, "The Role Research of Rat Pancreatic Beta Cells of Lipid Toxicity Injury under GPR119/MST1/FoxO1 Pathway" Abstract China Excellent Master's Dissertation, Medicine and Health Science and Technology Series, 2018, Issue 09, pp. 1-4.
Zhou et al., "Curcumin Modulated Macrophage Polarization Through the Inhibition of the Toll-Like Receptor 4 Expression and its Signaling Pathways", Cell Physiol Biochem, 2015, 36, pp. 631-641.

* cited by examiner

A.

B.

B.

C.

EC: enterocytes
GB: goblet cell
Pro: progenitor cell
Pro_P: Paneth progenitor cell
TA: transit amplifying cell 1998 (20%) out of 10,000 cells expressed MST1

| Phenotype | Gene | Rare Variant Burden | Cases RR:RA:AA | Controls RR:RA:AA | AAF | OR (95% CI) | P-value |
|---|---|---|---|---|---|---|---|
| IBD Meta Analysis | MST1R | Predicted loss-of-function variants | 8,191:64:0 | 216,239:999:1 | 0.0024 | 2.10 (1.41, 3.13) | 2.60E-04 |
| Crohn's Meta Analysis | MST1R | Predicted loss-of-function variants | 5,554:49:0 | 189,207:831:1 | 0.0023 | 3.12 (1.94, 5.04) | 3.10E-06 |
| UC Meta Analysis | MST1R | Predicted loss-of-function variants | 2,890:18:0 | 189,089:831:1 | 0.0022 | 1.56 (0.95, 2.59) | 8.20E-02 |
| PSC Meta Analysis | MST1R | Predicted loss-of-function variants | 1,863:19:0 | 4,914:8:0 | 0.0020 | 5.59 (2.05, 15.27) | 7.90E-04 |

Figure 10

SEQUENCE LISTING

```
<160> NUMBER OF SEQ ID NOS: 40

<210> SEQ ID NO 1
<211> LENGTH: 16636
<212> TYPE: DNA
<213> ORGANISM: homo sapien

<400> SEQUENCE: 1
ggatcctcta gggtcccagc tcgcctcgat ggagctcctc ccgccgctgc ctcagtcctt      60
cctgttgctg ctgctgttgc ctgccaagcc cgcggcgggc gaggactggc agtgcccgcg     120
caccccctac gcggcctctc gcgactttga cgtgaagtac gtggtgccca gcttctccgc     180
cggaggcctg gtacaggcca tggtgaccta cgagggcgac agaaatgaga gtgctgtgtt     240
tgtagccata cgcaatcgcc tgcatgtgct tgggcctgac ctgaagtctg tccagagcct     300
ggccacgggc cctgctggag accctggctg ccagacgtgt gcagcctgtg gcccaggacc     360
ccacggccct cccggtgaca cagacacaaa ggtgctggtg ctggatcccg cgctgcctgc     420
gctggtcagt tgtggctcca gcctgcaggg ccgctgcttc ctgcatgacc tagagcccca     480
agggacagcc gtgcatctgg cagcgccagc ctgcctcttc tcagcccacc ataaccggcc     540
cgatgactgc cccgactgtg tggccagccc attgggcacc cgtgtaactg tggttgagca     600
aggccaggcc tcctatttct acgtggcatc ctcactggac gcagccgtgg ctgccagctt     660
cagcccacgc tcagtgtcta tcaggcgtct caaggctgac gcctcgggat tcgcaccggg     720
ctttgtggcg ttgtcagtgc tgcccaagca tcttgtctcc tacagtattg aatacgtgca     780
```

```
cagcttccac acgggagcct tcgtatactt cctgactgta cagccggcca gcgtgacaga      840
tgatcctagt gccctgcaca cacgcctggc acggcttagc gccactgagc cagagttggg      900
tgactatcgg gagctggtcc tcgactgcag atttgctcca aaacgcaggc gccgggggc      960 cccagaaggc ggacagccct accctgtgct gcgggtggcc cactccgctc cagtgggtgc     1020
ccaacttgcc actgagctga gcatcgccga gggccaggaa gtactatttg gggtctttgt     1080
gactggcaag gatggtggtc ctggcgtggg ccccaactct gtcgtctgtg ccttccccat     1140
tgacctgctg gacacactaa ttgatgaggg tgtggagcgc tgttgtgaat ccccagtcca     1200
tccaggcctc cggcgaggcc tcgacttctt ccagtcgccc agttttttgcc caacccggt     1260 aagctgaaag aagggcccct tacttgtgag ctgcatgcac atggctgaac acaggctgct     1320
tcccttccat cactgagggg atctgggggc gcggtgggg ggcaggcgga aagaagcatt     1380
ctctctcacc cagttcctaa gtgctggggt ggtgtgagaa accagccaga caaaggctac     1440
actggaggct tagctcccag gctggccctt gtggctgcct catcttgctc tttcccctac     1500
ctgcccatca tggcctctgg ttttttaggt agtttccctg gctatgtgag gatagggtta     1560
cataaccgtg tctctgttag catagctcct gaatgctggg tagaatgatg ggcattccct     1620
cctacttgtc caccacccat atcctcaggg acacacgcag aaaaatagca ctcccccctc     1680 ccctcccca ccccgccac caccaccacc accacgcaca aatacacagg gagatgctca     1740
cagattcaca gactcacagc tgcttgccaa cagtttcact ttcccttgtt ttgctctgct     1800
ttccaaaggg ggtgggacgg gagttgtcag agaatctccc cttcctccac acccctccc     1860 cccacccacc cccatccttc tgccagccac cacgttccag ggagcctcct gggccttgga     1920
agttgggagc ttgttaggga gcctgcatgt cctgggcttc actaacgttt ttgccatgat     1980
tgggggtgat tgggggagta cccagaactc atggaatggc agcttggttc tagaaggttc     2040
tgggagcctc actctagtct tgtgcaagca actataaaca tctggggata agtaaaggcc     2100
taggaagggc tggttggaat tggtccatcc cagacttttt ttttttaactg tatttggagc     2160 cctaccccag gcaggaagtc tcaaagcctg tgctgaactg ggggctcctt ccacagactc     2220
tatctaggtt ctctccagcc atcgtgtagg caacagcagt aagattggac caaggaatgg     2280
gacccacagc tactgttctt agattctcta gctatcatcc tgtggccctg gcctgctgt     2340 gacattctcg aaagactcct ttccgctcct attgatgcct cggagatggg agaacttaca     2400
cccaatgtga ggttgggggt ctttagcctc cctccctctg ctgagtacat ctgggttgag     2460
aggccctagg gttggggact ccttgtctgg gcctgggcag gcctgcctgg ccccttctcc     2520
ttcccaatgg ggagtcagaa cctctcccca gcttgcctag tggtcagtgg gtcagaagac     2580
acccagcacg gctgggcagt gccaggctcc aggaagacta atcttggtcc ctgctcacag     2640
gctggccagg ccccaggag gtgtgtgaat caccccgtgc agtgtttgcc cagcaactct     2700
gggcatgcag ccactagggc agcacccaca tagtggttgg cctcaggagg cctgagggac     2760
tcagagctgg tgcctgtcct ccatgggaca ttggacactt acgtgttttc aggagctggg     2820
ggcccctacc taagcctggg aacgtagagc taaggtcctg gggctaggga caagcaggct     2880
agggtgtggg cctgactaag gtagggctct attccccttc agagcccac ctgtccctga     2940 gtcatgctag aaacacctgg cagccttccg gctcgggcca agccaagccg atttcctgcc     3000
tcaagtgagg acaaaatccc agtccccacc caccccaagc tgtaggcaca aggtgtatgg     3060
ggtttcgagg ctcagctcca catctacttt tgcctccagg gctactaatc agtgctgagg     3120
tctcaggact gggttaagcc tctgtggtct gatggagcct tcagaggctc ctgcttcgag     3180
```

```
gagtgccctc cgggctggtg agagagagtc ctaagcacct agggctggct actgagcccc    3240
gtctgcacct cgcactcagc tccaacaccg cgagttcata ccctggtgta ctggtttccc    3300
agagcttcca cagtcctccc ctggagcgtg attgcagccc ccaaaaacac ccccttgcta    3360
aaagcagggg agaggttagt acccctagc ttccagaact tagttctggc acccaggctg    3420
tagggtttg gtttatccct tttgtaccct gaagggggt ataggaagca gccaggagta     3480
caggcagacc tttggagtct agggagaagg accatgtccc caaccttgtg ctggccaatt    3540
aactccagca ttcagcccct tatgcaagtg gggaaaccga agcccagagg agacagggtt    3600
tgctgaagtg cacacagaga gtcagagaag agccagcagg gggcaggaga agactcttgc    3660
ggagctgaga cttccaactg ggctctcctc ttgagggtct atgatgcctt ggaccagaga    3720
ccaaacctct tgagcctgtt tcctcatctg tgagatgtac ggggtgggcc aggcaccgtg    3780
gctcatgcct gtaatcccag cactctggga gaccaaggcg gactaatcac aaggtcagga    3840
gttcgagacc agcctggcca acatcgtgaa acccccatct ctactaaaaa tacaaaaaat    3900
tagccagggg tggtggcgag cacctgtaat cccagctact cgggaggctg aggcaggaga    3960
atctcttgaa cccgggaggt gttgcagtga gctgagatca caccattgcc ctccagcccc    4020
agcaacagtg tgagactccg tctcaaaaaa aaaaaaaaaa aaaaaaaaaa aaaaaagat    4080
gtacggggtg gttgtgagga tggaatgggg gtaactcacc atcaggatgg gcatggcagg    4140
gtggggcagg gagaatgagg agtggaccctt ccagcctggg ccttctccct gcccttgcta    4200
cactgagagc cctgtggggg caatgtggga tggtaaccgg caggcccagg gccttctcca    4260
gtcaggccag gtgagggtg agagtgttgg gctgctgtgg ccactgacaa aggccccaga    4320
gggtcgggc acaaggctga accctgactc cttcccttcc ctgacctttc ccagcctggc    4380
ctggaagccc tcagccccaa caccagctgc cgccacttcc ctctgctggt cagtagcagc    4440
ttctcacgtg tggacctatt caatgggctg ttgggaccag tacaggtcac tgcattgtat    4500
gtgacacgcc ttgacaacgt cacagtggca cacatgggca caatggatgg gcgtatcctg    4560
caggtgggtc ctcatcccca cagtccccta gccctgggtc cttgtctcca tccccatttt    4620
gctcacatct gacctgtcct aggtggagct ggtcaggtca ctaaactact tgctgtatgt    4680
gtccaacttc tcactgggtg acagtgggca gcccgtgcag cgggatgtca gtcgtcttgg    4740
ggaccaccta ctctttgcct ctggggacca ggtgaggtgg gcaggggcag ggcctggggc    4800
cagggttgtg ggatcacaga ctctccatcc aatcccaggga ggcattgaca tacaggccct    4860
accaccctag cctactgtgt accgggaggg tctataggc ccaatctctc cctccaggca     4920
ccctgagtc acctgtcttt cacccacagg ttttccaggt acctatccaa ggccctggct    4980
gccgccactt cctgacctgt gggcgttgcc taagggcatg gcatttcatg gctgtggct    5040
ggtgtgggaa catgtgcggc cagcagaagg agtgtcctgg ctcctggcaa caggaccact    5100
gcccacctaa gcttactgag gtatggcttc cctggcaggg cacaggtaag agtgggacag    5160
gctgggcctg gggtggtggt cagcaagtct tgatcacaat ttttctcagg tctggggggt    5220
gtccttcata tctacaagga gggcattctt gtcagagggg atgccacatg caaagacttg    5280
gaggcaggaa agtgcttgaa tgcaagtgac tccaaatggc tggagcgtgg ggaaggcaag    5340
gggtatggca ggagactttg gggaagcagg tggggctgag agagcccaac cccacatgag    5400
gactcaggct gtttccccca tttcagttcc accccacag tggacctcta aggggcagta    5460
caaggctgac cctgtgtggc tccaacttct accttcaccc ttctggtctg gtgcctgagg    5520
```

```
gaacccatca ggtcactgtg ggccaaagtc cctgccggcc actgcccaag dacagctcaa   5580
aactcaggta caatctggtc cctcccctcc ctttccctga aggggaaaac caagcagccc   5640
cttccccatg agaccctgtt ctctgcttat cagaggcaag gggggatggg ggaagctgca   5700
gtggttctga ctgcttttg agagtcaaaa aggtctctgt cccttttga ctttcatgt     5760
gcccttcctg tctgttcact catggaccag ccaaggttaa tctctgcccc accagaacct   5820
tccttccatg gagggaggca tgggtggaga aatgccattc tctggctcag aggagccctg   5880
tggcttgtgg caggcatgca tctaggcctg tgtaattcct ggctgacctc aggggttccc   5940
ctggtgcccc agaccagtgc cccggaaaga ctttgtagag gagtttgagt gtgaactgga   6000
gcccttgggc acccaggcag tggggcctac caacgtcagc ctcaccgtga ctaacatgcc   6060
accgggcaag cacttccggg tagacggcac ctccgtgctg agaggcttct ctttcatggt   6120
gaggctacct tgccctgtct gtgcccttgg ccagtgcatg gtacgggaag ggaggggctt   6180
ggagtggagg acctgcctaa gccacctcta tgtcctctta ggagccagtg ctgatagcag   6240
tgcaacccct ctttggccca cgggcaggag gcacctgtct cactcttgaa ggccagagtc   6300
tgtctgtagg caccagccgg gctgtgctgg tcaatgggac tgagtgtctg ctagcacggt   6360
aagtaccacc aggcaggcat ggggaggccgc agggttctat ccaggtgggg acccggattc   6420
tgtcaggatg gagggaagag tgcttgttac atggtcagtg tggtgtggag agcaggtcca   6480
ggaagaaaag actactgccc tcttcagccc agaggcaaga gagcccatca cagagtccaa   6540
tggctccagc caaggctgtg gggaacctgt ccctccttta ccctcttggg atgtcttcct   6600
gggaccacct tattttcaga cagaccatgg agtggggcag gtgggagaga taacagacga   6660
actgggagag gtcaacaggc ccctggaaga agtgggcctg gccatcacaa agagggtaac   6720
cttgagccca atctcttgtt cctgtagggt cagtgagggg cagcttttat gtgccacacc   6780
ccctgggggcc acggtggcca gtgtccccct tagcctgcag gtgggggggtg cccaggtacc   6840
tggttcctgg accttccagt acagagaaga ccctgtcgtg ctaagcatca gccccaactg   6900
tggctacatg taagcactgc ctctttgccc actctggcct ctggggaatg agagagccag   6960
ctttggagaa cacccaaagc ctaccaccct accctcttcc acagcaactc ccacatcacc   7020
atctgtggcc agcatctaac ttcagcatgg cacttagtgc tgtcattcca tgacgggctt   7080
agggcagtgg aaagcagggt gagtgagtgc tggccaggag ggaggaaggc tggatgagtt   7140
ccctgagctg cagcccaacc tcgtgctggg ctgaggcgag gagcaatcac aggtggggtt   7200
cctggctaat cactctcata ttggtcccag cagtgtgaga ggcagcttcc agagcagcag   7260
ctgtgccgcc ttcctgaata tgtggtccga daccccagg gatgggtggc agggaatctg   7320
agtgcccgag gggatggagc tgctggcttt acactgcctg gctttcgctt cctaccccca   7380
ccccatccac ccagtgccaa cctagttcca ctgaagcctg aggagcatgc cattaagttt   7440
gaggtaagtg taagggatag ggcagggac agttggggat ctgaaagtag ggccagcct    7500
actggctggt cctcatgacc ctctctgcag tatattgggc tgggcgctgt ggctgactgt   7560
gtgggtatca acgtgaccgt gggtggtgag agctgccagc acgagttccg ggggggacatg  7620
gttgtctgcc cctgcccccc atccctgcag cttggccagg atggtgcccc attgcaggta   7680
ggcagcccag ctggacctcc ctgggaaaca cgggcagagg gcctacaggc tgggcctgag   7740
ttgccacctg cccccaggtc tgcgtagatg gtgaatgtca tatcctgggt agagtggtgc   7800
ggccagggcc agatgggttc ccacagagca cgctccttgg tatcctgctg cctttgctgc   7860
tgcttgtggc tgcactggcg actgcactgg tcttcagcta ctggtggcgg aggaagcagc   7920
```

```
taggtgagtt ctctgctcct acctttaatc agcccctacc cccaaccaat ggcatcttca    7980
agtccctaca tcctctctct gcccaggact tagggatcta agtcctcccc agaggggtcg    8040
gcccctagga gcttggaaag ccaagccacc aaggattctc tttccacagt tcttcctccc    8100
aacctgaatg acctggcatc cctggaccag actgctggag ccacacccct gcctattctg    8160
tactcgggct ctgactacag aagtggcctt ggtgagatag tggaggcatg agaagctaaa    8220
gccaccccct gtccctacaa gctcctcatt ccctctcccc acagcactcc ctgccattga    8280
tggtctggat tccaccactt gtgtccatgg agcatccttc tccgatagtg aagatgaatc    8340
ctgtgtgcca ctgctgcgga aagagtccat ccagctaagg acctggact ctgcgctctt     8400
ggctgaggtc aaggatgtgc tgattcccca tgagcgggtg gtcacccaca gtgaccgagt    8460
cattggcaaa ggtgtggggg ccaggtgggg ctggggcaga gatggagtct caagatgaca    8520
taggctaggc caggcgtggt ggctcactcc tgtaatccca gcactttggg aggccgaggc    8580
gggcagatca tgaggtcagg agatcgagac cgtcctggct aacacagtga aaccccgtct    8640
ctactaaaaa tacaaaaaaa tattagccag ccatggtggc aggcgcctgt agtcccagct    8700
acttgggagg ctgaggcagg agaatggcat gaactcggga ggcggagctt gcagtgagcc    8760
aagattgcac cactgcactc cagcctgggc gacagagcga gactccttct caaaaaaaaa    8820
aaaaatgaca tgggctaaag ggacagttgg aacagatact gctctaacct tctcaccaac    8880
ctgtgtgacc ttgggtatac cacttaacct ctctgagcct ccatttgctc atctgtaaaa    8940
tggggatgag aaaagttctg tcttcagtgg gttctggtgt ggatcaatca ggcataggaa    9000
gattgtagcc tctgccatca agtggctgct gttttgttttt ggttttattt atggttttgt   9060
ttttgttttt gtgacagggt ctcactctgt tacccaggct ggagtgcaat ggcacaatca    9120
tggctcactg cagcctcgac ctccccagcc tcaggtgatc ctcctgcctc agcctcctga    9180
gtagctggga ttacaatcat gcaccaccat gcctggctaa tttttgttt attttttgta    9240
gagatgggcc tcgaatcatg ttgtccaggc tggcctcgaa ctcctggact caagcaatct    9300
gcctgcctaa ccttcccaaa gtgctgggat tacaggcatg agccaccgaa cccagcctgt    9360
tttattatat ttattttatt ttattttat ttttattcta ttttattatt attatttttt    9420
ttgagacaga atttcactct tgttgcccag gctggagtgc aatggcgcga tctcggctca    9480
ttgcaacctc ctcctcccgg gttcaagtga ttctcctgtc tcagcttcct gagtagctag    9540
gattacaggc gcctgccaca cacccggct aattttttagt attttttggta gagataggat    9600
ttcaccatgt tggccaggcc ggtctcgaac tcctgacctc aggtgatccg cccgcctcag    9660
cctcccaaag tgctaggatt acaggcatga gccactgccc ccagcctatt ttattttatt    9720
ttattttttt tttttttttg agaggagtc tcactctttc acccaggctg gagtgcagtg     9780
gcgcgatctc gactcactgc aagctccgcc tcccaggttc atgccattct cctgcctcag    9840
cctcccaagt agctgggact acaggcgcct gccaccgtgc ccggctaatt ttttgtattt    9900
ttagtagaga tgggtttca ccgtgttagc caggatggtc tcgatctcct gacctcatga     9960
tccacccgcc tcagcctccc aaagtgctgg gattacaggt gtgagccacc gcgcccggcc    10020
tatttttattt tttcaagatg gagtcttgct ctatcaccca ggctggagtg cagtggtgca   10080
atcttggctc actgcaacct cccctctcca ggttcaagca attctcctgc ctcaccctcc    10140
ctagtagctg ggattacagg cgcccgccac cacacctggc taattttttgt attttttagta  10200
gagatggggt ttcaccatgt tggccaggct ggtctcaaac tcctaacctc aggtgatctg    10260
```

```
cctgccttga tctcccaaag tgctgggatt acaggcgtga gccactgtat ccagcctatt    10320
tatttattta tttatttatt tatttatttta tttattttg agacagaacc tcactctgtc    10380
acccaggctg gagtgcagtg gcatgatctc agctcactgc aacctctgcc tcccggattc    10440
aagtgattct cctgcctcag cctcctaagt agctgggatt acagacgtgc accaccaagc    10500
ccgtctaatt tttgtatttt tagtagaaat ggagtttcat catgttggcc aggctggtct    10560
caaactcccg acctcaggtg atccgcccgc ctcggcctcc cgaagtgctg ggattacagg    10620
cgtgagccat cgcacccgac cctgctttat ttacttattt atttatttt atttttttga    10680
gacagagtct cactctattg cccaggctgg agtgcagtag tgcaatctcg gctcactgca    10740
acctctgcct cctggattca agcatttctc ctgcctcagc ctcctgagta gctgggatta    10800
caggggcctg ccactgccac cacacctgtc taatttttgt agttttagta gagacggggt    10860
ttcatcatgt tggccagact ggtcttgaac ccctgacctc agctgatcct cccgcccag    10920
catcccaaag tattaggatt aaaggcatga gccttttttt tttttttta atttaaaaaa    10980
aagacagcat ctcactatgt tacccaggct ggccttgaac tcctgggctt atgcgattct    11040
cttgcctcag cctcctgagt aactgggatt acaggcgcac tgcgcttggc ttctgctgct    11100
tttctttgag ggggatggag tctcgccctg tctctcaggc tggagtgcag tgacacgatc    11160
ttggctcact gcaacctctg cctcccgggt tcaagctatc ctcctgcctc aggctcccaa    11220
gcagctggga ctagagatgg ggtttcacca tattagccag gctggtctca aactcctgac    11280
ctcgtgatcc acccgccttg gcctctcaaa gtgctggcat tacaggtgtg agccactgca    11340
cgcagccctg ctgcttttt aaaatgtcag attgggccgg gtgtggtggc tcacacctgt    11400
aatcccagca ctttgggagg cctaggtggg tgaatcacaa gatcaggagt ttgagaccag    11460
cctggccaac atggtgaaac ccagtctcta ctaaaaatac aaaaaaatta gctgtgtgta    11520
gtggcagttg cctgtaatcc cagctactca ggaggctgag gcaggagaat cacttgaacc    11580
tgggaggcag aggttgcaat gagttgagat tgcaccactg cacttcagcc tgggcaagag    11640
tgagactcgg tctcaaaaaa aataaataaa aattaaaaat aaataaaatg tcagattggc    11700
cagtttagtg ctctgaggtc tggttgccaa tgagaatgtg tggtgtgagc cttgggccct    11760
ggatcccctc tcatcgactc attatgcacc tcacaccagg ccactttgga gttgtctacc    11820
acggagaata catagaccag gcccagaatc gaatccaatg tgccatcaag tcactaagtc    11880
gtaagtgggg cagaagatgg gaaggcagag ggaggggcct caggctggga ggattctttt    11940
tctctgtgtt cccaccttac tgagtgaccc tgagcaggag accttcattt cccatttccc    12000
catctgagcc ttataaaggg acgccctgcc ctgtgcctga cttgcgctgc tctgcaggca    12060
tcacagagat gcagcaggtg gaggccttcc tgcgagaggg gctgctcatg cgtggcctga    12120
accacccgaa tgtgctggct ctcattggta tcatgttgcc acctgagggc ctgccccatg    12180
tgctgctgcc ctatatgtgc cacggtgacc tgctccagtt catccgctca cctcagcggg    12240
tcagtgttca tctggctctg ggttggggc tgggcagcag ctggagaagg agctgctgtg    12300
cccttgccca ccaacccacc tgtgccccca gaaccccacc gtgaaggacc tcatcagctt    12360
tggcctgcag gtagcccgcg gcatggagta cctggcagag cagaagtttg tgcacaggga    12420
cctggctgcg cggaactgca tgtgagagtc cagagtagct ggggtgaagc aaaaggacag    12480
ggcatgaggg tgtgcggtgc tcaaggccgc ctcagggaag gcccactcc agccttgtcc    12540
tcccctctct gcaccttact ttttttgtct gcccagtgca gacttggact ggacactgtg    12600
gctttgaaat ttggccaggc gcggtggctc acgtctgtaa tcccagcact tgggaggct    12660
```

```
gaggaaggcg gatcatgagg tcaggagatc gagaccatcc tggctaacac ggtgaaaccc    12720
cgtctctact aaaaatacaa aaagattagc caggcgtggt ggcgggcccc tgtagtccca    12780
gctactcagg aggctgaggc gggagaatgg cgtgacccca ggaggcagag cttgcagtga    12840
gcggagatcg cgccactgca ctccagcctg ggtgacagag cgagactccg tctcaaaaaa    12900
aaaaaaaatt ctgtaagggc ctagaacagg tgggttcagg gcctggtaag ggccagtcct    12960
aagtgtgatc ctctccctac ccctaaggct ggacgagtca ttcacagtca aggtggctga    13020
ctttggtttg gcccgcgaca tcctggacag ggagtactat agtgttcaac agcatcgcca    13080
cgctcgccta cctgtgaagt ggatggcgct ggagagcctg cagacctata gatttaccac    13140
caagtctgat gtggtgaggc cccacctgcc ctacagtcca catggctttg cacccaaga    13200 acactgggcc tcacccattc agctctgaat gatctgagcc cagggagtcc ccagggtaga    13260
tgacccccac agcccatctg ctcacctctt gggcagatgt aagatggaat ctgacacctg    13320
ccagggctag aggaggctgg gaactcactg gctcctcaca gataatccag ggcctgccca    13380
gccccaactc tgggtaggat gaggtagtgg gaggagacag aggaaagaca caggtgatgt    13440
attgaggaat gagctctcag tggagggtag ggtcttccat ttccagctga aggactctgg    13500
gaggtagaag ccctggggga cccacctgcc cccaaatttg gggtgagttg agtcccctca    13560
cctccccctt tccacagtgg tcatttggtg tgctgctgtg ggaactgctg acacggggtg    13620
ccccaccata ccgccacatt gacccttttg accttaccca cttcctggcc cagggtcggc    13680
gcctgcccca gctgagtat tgccctgatt ctctgtgagt atgtggaggt ggtagtgggg    13740
agggaactgg gccccagaga catggaagag acaggagaca gagctcctgc ctggcttcct    13800
gactgaactt ctggttgact aggaaaggga ctctcgctgg gcctcaattt cctcatctgt    13860
gaactggtcc caccctcatg cagagtagga ccctgggagg acctcacagt tgccatggta    13920
acagcattct gagctcagag ttggggttga ggcccgtggt ttgattttcc cagtgctcct    13980
cctacccgac tcccactaac ggggtctgct ttccaccttt tcctctcatt taatctcgag    14040
gaaagattcc ataaccccca cagcaacccc ctctggatct ccaggtcagg tttttttcact    14100 gtatgtggtt tcagattccc cattcctgga gggatggcgg cagctgcatt gtcctcagtg    14160 cctacgggt gggttcggtg ctgaggttca gcttcatacg tagcaggtgt gcctgagctg    14220
tggctaggtc tgctgggtta gaacagagag aaccaggaca taggtaaaag tagttaacgc    14280
ctcctgtctc aggctgtgct ccaagaagga tgcgagtagc ccttcctcac agtcctacct    14340
gccttgggtt tgctcttact attcacttct ttaattcact gcctacccat atccagattg    14400
ggctcctgga aacagactca gctggagatt tatgtacggg gatttactga gaggttgggg    14460
gcaagggaag aaggactggg caggagaaat gtcacagaaa ctgcagccca tcccacaggg    14520
actgcttgaa ctgggatgac ccaccacagt tttctgaaat tgagaccaac aggccaggtc    14580
tttgtaccag gcattaatca gttactagta acaggctgtc cctggtgagg ggatgtgagc    14640
ttggcagagg cagttctctt ctgcctaggg caattcctag agagagcctc agtcaagaac    14700
catcagcagg caacactcct agccactggg aaagtaaagg ggtatctggg tggcacacca    14760
tagggtccac ttcagcagtc cagcccttct cctctctggg cctcaatttc ctcatctgta    14820
aagtggagac aacagtacca ccttccgaga gtctgagaat tatatgagat attgtgtgta    14880
gggtagagta ttatttcagg caggaatgac atccccaaga taatgggca ggcactagga    14940 cccagcaggt aaacctgggg aacctctgct tcaggaccag ggtgccactg gtgctgcccc    15000
```

-continued

```
aaatgctctt gcttcagaat tttttttttt tttttttgaga cagagtctca ctctgatgcc    15060
caggctggag tgcggtggcg caatgttggc tcactgcaac ctctgcctcc caggttcaag    15120
tgattctcct acctcagcct cctgagtaac tgggactaca ggcgtgtgcc accacgccca    15180 gtaattttt tttttttttt ttgagatgga gtctcgctct gttgcccagg ctggagtgca    15240
gtggtgcaat ctcggctcac tgcaagctcc gcctcccggg ttcacgccat tctcctgcct    15300
cagcctcccg agtagctggg actacaggcg cctgccacga cgcccggcta atattttgtg    15360
tttttagtag agacggggtt tcactgtgtt agccaggatg gtctcgatct cctgacctcg    15420
tgatccaccc accttggcct cccaaagtgc tgggattaca ggcgtgagcc accacgccca    15480
gctttgccca gttaatttt gtatttttag tagagatggg gtttcactat gttggccagg    15540
ctggtctcga actcctgacc tcgtgacctg cccacctcag cctcccaaag tgctgggatt    15600
acaggcatga gccactgccc ccggccactt caggattttt aattcctgct ttgctggacc    15660
caggcttcct tcctggaaga actgtgatga tgaccattgt acctcgtgag ctgggccttg    15720
tgcctagcac ttcacaggca tcagcctata tgcctacttc tctgtgatca gaggaggacc    15780
cagaggcaca gagaagttaa ggaacttatc caagatcaca tagcccaggc cacagggcac    15840
aggagcccaa gctcttaaca cctgaggtag ttcgacctct gccagggtgg aaggcagga    15900 ctggaacagt aatcataggg atgagaagag ctgcccctga ttgggtagtg ctaggtacta    15960
ggtcctgtca tctatcctca tccctgtgtg gcctgccaga ggtttaacag caagtgggtg    16020
gcccagaatc cttgggtgga aattgcctta acctgacatc cctttccccc aacaggtacc    16080
aagtgatgca gcaatgctgg gaggcagacc cagcagtgcg acccaccttc agagtactag    16140
tgggggaggt ggagcagata gtgtctgcac tgcttgggga ccattatgtg cagctgccag    16200
caacctacat gaacttgggc cccagcacct cgcatgagat gaatgtgcgt ccagaacagc    16260
cgcagttctc acccatgcca gggaatgtac gccggccccg gccactctca gagcctcctc    16320
ggcccacttg acttagttct tgggctggac ctgcttagct gccttgagct aaccccaagc    16380
tgcctctggg ccatgccagg ccagagggca gtggccctcc accttgttcc tgcccttaa    16440 cttttcagagg caataggtaa atggggccca ttaggtccct cactccacag agtgagccag    16500
tgagggcagt cctgcaacat gtatttatgg agtgcctgct gtggaccctg tcttctgggc    16560
acagtggact cagcagtgac cacaccaaca ctgacccttg aaccaataaa ggaacaaatg    16620
actattaaag cacaaa                                                   16636
```

<210> SEQ ID NO 2
<211> LENGTH: 4221
<212> TYPE: DNA
<213> ORGANISM: homo sapien

<400> SEQUENCE: 2

```
ggatcctcta gggtcccagc tcgcctcgat ggagctcctc ccgccgctgc ctcagtcctt      60
cctgttgctg ctgctgttgc ctgccaagcc cgcggcgggc gaggactggc agtgcccgcg    120 cacccccctac gcggcctctc gcgactttga cgtgaagtac gtggtgccca gcttctccgc    180
cggaggcctg gtacaggcca tggtgaccta cgagggcgca agaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg cccaggacc    360 ccacggccct cccggtgaca cagacacaaa ggtgctggtg ctggatcccg cgctgcctgc    420
gctggtcagt tgtggctcca gcctgcaggg ccgctgcttc ctgcatgacc tagagcccca    480
```

-continued

| | |
|---|---|
| agggacagcc gtgcatctgg cagcgccagc ctgcctcttc tcagcccacc ataaccggcc | 540 |
| cgatgactgc cccgactgtg tggccagccc attgggcacc cgtgtaactg tggttgagca | 600 |
| aggccaggcc tcctatttct acgtggcatc ctcactggac gcagccgtgg ctggcagctt | 660 |
| cagcccacgc tcagtgtcta tcaggcgtct caaggctgac gcctcgggat cgcaccggg | 720 |
| ctttgtggcg ttgtcagtgc tgcccaagca tcttgtctcc tacagtattg aatacgtgca | 780 |
| cagcttccac acgggagcct tcgtatactt cctgactgta cagccggcca gcgtgacaga | 840 |
| tgatcctagt gccctgcaca cacgcctggc acggcttagc gccactgagc cagagttggg | 900 |
| tgactatcgg gagctggtcc tcgactgcag atttgctcca aaacgcaggc gccgggggc | 960 |
| cccagaaggc ggacagccct accctgtgct gcaggtggcc cactccgctc cagtgggtgc | 1020 |
| ccaacttgcc actgagctga gcatcgccga gggccaggaa gtactatttg gggtctttgt | 1080 |
| gactggcaag gatggtggtc ctggcgtggg ccccaactct gtcgtctgtg ccttccccat | 1140 |
| tgacctgctg gacacactaa ttgatgaggg tgtggagcgc tgttgtgaat ccccagtcca | 1200 |
| tccaggcctc cggcgaggcc tcgacttctt ccagtcgccc agttttttgcc ccaacccggt | 1260 |
| tttccaggta cctatccaag gccctggctg ccgccacttc ctgacctgtg ggcgttgcct | 1320 |
| aagggcatgg catttcatgg gctgtggctg gtgtgggaac atgtgcggcc agcagaagga | 1380 |
| gtgtcctggc tcctggcaac aggaccactg cccacctaag cttactgagt tccaccccca | 1440 |
| cagtggacct ctaaggggca gtacaaggct gaccctgtgt ggctccaact tctaccttca | 1500 |
| cccttctggt ctggtgcctg agggaaccca tcaggtcact gtgggccaaa gtccctgccg | 1560 |
| gccactgccc aaggacagct caaaactcag accagtgccc cggaaagact tgtagagga | 1620 |
| gtttgagtgt gaactggagc ccttgggcac ccaggcagtg gggcctacca acgtcagcct | 1680 |
| caccgtgact aacatgccac cggcaagca cttccgggta gacggcacct ccgtgctgag | 1740 |
| aggcttctct ttcatggagc cagtgctgat agcagtgcaa ccctctttg gcccacgggc | 1800 |
| aggaggcacc tgtctcactc ttgaaggcca gagtctgtct gtaggcacca gccgggctgt | 1860 |
| gctggtcaat gggactgagt gtctgctagc acgggtcagt gaggggcagc ttttatgtgc | 1920 |
| cacacccct ggggccacgg tggccagtgt ccccttagc ctgcaggtgg ggggtgccca | 1980 |
| ggtacctggt tcctggacct tccagtacag agaagaccct gtcgtgctaa gcatcagccc | 2040 |
| caactgtggc tacatcaact cccacatcac catctgtggc cagcatctaa cttcagcatg | 2100 |
| gcacttagtg ctgtcattcc atgacgggct tagggcagtg gaaagcaggt gtgagaggca | 2160 |
| gcttccagag cagcagctgt gccgccttcc tgaatatgtg gtccgagacc cccagggatg | 2220 |
| ggtggcaggg aatctgagtg cccgagggga tggagctgct ggctttacac tgcctggctt | 2280 |
| tcgcttccta ccccaccccc atccacccag tgccaaccta gttccactga gcctgagga | 2340 |
| gcatgccatt aagtttgagt atattgggct gggcgctgtg gctgactgtg tgggtatcaa | 2400 |
| cgtgaccgtg gtggtgagag ctgccagca cgagttccgg ggggacatgg ttgtctgccc | 2460 |
| cctgccccca tccctgcagc ttggccagga tggtgcccca ttgcaggtct gcgtagatgg | 2520 |
| tgaatgtcat atcctgggta gagtggtgcg gccagggcca gatggggtcc cacagagcac | 2580 |
| gctccttggt atcctgctgc ctttgctgct gcttgtggct gcactggcga ctgcactggt | 2640 |
| cttcagctac tggtggcgga ggaagcagct agttcttcct cccaacctga atgacctggc | 2700 |
| atccctggac cagactgctg gagccacacc cctgcctatt ctgtactcgg gctctgacta | 2760 |
| cagaagtggc cttgcactcc ctgccattga tggtctggat tccaccactt gtgtccatgg | 2820 |

| | |
|---|---|
| agcatccttc tccgatagtg aagatgaatc ctgtgtgcca ctgctgcgga aagagtccat | 2880 |
| ccagctaagg gacctggact ctgcgctctt ggctgaggtc aaggatgtgc tgattcccca | 2940 |
| tgagcgggtg gtcacccaca gtgaccgagt cattggcaaa ggccactttg gagttgtcta | 3000 |
| ccacggagaa tacatagacc aggcccagaa tcgaatccaa tgtgccatca agtcactaag | 3060 |
| tcgcatcaca gagatgcagc aggtggaggc cttcctgcga gaggggctgc tcatgcgtgg | 3120 |
| cctgaaccac ccgaatgtgc tggctctcat tggtatcatg ttgccacctg agggcctgcc | 3180 |
| ccatgtgctg ctgccctata tgtgccacgg tgacctgctc cagttcatcc gctcacctca | 3240 |
| gcggaacccc accgtgaagg acctcatcag cttttggcctg caggtagccc gcggcatgga | 3300 |
| gtacctggca gagcagaagt tgtgcacag ggacctggct gcgcggaact gcatgctgga | 3360 |
| cgagtcattc acagtcaagg tggctgactt tggtttggcc cgcgacatcc tggacaggga | 3420 |
| gtactatagt gttcaacagc atcgccacgc tcgcctacct gtgaagtgga tggcgctgga | 3480 |
| gagcctgcag acctatagat ttaccaccaa gtctgatgtg tggtcatttg gtgtgctgct | 3540 |
| gtgggaactg ctgacacggg gtgccccacc ataccgccac attgacccct ttgaccttac | 3600 |
| ccacttcctg gcccagggtc ggcgcctgcc ccagcctgag tattgccctg attctctgta | 3660 |
| ccaagtgatg cagcaatgct gggaggcaga cccagcagtg cgacccacct tcagagtact | 3720 |
| agtgggggag gtggagcaga tagtgtctgc actgcttggg gaccattatg tgcagctgcc | 3780 |
| agcaacctac atgaacttgg gcccagcac ctcgcatgag atgaatgtgc gtccagaaca | 3840 |
| gccgcagttc tcacccatgc cagggaatgt acgccggccc cggccactct cagagcctcc | 3900 |
| tcggcccact tgacttagtt cttgggctgg acctgcttag ctgccttgag ctaaccccaa | 3960 |
| ggctgcctct gggccatgcc aggccagagc agtggccctc cacttgttcc tgcccttaaa | 4020 |
| ctttcagagg caataggtaa atgggcccat taggtccctc actccacaga gtgagccagt | 4080 |
| gagggcagtc ctgcaacatg tatttatgga gtgcctgctg tgaccctgtc ttctgggcac | 4140 |
| agtggactca gcagtgacca caccaacact gacccttgaa ccaataaagg aacaaatgac | 4200 |
| tattaaagca caaaaaaaaa a | 4221 |

```
<210> SEQ ID NO 3
<211> LENGTH: 4541
<212> TYPE: DNA
<213> ORGANISM: homo sapien

<400> SEQUENCE: 3
```

| | |
|---|---|
| ggauccucua ggucccagc ucgccucgau ggagcuccuc ccgccgcugc ucaguccuu | 60 |
| ccuguugcug cugcuguugc cugccaagcc cgcggcgggc gaggacuggc agugcccgcg | 120 |
| cacccccuac gcggccucuc gcgacuuuga cgugaaguac guggugccca gcuucuccgc | 180 |
| cggaggccug guacaggcca uggugaccua cgagggcgac agaaaugaga gugcugugu | 240 |
| uguagccaua cgcaaucgcc ugcaugugcu ugggccugac cugaagucug uccagagccu | 300 |
| ggccacgggc ccugcuggag acccuggcug ccagacugu gcagccugug cccaggacc | 360 |
| ccacggcccu cccggugaca cagacacaaa ggugcuggug cuggaucccg cgcugccugc | 420 |
| gcuggucagu uguggcucca gccugcaggg ccgcugcuuc cugcaugacc uagagcccca | 480 |
| agggacagcc gugcaucugg cagcgccagc cugccucuuc ucagcccacc auaaccggcc | 540 |
| cgaugacugc cccgacugug uggccagccc auugggcacc cguguaacug gguugagca | 600 |
| aggccaggcc uccuauuucu acgugggcau cucacuggac gcagccgugg cuggcagcuu | 660 |
| cagcccacgc ucagugucua ucaggcgucu caaggcugac gccucgggau ucgcaccggg | 720 |

-continued

| | | | | | |
|---|---|---|---|---|---|
| cuuugugggcg | uugucagugc | ugcccaagca | ucuugucucc | uacaguauug | aauacgugca | 780 |
| cagcuuccac | acgggagccu | ucguauacuu | ccugacugua | cagccggcca | gcgugacaga | 840 |
| ugauccuagu | gcccugcaca | cacgccuggc | acggcuuagc | gccacugagc | cagaguuggg | 900 |
| ugacuaucgg | gagcuggucc | ucgacugcag | auuugcucca | aaacgcaggc | gccgggggc | 960 |
| cccagaaggc | ggacagcccu | acccugugcu | gcaggug gcc | cacuccgcuc | caguggguge | 1020 |
| ccaacuugcc | acugagcuga | gcaucgccga | gggccaggaa | guacuauuug | gggcuuugu | 1080 |
| gacuggcaag | gauggugguc | cuggcgugg g | ccccaacucu | gucgucugug | ccuuccccau | 1140 |
| ugaccugcug | gacacacuaa | uugaugaggg | uguggagcgc | uguugugaau | ccccaguccca | 1200 |
| uccaggccuc | cggcgaggcc | ucgacuucuu | ccagucgccc | aguuuugcc | ccaacccgcc | 1260 |
| uggccuggaa | gcccucagcc | ccaacaccag | cugccgccac | uucccucugc | uggcagung | 1320 |
| cagcuucuca | cgguggacc | uauucaaugg | gcuguuggga | ccaguacagg | ucacugcauu | 1380 |
| guaugugaca | cgccuugaca | acgucacagu | ggcacacaug | ggcacaaugg | augggcguau | 1440 |
| ccugcaggug | gagcugguca | ggucacuaaa | cuacuugcug | uaugugucca | acuucucacu | 1500 |
| gggugacagu | gggcagcccg | ugcagcggga | ugucagucgu | cuuggggacc | accuacucuu | 1560 |
| ugccucuggg | gaccagguuu | uccagguacc | uauccgaggc | ccuggcugcc | gccacuuccu | 1620 |
| gaccugnggg | cguugccuaa | gggcauggca | uuucaugggc | uguggcuggu | gugggaacau | 1680 |
| gugcggccag | cagaaggagu | guccuggcuc | cuggcaacag | gaccacugcc | caccuaagcu | 1740 |
| uacugaguuc | caccccccaca | guggaccucu | aaggggcagu | acaaggcuga | cccugugugg | 1800 |
| cuccaacuuc | uaccuucacc | cuucuggucu | ggugccugag | ggaacccauc | aggucacugu | 1860 |
| gggccaaagu | cccugccggc | cacugcccaa | ggacagcuca | aaacucagac | cagugccccg | 1920 |
| gaaagacuuu | guagaggagu | uugaguguga | acuggagccc | uugggcaccc | aggcagug gg | 1980 |
| gccuaccaac | gucagccuca | ccgugacuaa | caugccaccg | ggcaagcacu | uccggguaga | 2040 |
| cggcaccucc | gugcugagag | gcuucucuuu | cauggagcca | gugcugauag | cagugcaacc | 2100 |
| ccucuuuggc | ccacgggcag | gaggcaccug | ucucacucuu | gaaggccaga | gucugucugu | 2160 |
| aggcaccagc | cgggcugugc | uggucaaugg | gacugagugu | cugcuagcac | gggucaguga | 2220 |
| ggggcagcuu | uuaugugcca | cacccccugg | ggccacggug | gccagugucc | cccuuagccu | 2280 |
| gcaggugggg | ggugcccagg | uaccugguuc | cuggaccuuc | caguacagag | aagacccugu | 2340 |
| cgugcuaagc | aucagcccca | acuguggcua | caucaacucc | cacaucacca | ucguggccaa | 2400 |
| gcaucuaacu | ucagcauggc | acuuagugcu | gucauuccau | gacgggcuua | gggcagugga | 2460 |
| aagcaggugu | gagaggcagc | uuccagagca | gcagcugugc | cgccuuccug | aauaugug gu | 2520 |
| ccagaccccc | cagggauggg | uggcagggaa | ucugagugcc | cgaggggaug | gagcugcugg | 2580 |
| cuuuacacug | ccuggcuuuc | gcuuccuacc | cccaccccau | ccacccagug | ccaaccuagu | 2640 |
| uccacugaag | ccugaggagc | augccauuaa | guuuagauau | auugggcugg | gcgcugug gc | 2700 |
| ugacugugug | gguaucaacg | ugaccgugg g | uggugagagc | ugccagcacg | aguuccgggg | 2760 |
| ggacaugguu | gucugccccc | ugcccccauc | ccugcagcuu | ggccaggaug | ugccccauu | 2820 |
| gcaggucugc | guagauggug | aaugcauau | ccugggauag | guggugcggc | cagggccaga | 2880 |
| ugggguccca | cagagcacgc | uccuugguau | ccugcugccu | uugcugcugc | uuguggcugc | 2940 |
| acuggcgacu | gcacuggucu | ucagcuacug | guggcggagg | aagcagcuag | uucuuccucc | 3000 |
| caaccugaau | gaccuggcau | cccuggacca | gacugcugga | gccacacccc | ugccuauucu | 3060 |

| | |
|---|---|
| guacucgggc ucugacuaca gaagugggccu ugcacucccu gccauugaug ugucuggauuc | 3120 |
| caccacuugu guccauggag cauccuucuc cgauagugaa gaugaauccu gugugccacu | 3180 |
| gcugcggaaa gaguccaucc agcuaaggga ccuggacucu gcgcucuugg cugaggucaa | 3240 |
| ggaugugcug auuccccaug agcgggugu cacccacagu gaccgagucau uggcaaagg | 3300 |
| ccacuuugga guugucuacc acggagaaua cauagaccag gcccagaauc gaauccaaug | 3360 |
| ugccaucaag ucacuaaguc gcaucacaga gaugcagcag guggaggccu uccugcgaga | 3420 |
| ggggcugcuc augcguggcc ugaaccaccc gaaugugcug gcucucauug uaucauguu | 3480 |
| gccaccugag ggccugcccc augugcugcu gcccuauaug ugccacggug accugcucca | 3540 |
| guucauccgc ucaccucagc ggaaccccac cgugaaggac cucaucagcu uggccugca | 3600 |
| gguagcccgc ggcauggagu accuggcaga gcagaaguuu ugcacaggg accuggcugc | 3660 |
| gcggaacugc augcuggacg agucauucac agucaaggug gcugacuuug guuggcccg | 3720 |
| cgacauccug gacagggagu acuauagugu ucaacagcau cgccacgcuc gccuaccugu | 3780 |
| gaagugggaug gcgcuggaga ccugcagac cuauagauuu accaccaagu cugaugugug | 3840 |
| gucauuuggu gugcugcugu gggaacugcu gacacggggu gccccaccau accgccacau | 3900 |
| ugacccuuuu gaccuuaccc acuuccggcc caggggcgg cgccugcccc agccugagua | 3960 |
| uugcccugau ucucuguacc aagugaugca gcaaugcugg gaggcagacc cagcaguggcg | 4020 |
| acccaccuuc agaguacuag uggggaggu ggagcagaua gugucugcac ugcuuggga | 4080 |
| ccauuaugug cagcugccag caaccuacau gaacuugggc ccagcaccu cgcaugagau | 4140 |
| gaaugugcgu ccagaacagc cgcaguucuc acccaugcca gggaaugua ccggcccg | 4200 |
| gccacucuca gagccuccuc ggcccacuug acuuaguucu ugggcuggac cugcuuagcu | 4260 |
| gccuugagcu aacccaagg cugccucugg gccaugccag gccagagcag uggcccucca | 4320 |
| ccuuguuccu gcccuuuaac uuucagagagc aauagguaaa ugggcccauu aggucccuca | 4380 |
| cuccacagag ugagcagug agggcagucc ugcaacaugu auuuauggag ugccugcugu | 4440 |
| ggacccuguc uucugggcac aguggacuca gcagugacca caccaacacu gacccuugaa | 4500 |
| ccaauaaagg aacaaaugac uauuaaagca caaaaaaaaa a | 4541 |

<210> SEQ ID NO 4
<211> LENGTH: 4139
<212> TYPE: DNA
<213> ORGANISM: homo sapien

<400> SEQUENCE: 4

| | |
|---|---|
| auggagcucc uccgccgcu gccucagucc uuccuguugc ugcugcuguu gccugccaag | 60 |
| cccgcggcgg gcgaggacug gcagugcccg cgcaccccu acgcggccuc ucgcgacuuu | 120 |
| gacgugaagu acguggugcc cagcuucucc gccggaggcc uguacaggc cauggugacc | 180 |
| uacgagggcg acagaaauga gagugcugug uuuguagcca uacgcaaucg ccugcaugug | 240 |
| cuugggccug accugaaguc uguccagagc cuggccacgg gcccugcugg agacccuggc | 300 |
| ugccagacgu gugcagccug ggcccagga ccccacggcc cucccgguga cacagacaca | 360 |
| aaggugcugg ugcuggaucc cgcgcugccu gcgcuggucaa guuguggcuc cagccugcag | 420 |
| ggccgcugcu uccugcauga ccuagagccc caagggacag ccgugcaucu ggcagcgcca | 480 |
| gccugccucu ucucagccca ccauaaccgg cccgaugacu gccccgacug uguggccagc | 540 |
| ccauggggca cccgugucaac ugugguugag caaggcaggc cuccuauuu cuacguggca | 600 |
| uccucacugg acgcagccgu ggcugccagc uucagcccac gcucagugguc uaucaggcgu | 660 |

```
cucaaggcug acgccucggg auucgcaccg ggcuuugugg cguugucagu gcugcccaag      720
caucuugucu ccuacaguau ugaauacgug cacagcuucc acacgggagc cuucguauac      780
uuccugacuu uacagccggc cagcgugaca gaugauccua ugcccugca cacacgccug       840 gcacggcuua gcgccacuga gccagaguug ggugacuauc gggagcuggu ccucgacugc      900
agauuugcuc caaaacgcag gcgccggggg gccccagaag gcggacagcc cuacccugug      960
cugcgggugc cccacccgc uccagugggu gcccaacuug ccacugagcu gagcaucgcc      1020
gagggccagg aaguacuauu uggggucuuu ugacuggca aggauggugg uccggcgug       1080 ggccccaacu cugucgucug ugccuucccc auugaccugc uggacacacu aauugaugag     1140 ggugug gagc gcuguuguga auccccaguc cauccaggcc uccggcgagg ccucgacuuc    1200
uuccagucgc ccaguuuuug ccccaacccg ccuggccugg aagcccucag ccccaacacc     1260
agcugccgcc acuucccucu gcuggucagu agcagcuucu cacgugugga ccuauucaau     1320
gggcuguugg gaccaguaca ggucacugca uuguaugug cacgccuuga caacgucaca     1380
guggcacaca ugggcacaau ggaugggcgu auccugcagg uggagcuggu caggucacua     1440
aacuacuugc uguaugguc caacuucuca cugggugaca gugggcagcc cgugcagcgg      1500
gaugucaguc gucuugggga ccaccuacuc uuugccucug ggaccaggu uuccaggua       1560 ccuauccaag gcccuggcug ccgccacuuc cugaccugug ggcguugccu aagggcaugg     1620
cauuucaugg gcuguggcug gugugggaac augugcggcc agcagaagga guguccuggc    1680
uccuggcaac aggaccacug cccaccuaag cuuacugagu uccacccca cagguggaccu    1740 cuaaggggca guacaaggcu gacccugugu ggcuccaacu ucuaccuuca cccuucuggu    1800 cugguugccug agggaaccca ucaggucacu gugggccaaa gucccugccg gccacgcccc    1860
aaggacagcu caaaacucag accagugccc cggaaagacu uguagagga guuugagugu     1920 gaacuggagc ccuugggcac ccaggcagug gggccuacca acgucagccu caccgugacu    1980
aacaugccac cgggcaagca cuuccgggua gacggcaccu ccgugcugag aggcuucucu     2040
uucauggagc cagucgugau agcagugcaa ccccucuuug gcccacgggc aggaggcacc     2100
ugucucacuc uugaaggcca gagucugucu guaggcacca gccgggcugu gcggucaau     2160 gggacugagu gucugcuagc acgggucagu gagggggcagc uuuuaugugc cacaccccu    2220 ggggccacgg uggccagugu cccccuuagc cugcaggugg gggugcccca gguaccuggu   2280
uccuggaccu uccaguacag agaagacccu gucgugcuaa gcaucagccc caacugugg c  2340 uacaucaacu cccacaucac caucugugc cagcaucuaa cuucagcaug cacuuuagug    2400
cugucauucc augacgggcu uagggcagug gaaagcaggu gugagaggca gcuuccagag   2460
cagcagcugu gccgccuucc ugaauaugu gucccgagacc cccagggaug gguggcaggg    2520
aaucugagug cccgagggga uggagcugcu ggcuuuacac ugccuggcuu ucgcuuccua    2580
ccccaccccc auccccccag ugccaaccua guuccacuga agccgagga gcaugccauu    2640 aaguuugagu auauugggcu gggcgcugug gcugacugug ugggaucaa cgugaccgug    2700 ggugugagaa gcugccagca cgaguuccgg ggggacaugg uugucugccc ccugcccca    2760 ucccugcagc uuggccagga ggugcccca uugcaggucu gcguagaugg ugaaugucau    2820
auccugggua gaguggugcg ccagggcca gauggggucc cacagagcac gcuccuuggu    2880
auccugcugc cuuugcugcu gcuugugcu gcacuggcga cugcacuggu cuucagcuac    2940
ugguggcgga ggaagcagcu aguucuuccu cccaaccuga augaccuggc auccuggac     3000
```

| | |
|---|---|
| cagacugcug gagccacacc ccugccuauu cuguacucgg gcucugacua cagaagugcc | 3060 |
| cuugcacucc cugccauuga uggucuggau uccaccacuu guguccaugg agcauccuuc | 3120 |
| uccgauagug aagaugaauc cugugugcca cugcugcgga aagaguccau ccagcuaagg | 3180 |
| gaccuggacu cugcgcucuu ggcugagguc acuuuggagu ugucuaccac ggagaauaca | 3240 |
| uagaccaggc ccagaaucga auccaaugug ccaucaaguc acuaagucgc aucacagaga | 3300 |
| ugcagcaggu ggaggccuuc cugcgagagg ggcugcucau gcguggccug aaccacccga | 3360 |
| augugcuggc ucucauuggu aucauguugc caccugaggg ccugcccau gugcugcugc | 3420 |
| ccuauaugug ccacggugac cugcuccagu ucauccgcuc accucagcgg aaccccaccg | 3480 |
| ugaaggaccu caucagcuuu ggccugcagg uagcccgcgg caugagcuac cuggcagagc | 3540 |
| agaaguuugu gcacagggac cuggcugcgc ggaacugcau gcuggacgag ucauucacag | 3600 |
| ucaaggugcc ugacuuuggu uuggcccgcg acauccugga cagggaguac uauaguguuc | 3660 |
| aacagcaucg ccacgcucgc cuaccuguga aguggauggc gcuggagagc cugcagaccu | 3720 |
| auagauuuac caccaagucu gaugugguca cauuggugu gcugcugugg aacugcuga | 3780 |
| cacggggugc cccaccauac cgccacauug accuuuuga ccuuaccac uccuggccc | 3840 |
| agggucggcg ccugccccag ccugaguauu gcccugauuc ucuguaccaa ugaugcagc | 3900 |
| aaugcuggga ggcagaccca gcagugcgac ccaccuucag aguacuagug ggggagugg | 3960 |
| agcagauagu gucugcacug cuugggggacc auuaugugca gcugcagca accuacauga | 4020 |
| acuugggccc cagcaccucg caugagauga augugcgucc agaacagccg caguucucac | 4080 |
| ccaugccagg gaaugacgc cggccccggc cacucucaga gccuccucgg cccacuuga | 4139 |

<210> SEQ ID NO 5
<211> LENGTH: 765
<212> TYPE: DNA
<213> ORGANISM: homo sapien

<400> SEQUENCE: 5

| | |
|---|---|
| auggagcucc ucccgccgcu gccucagucc uuccuguugc ugcugcccua uaugugccac | 60 |
| ggugaccugc uccaguucau ccgcucaccu cagcggaacc ccaccgugaa ggacccauc | 120 |
| agcuuuggcc ugcagguagc ccgcggcaug gaguaccugg cagagcagaa guuugugcac | 180 |
| agggaccugg cugcgcggaa cugcaugcug gacgagucau ucacagucaa gguggcugac | 240 |
| uuugguuugg cccgcgacau ccuggacagg gaguacuaua guguucaaca gcaucgccac | 300 |
| gcucgccuac cugugaagug gaugcgcug gagagccugc agaccuauag auuuaccacc | 360 |
| aagucugaug ugguucauu ggugugcug cugugggaac ugcugacacg ggugcccca | 420 |
| ccauaccgcc acauugaccc uuugaccuu acccacuucc uggcccaggg ucggcgccug | 480 |
| ccccagccug aguauugccc ugauucucug uaccaaguga ugcagcaaug cugggaggca | 540 |
| gacccagcag ugcgacccac cuucagagua cuaguggggg gaggugcagca gauaguguu | 600 |
| gcacugcuug ggaccauua ugugcagcug ccagcaaccu acaugaacuu ggccccagc | 660 |
| accucgcaug agaugaaugu gcguccagaa cagccgcagu ucucacccau gccagggaau | 720 |
| guacgccggc cccggccacu cucagagccu ccucggccca cuuga | 765 |

<210> SEQ ID NO 6
<211> LENGTH: 1725
<212> TYPE: DNA
<213> ORGANISM: homo sapien

<400> SEQUENCE: 6

| | |
|---|---|
| auggagcucc uccegeegeu geeucaguee uuceuguuge ugeugeuguu geeugeeaag | 60 |
| cccgcggcgg gcgaggacug gcagugcccg cgcacccccu acgcggccuc ucgcgacuuu | 120 |
| gacgugaagu acguggugcc cagcuucucc gccggaggcc ugguacaggc cauggugacc | 180 |
| uacgagggcg acagaaauga gagugcugug uuuguagcca uacgcaaucg ccugcaugug | 240 |
| cuugggccug accugaaguc uguccagagc cuggccacgg gcccugcugg agaccCuggc | 300 |
| ugccagacgu gugcagccug uggcccagga ccccacggcc cucccgguga cacagacaca | 360 |
| aaggugcugg ugcuggaucc cgcgcugccu gcgcuggucg guuguggcuc cagccugcag | 420 |
| ggccgcugcu uccugcauga ccuagagccc aagggacagc cgugcaucug gcagcgcca | 480 |
| gccugccucu ucucagccca ccauaaccgg cccgaugacu gccccgacug uguggccagc | 540 |
| ccauugggca cccguguaac ugugguugag caaggccagg ccuccuauuu cuacguggca | 600 |
| uccucacugg acgcagccgu ggcuggcagc uucagcccac gcucaguguc uaucaggcgu | 660 |
| cucaaggcug acgccucggg auucgcaccg ggcuuugugg cguugucagu gcugccuuug | 720 |
| cugcugcuug uggcugcacu ggcgacugca cuggucuuca gcuacggug gcggaggaag | 780 |
| cagcuaguuc uuccucccaa ccugaaugac cuggcauccc uggaccagac ugcuggagcc | 840 |
| acaccccugc cuauucugua cucgggcucu gacuacagaa guggccuugc acucccugcc | 900 |
| auugaugguc uggauccac cacuugguguc cauggagcau ccuucuccga uagugaagau | 960 |
| gaauccugug ugccacugcu gcggaaagag uccauccagc uaagggaccu ggacucugcg | 1020 |
| cucuuggcug aggucaagga ugugcugauu ccccaugagc ggguggucac ccacagugac | 1080 |
| cgagucauug gcaaaggcca cuuuggaguu gucuaccacg gagaauacau agaccaggcc | 1140 |
| cagaaucgaa uccaaugugc caucaaguca cuaagucgca ucacagagau gcagcaggug | 1200 |
| gaggccuucc ugcgagaggg gcugcucaug cguggccuga accacccgaa ugugcuggcu | 1260 |
| cucauuggua ucauguugcc accugagggc cugcccaug ugcugcugcc cuauaugugc | 1320 |
| cacgugacc ugcuccaguu caucgcuca ccucagcgga ccccaccgu gaaggaccuc | 1380 |
| aucagcuuug ccugcaggu agcccgcggc auggaguacc uggcagagca gaaguuugug | 1440 |
| cacagggacc uggcugcgcg gaacugcaug uaccaaguga ugcagcaaug cugggaggca | 1500 |
| gacccagcag ugcgacccac cuucagagua cuaguggggg agguggagca gauagugucu | 1560 |
| gcacugcuug ggaccauua ugugcagcug ccagcaaccu acaugaacuu ggccccagc | 1620 |
| accucgcaug agaugaaugu gcguccagaa cagccgcagu ucucacccau gccagggaau | 1680 |
| guacgccggc cccggccacu cucagagccu ccucggccca cuuga | 1725 |

<210> SEQ ID NO 7
<211> LENGTH: 2727
<212> TYPE: DNA
<213> ORGANISM: homo sapien

<400> SEQUENCE: 7

| | |
|---|---|
| atggagctcc tcccgccgct gcctcagtcc ttcctgttgc tgctgctgtt gcctgccaag | 60 |
| cccgcggcgg gcgaggactg gcagtgcccg cgcacccccT acgcggcctc tcgcgacttt | 120 |
| gacgtgaagt acgtggtgcc cagcttctcc gccggaggcc tggtacaggc catggtgacc | 180 |
| tacgagggcg acagaaatga gagtgctgtg tttgtagcca tacgcaatcg cctgcatgtg | 240 |
| cttgggcctg acctgaagtc tgtccagagc ctggccacgg gcctgctgg agaccctggc | 300 |
| tgccagacgt gtgcagcctg tggcccagga ccccacggcc ctcccggtga cacagacaca | 360 |

| | |
|---|---|
| aaggtgctgg tgctggatcc cgcgctgcct gcgctggtca gttgtggctc cagcctgcag | 420 |
| ggccgctgct tcctgcatga cctagagccc aagggacag ccgtgcatct ggcagcgcca | 480 |
| gcctgcctct tctcagccca ccataaccgg cccgatgact gccccgactg tgtggccagc | 540 |
| ccattgggca cccgtgtaac tgtggttgag caaggccagg cctcctattt ctacgtggca | 600 |
| tcctcactgg acgcagccgt ggctgccagc ttcagcccac gctcagtgtc tatcaggcgt | 660 |
| ctcaaggctg acgcctcggg attcgcaccg ggctttgtgg cgttgtcagt gctgcccaag | 720 |
| catcttgtct cctacagtat tgaatacgtg cacagcttcc acacgggagc cttcgtatac | 780 |
| ttcctgactg tacagccggc cagcgtgaca gatgatccta gtgccctgca cacacgcctg | 840 |
| gcacggctta gcgccactga ccagagttg ggtgactatc gggagctggt cctcgactgc | 900 |
| agatttgctc caaaacgcag gcgccggggg ccccagaag gcggacagcc ctaccctgtg | 960 |
| ctgcgggtgg cccactccgc tccagtgggt gcccaacttg ccactgagct gagcatcgcc | 1020 |
| gagggccagg aagtactatt tggggtcttt gtgactggca aggatggtgg tcctggcgtg | 1080 |
| ggccccaact ctgtcgtctg tgccttcccc attgacctgc tggacacact aattgatgag | 1140 |
| ggtgtggagc gctgttgtga atccccagtc catccaggcc tccggcgagg cctcgacttc | 1200 |
| ttccagtcgc ccagttttg cccccaacccg cctggcctgg aagccctcag ccccaacacc | 1260 |
| agctgccgcc acttccctct gctggtcagt agcagcttct cacgtgtgga cctattcaat | 1320 |
| gggctgttgg gaccagtaca ggtcactgca ttgtatgtga cacgccttga caacgtcaca | 1380 |
| gtggcacaca tgggcacaat ggatgggcgt atcctgcagg tggagctggt caggtcacta | 1440 |
| aactacttgc tgtatgtgtc caacttctca ctgggtgaca gtgggcagcc cgtgcagcgg | 1500 |
| gatgtcagtc gtcttgggga ccacctactc tttgcctctg ggaccaggt tttccaggta | 1560 |
| cctatccaag gccctggctg ccgccacttc ctgacctgtg ggcgttgcct aagggcatgg | 1620 |
| catttcatgg gctgtggctg gtgtgggaac atgtgcggcc agcagaagga gtgtcctggc | 1680 |
| tcctggcaac aggaccactg cccacctaag cttactgagt tccaccccca cagtggacct | 1740 |
| ctaaggggca gtacaaggct gaccctgtgt ggctccaact tctaccttca cccttctggt | 1800 |
| ctggtgcctg agggaaccca tcaggtcact gtgggccaaa gtccctgccg gccactgccc | 1860 |
| aaggacagct caaaactcag accagtgccc cggaaagact ttgtagagga gtttgagtgt | 1920 |
| gaactggagc ccttgggcac ccaggcagtg gggcctacca acgtcagcct caccgtgact | 1980 |
| aacatgccac cgggcaagca cttccgggta gacggcacct ccgtgctgag aggcttctct | 2040 |
| ttcatggagc cagtgctgat agcagtgcaa cccctctttg gcccacgggc aggaggcacc | 2100 |
| tgtctcactc ttgaaggcca gagtctgtct gtaggcacca gccgggctgt gctggtcaat | 2160 |
| gggactgagt gtctgctagc acgggucagu gaggggcagc uuuuaugugc cacaccccu | 2220 |
| ggggccacgg uggccagugu ccccuuagc cugcaggugg gggugccca gguaccuggu | 2280 |
| uccuggaccu uccaguacag agaagacccu gucgugcuaa gcaucagccc caacugugc | 2340 |
| uacaucaacu cccacaucac caucugugc cagcaucuaa cuucagcaug gcacuuagug | 2400 |
| cugucauucc augacgggcu uagggcagug gaaagcaggc agugugagag gcagcuucca | 2460 |
| gagcagcagc ugugccgccu uccugaauau gugguccgag accccaggg auggguggca | 2520 |
| gggaaucuga gugcccgagg ggauggagcu gcuggcuuua cacugccugg cuuucgcuuc | 2580 |
| cuaccccac cccauccacc cagugccaac cuaguuccac ugaagccuga ggagcaugcc | 2640 |
| auuaaguuug agguaagugu aagggauagg ggcagggaca guugggggauc ugaaaguagg | 2700 |
| ggccagccua cuggcugguc cucauga | 2727 |

<210> SEQ ID NO 8
<211> LENGTH: 1626
<212> TYPE: DNA
<213> ORGANISM: homo sapien

<400> SEQUENCE: 8

| | | | | | |
|---|---|---|---|---|---|
| auggagcucc | ucccgccgcu | gccucagucc | uuccuguugc | ugcugcuguu | gccugccaag | 60 |
| cccgcggcgg | gcgaggacug | gcagugcccg | cgcacccccu | acgcggccuc | ucgcgacuuu | 120 |
| gacgugaagu | acgugguugcc | cagcuucucc | gccggaggcc | ugguacaggc | cauggugacc | 180 |
| uacgagggcg | acagaaauga | gagugcugug | uuuguagcca | uacgcaaucg | ccugcaugug | 240 |
| cuugggccug | accugaaguc | uguccagagc | cuggccacgg | gcccugcugg | agacccuggc | 300 |
| ugccagacgu | gugcagccug | ugcccagga | ccccacggcc | cucccgguga | cacagacaca | 360 |
| aaggugcugg | ugcuggaucc | cgcgcugccu | gcgcuggucca | guugggcuc | cagccugcag | 420 |
| ggccgcugcu | uccugcauga | ccuagagccc | caagggacag | ccgugcaucu | ggcagcgcca | 480 |
| gccugccucu | ucucagccca | ccauaaccgg | cccgaugacu | gccccgacug | uguggccagc | 540 |
| ccauugggca | cccguguaac | ugugguugag | caaggccagg | ccuccuauuu | cuacguggca | 600 |
| uccucacugg | acgcagccgu | ggcugccagc | uucagcccac | gcucagugc | uaucaggcgu | 660 |
| cucaaggcug | acgccucggg | auucgcaccg | ggcuuugugg | cguugucagu | gcugcccaag | 720 |
| caucuugucu | ccuacaguau | ugaauacgug | cacagcuucc | acacgggagc | cuucguauac | 780 |
| uuccugacug | uacagccggc | cagcgugaca | gaugauccua | gugcccugca | cacacgccug | 840 |
| gcacggcuua | gcgccacuga | ccagagguug | ggugacuauc | gggagcuggu | ccucgacugc | 900 |
| agauuugcuc | caaaacgcag | gcgccggggg | gccccagaag | gcggacagcc | cuacccugug | 960 |
| cugcggguug | cccacuccgc | uccagugggu | gcccaacuug | ccacugagcu | gagcaucgcc | 1020 |
| gagggccagg | aaguacuauu | uggggucuuu | ugacuggca | aggauggugg | uccuggcgug | 1080 |
| ggccccaacu | cugucgucug | ugccuucccc | auugaccugc | uggacacacu | aauugaugag | 1140 |
| ggugugggagc | gcuguuguga | uccccagguc | cauccaggcc | uccggcgagg | ccucgacuuc | 1200 |
| uuccagucgc | ccaguuuuug | ccccaacccg | guuuccagg | uaccuauccag | aggcccuggc | 1260 |
| ugccgcacu | uccugaccug | uggggcguugc | cuaagggcau | ggcauuucau | gggcuguggc | 1320 |
| ugguguggga | acaugugcgg | ccagcagaag | gagugugccu | gcuccuggca | acaggaccac | 1380 |
| ugcccaccua | agcuuacuga | guuccacccc | cacaguggac | cucuaagggg | caguacaagg | 1440 |
| cugacccugu | guggcuccaa | cuucuaccuu | cacccuucug | gucuggugcc | ugagggaacc | 1500 |
| caucagguca | cuguggggcca | aagcccugc | cggccacugc | ccaaggacag | cucaaaacuc | 1560 |
| agguacaauc | uggucccucc | ccuccccuuuc | ccugaagggg | gaaaccaagc | agccccuucc | 1620 |
| ccauga | | | | | 1626 |

<210> SEQ ID NO 9
<211> LENGTH: 1944
<212> TYPE: DNA
<213> ORGANISM: homo sapien

<400> SEQUENCE: 9

| | | | | | |
|---|---|---|---|---|---|
| auggagcucc | ucccgccgcu | gccucagucc | uuccuguugc | ugcugcuguu | gccugccaag | 60 |
| cccgcggcgg | gcgaggacug | gcagugcccg | cgcacccccu | acgcggccuc | ucgcgacuuu | 120 |
| gacgugaagu | acgugguugcc | cagcuucucc | gccggaggcc | ugguacaggc | cauggugacc | 180 |

| | |
|---|---|
| uacgagggcg acagaaauga gagugcugug uuuguagcca uacgcaaucg ccugcaugug | 240 |
| cuugggccug accugaaguc uguccagagc cuggccacgg gcccugcugg agacccuggc | 300 |
| ugccagacgu gugcagccug ugcccaggga ccccacggcc cucccgguga cacagacaca | 360 |
| aaggugcugg ugcuggaucc cgcgcugccu gcgcugguca guuguggcuc cagccugcag | 420 |
| ggccgcugcu uccugcauga ccuagagccc caagggacag ccgugcaucu ggcagcgcca | 480 |
| gccugccucu ucucagccca ccauaaccgg cccgaugacu gccccgacug uguggccagc | 540 |
| ccauugggca cccguguaac ugugguugag caaggccagg ccuccuauuu cuacguggca | 600 |
| uccucacugg acgcagccgu ggcugccagc uucagcccac gcucaguguc uaucaggcgu | 660 |
| cucaaggcug acgccucggg auucgcaccg ggcuuugugg cguugucagu gcugcccaag | 720 |
| caucuugucu ccuacaguau ugaauacgug cacagcuucc acacgggagc cuucguauac | 780 |
| uuccugacug uacagccggc cagcgugaca gaugauccua gugcccugca cacacgccug | 840 |
| gcacggcuua gcgccacuga gccagaguug ggugacuauc gggagcuggu ccucgacugc | 900 |
| agauuugcuc caaaacgcag gcgccggggg gccccagaag gcggacagcc cuacccugug | 960 |
| cugcggguuu cccacuccgc uccagugggu gccaacuug ccacugagcu gagcaucgcc | 1020 |
| gagggccagg aaguacuauu uggggucuuu ugacuggca aggauggugg uccuggcgug | 1080 |
| ggccccaacu cugucgucug ugccuucccc auugaccugc uggacacacu aauugaugag | 1140 |
| ggugugagc gcuguugga auccccagu cauccaggcc ccggcgagg ccucgacuuc | 1200 |
| uuccagucgc ccaguuuuug ccccaacccg ccuggccugg aagcccucag ccccaacacc | 1260 |
| agcugccgcc acuucccucu gcuggucagu agcagcuucu cacgugugga ccauucaau | 1320 |
| gggcuguugg gaccaguaca ggucacugca uuguauguga cacgccuuga caacgucaca | 1380 |
| gguggcacaca ugggcacaau ggaugggcgu auccugcagg uggagcuggu cagqucacua | 1440 |
| aacuacuugc uguaugugc caacuucuca cugggugaca gugggcagcc cgugcagcgg | 1500 |
| gaugucaguc gucuugggga ccaccuacuc uuugccucug ggaccaggu uuccaggua | 1560 |
| ccuauccaag gcccuggcug ccgccacuuc cugaccugug ggcguugccu aagggcaugg | 1620 |
| cauuucaugg gcguggcug gugugggaac augugcggcc agcagaagga guguccuggc | 1680 |
| uccuggcaac aggaccacug cccaccuaag cuuacugagu ccaccccca caguggaccu | 1740 |
| cuaagggca guacaaggcu gaccccugugu ggcuccaacu ucuaccuuca cccuucggu | 1800 |
| cuggugccug agggaaccca ucaggucacu gugggccaaa gucccugccg ccacugccc | 1860 |
| aaggacagcu caaaacucag guacaaucug guccucccc ucccuuuccc ugaaggggga | 1920 |
| aaccaagcag ccccuuccccc auga | 1944 |

<210> SEQ ID NO 10
<211> LENGTH: 1488
<212> TYPE: DNA
<213> ORGANISM: homo sapien

<400> SEQUENCE: 10

| | |
|---|---|
| auggagcucc ucccgccgcu gccucagucc uuccuguugc ugcugcuguu gccugccaag | 60 |
| cccgcggcgg gcgaggacug gcagugcccg cgcacccccu acgcgccuc ucgcgacuuu | 120 |
| gacgugaagu acgugugcc cagcuucucc gccggaggcc ugguacaggc caugugacc | 180 |
| uacgagggcg acagaaauga gagugcugug uuuguagcca uacgcaaucg ccugcaugug | 240 |
| cuugggccug accugaaguc uguccagagc cuggccacgg gcccugcugg agacccuggc | 300 |
| ugccagacgu gugcagccug ugcccaggga ccccacggcc cucccgguga cacagacaca | 360 |

| | |
|---|---|
| aaggugcugg ugcuggaucc cgcgcugccu gcgcuggvca guuguggcuc cagccugcag | 420 |
| ggccgcugcu uccugcauga ccuagagccc aagggacag ccgugcaucu ggcagcgcca | 480 |
| gccugccucu ucucagccca ccauaaccgg cccgaugacu gccccgacug uguggccagc | 540 |
| ccauggca cccgvguaac uguggvugag caaggccagg ccuccuauuu cuacguggca | 600 |
| uccucacugg acgcagccgu ggcugccagc uucagcccac gcucagvguc uaucaggcgu | 660 |
| cucaaggcug acgccucggg auucgcaccg ggcuuugugg cguugucagu gcugcccaag | 720 |
| caucuugucu ccuacaguau ugaauacgug cacagcuucc acacgggagc cuucguauac | 780 |
| uuccugacug uacagccggc cagcgugaca gaugauccua gugcccugca cacgccug | 840 |
| gcacggcuua gcgccacuga gccagaguug ggugacuauc gggagcuggu ccucgacugc | 900 |
| agauuugcuc caaaacgcag gcgccggggg gccccagaag gcggacagcc cuacccugug | 960 |
| cugcggguugg cccacuccgc uccaguggu gcccaacuug ccacugagcu gagcaucgcc | 1020 |
| gagggccagg aaguacuauu uggggucuuu gugacuggca aggauggvgg uccuggcgug | 1080 |
| ggccccaacu cugucgucug ugccuucccc auugaccugc uggacacacu aauugaugag | 1140 |
| ggugvggagc gcuguuguga auccccaguc cauccaggcc uccggcgagg ccucgacuuc | 1200 |
| uuccagucgc ccaguuuuug ccccaacccg ccuggccugg aagcccucag ccccaacacc | 1260 |
| agcugccgcc acuucccucu gcuggucagu agcagcuucu cacgvgugga ccuauucaau | 1320 |
| gggcuguugg gaccaguaca ggucacugca uuguaugva cacgccuuga caacgucaca | 1380 |
| guggcacaca ugggcacaau ggaugggcgu auccugcagg ugggccuca uccccacagu | 1440 |
| ccccuagccc uggguccuug ucuccauccc cauuuugcuc acaucuga | 1488 |

<210> SEQ ID NO 11
<211> LENGTH: 4221
<212> TYPE: DNA
<213> ORGANISM: homo sapien

<400> SEQUENCE: 11

| | |
|---|---|
| ggatcctcta gggtcccagc tcgcctcgat ggagctcctc ccgccgctgc ctcagtcctt | 60 |
| cctgttgctg ctgctgttgc ctgccaagcc cgcggcgggc gaggactggc agtgcccgcg | 120 |
| caccccctac gcggcctctc gcgactttga cgtgaagtac gtggtgccca gcttctccgc | 180 |
| cggaggcctg gtacaggcca tggtgaccta cgagggcgag agaaatgaga gtgctgtgtt | 240 |
| tgtagccata cgcaatcgcc tgcatgtgct tgggcctgac ctgaagtctg tccagagcct | 300 |
| ggccacgggc cctgctggag accctggctg ccagacgtgt gcagcctgtg cccaggacc | 360 |
| ccacggccct cccggtgaca cagacacaaa ggtgctggtg ctggatcccg cgctgcctgc | 420 |
| gctggtcagt tgtggctcca gcctgcaggg ccgctgcttc ctgcatgacc tagagcccca | 480 |
| agggacagcc gtgcatctgg cagcgccagc ctgcctcttc tcagcccacc ataaccggcc | 540 |
| cgatgactgc cccgactgtg tggccagccc attgggcacc cgtgtaactg tggttgagca | 600 |
| aggccaggcc tcctatttct acgtggcatc ctcactggac gcagccgtgg ctggcagctt | 660 |
| cagcccacgc tcagtgtcta tcaggcgtct caaggctgac gcctcgggat tcgcaccggg | 720 |
| ctttgtggcg ttgtcagtgc tgcccaagca tcttgtctcc tacagtattg aatacgtgca | 780 |
| cagcttccac acgggagcct tcgtatactt cctgactgta cagccggcca gcgtgacaga | 840 |
| tgatcctagt gccctgcaca cacgcctggc acggcttagc gccactgagc cagagttggg | 900 |
| tgactatcgg gagctggtcc tcgactgcag atttgctcca aaacgcaggc gccgggggc | 960 |

-continued

```
cccagaaggc ggacagccct accctgtgct gcaggtggcc cactccgctc cagtgggtgc    1020
ccaacttgcc actgagctga gcatcgccga gggccaggaa gtactatttg gggtctttgt    1080
gactggcaag gatggtggtc ctggcgtggg ccccaactct gtcgtctgtg ccttccccat    1140
tgacctgctg gacacactaa ttgatgaggg tgtggagcgc tgttgtgaat ccccagtcca    1200
tccaggcctc cggcgaggcc tcgacttctt ccagtcgccc agttttttgcc ccaacccggt    1260 tttccaggta cctatccaag gccctggctg ccgccacttc ctgacctgtg ggcgttgcct    1320
aagggcatgg catttcatgg gctgtggctg gtgtgggaac atgtgcggcc agcagaagga    1380
gtgtcctggc tcctggcaac aggaccactg cccacctaag cttactgagt tccaccccca    1440
cagtggacct ctaaggggca gtacaaggct gaccctgtgt ggctccaact tctaccttca    1500
cccttctggt ctggtgcctg agggaaccca tcaggtcact gtgggccaaa gtccctgccg    1560
gccactgccc aaggacagct caaaactcag accagtgccc cggaaagact tgtagagga    1620 gtttgagtgt gaactggagc ccttgggcac ccaggcagtg gggcctacca acgtcagcct    1680
caccgtgact aacatgccac cgggcaagca cttccgggta gacggcacct ccgtgctgag    1740
aggcttctct ttcatggagc cagtgctgat agcagtgcaa cccctctttg gcccacgggc    1800
aggaggcacc tgtctcactc ttgaaggcca gagtctgtct gtaggcacca gccgggctgt    1860
gctggtcaat gggactgagt gtctgctagc acgggtcagt gaggggcagc ttttatgtgc    1920 cacccccct ggggccacgg tggccagtgt ccccccttagc ctgcaggtgg ggggtgccca    1980
ggtacctggt tcctggacct tccagtacag agaagaccct gtcgtgctaa gcatcagccc    2040
caactgtggc tacatcaact cccacatcac catctgtggc cagcatctaa cttcagcatg    2100
gcacttagtg ctgtcattcc atgacgggct tagggcagtg gaaagcaggt gtgagaggca    2160
gcttccagag cagcagctgt gccgccttcc tgaatatgtg gtccgagacc cccagggatg    2220
ggtggcaggg aatctgagtg cccgagggga tggagctgct ggctttacac tgcctggctt    2280
tcgcttccta ccccccaccc atccacccag tgccaaccta gttccactga gcctgaggga    2340
gcatgccatt aagtttgagt atattgggct gggcgctgtg gctgactgtg tgggtatcaa    2400
cgtgaccgtg ggtggtgaga gctgccagca cgagttccgg ggggacatgg ttgtctgccc    2460 cctgcccca tccctgcagc ttggccagga tggtgcccca ttgcaggtct gcgtagatgg    2520
tgaatgtcat atcctgggta gagtggtgcg gccaggggcca gatggggtcc cacagagcac    2580
gctccttggt atcctgctgc ctttgctgct gcttgtggct gcactggcga ctgcactggt    2640
cttcagctac tggtggcgga ggaagcagct agttcttcct cccaacctga atgacctggc    2700
atccctggac cagactgctg gagccacacc cctgcctatt ctgtactcgg gctctgacta    2760
cagaagtggc cttgcactcc ctgccattga tggtctggat tccaccactt gtgtccatgg    2820
agcatccttc tccgatagtg aagatgaatc ctgtgtgcca ctgctgcgga aagagtccat    2880
ccagctaagg gacctggact ctgcgctctt ggctgaggtc aaggatgtgc tgattcccca    2940
tgagcgggtg gtcaccccaca gtgaccgagt cattggcaaa ggccactttg gagttgtcta    3000
ccacggagaa tacatagacc aggcccagaa tcgaatccaa tgtgccatca agtcactaag    3060
tcgcatcaca gagatgcagc aggtggaggc cttcctgcga gagggctgc tcatgcgtgg    3120 cctgaaccac ccgaatgtgc tggctctcat tggtatcatg ttgccacctg agggcctgcc    3180
ccatgtgctg ctgccctata tgtgccacgg tgacctgctc cagttcatcc gctcacctca    3240
gcggaacccc accgtgaagg acctcatcag ctttggcctg caggtagccc gcggcatgga    3300
gtacctggca gagcagaagt tgtgcacag ggacctggct gcgcggaact gcatgctgga    3360
```

-continued

| | | | |
|---|---|---|---|
| cgagtcattc | acagtcaagg tggctgactt tggtttggcc cgcgacatcc tggacaggga | 3420 |
| gtactatagt | gttcaacagc atcgccacgc tcgcctacct gtgaagtgga tggcgctgga | 3480 |
| gagcctgcag | acctatagat ttaccaccaa gtctgatgtg tggtcatttg gtgtgctgct | 3540 |
| gtgggaactg | ctgacacggg gtgccccacc ataccgccac attgacccct ttgaccttac | 3600 |
| ccacttcctg | gcccagggtc ggcgcctgcc ccagcctgag tattgccctg attctctgta | 3660 |
| ccaagtgatg | cagcaatgct gggaggcaga cccagcagtg cgacccacct tcagagtact | 3720 |
| agtgggggag | gtggagcaga tagtgtctgc actgcttggg gaccattatg tgcagctgcc | 3780 |
| agcaacctac | atgaacttgg gccccagcac ctcgcatgag atgaatgtgc gtccagaaca | 3840 |
| gccgcagttc | tcacccatgc cagggaatgt acgccggccc cggccactct cagagcctcc | 3900 |
| tcggcccact | tgacttagtt cttgggctgg acctgcttag ctgccttgag ctaaccccaa | 3960 |
| ggctgcctct | gggccatgcc aggccagagc agtggccctc cacttgttcc tgcccttaa | 4020 |
| ctttcagagg | caataggtaa atgggcccat taggtccctc actccacaga gtgagccagt | 4080 |
| gagggcagtc | ctgcaacatg tatttatgga gtgcctgctg tgaccctgtc ttctgggcac | 4140 |
| agtggactca | gcagtgacca caccaacact gacccttgaa ccaataaagg aacaaatgac | 4200 |
| tattaaagca | caaaaaaaaa a | 4221 |

<210> SEQ ID NO 12
<211> LENGTH: 4541
<212> TYPE: DNA
<213> ORGANISM: homo sapien

<400> SEQUENCE: 12

| | | | |
|---|---|---|---|
| ggatcctcta | gggtcccagc tcgcctcgat ggagctcctc ccgccgctgc ctcagtcctt | 60 |
| cctgttgctg | ctgctgttgc ctgccaagcc cgcggcgggc gaggactggc agtgcccgcg | 120 |
| caccccctac | gcggcctctc gcgactttga cgtgaagtac gtggtgccca gcttctccgc | 180 |
| cggaggcctg | gtacaggcca tggtgaccta cgagggcgac agaaatgaga gtgctgtgtt | 240 |
| tgtagccata | cgcaatcgcc tgcatgtgct tgggcctgac ctgaagtctg tccagagcct | 300 |
| ggccacgggc | cctgctggag accctggctg ccagacgtgt gcagcctgtg gcccaggacc | 360 |
| ccacggccct | cccggtgaca cagacacaaa ggtgctggtg ctggatcccg cgctgcctgc | 420 |
| gctggtcagt | tgtggctcca gcctgcaggg ccgctgcttc ctgcatgacc tagagcccca | 480 |
| agggacagcc | gtgcatctgg cagcgccagc ctgcctcttc tcagcccacc ataaccggcc | 540 |
| cgatgactgc | cccgactgtg tggccagccc attgggcacc cgtgtaactg tggttgagca | 600 |
| aggccaggcc | tcctatttct acgtggcatc ctcactggac gcagccgtgg ctggcagctt | 660 |
| cagcccacgc | tcagtgtcta tcaggcgtct caaggctgac gcctcgggat tcgcaccggg | 720 |
| ctttgtggcg | ttgtcagtgc tgcccaagca tcttgtctcc tacagtattg aatacgtgca | 780 |
| cagcttccac | acgggagcct tcgtatactt cctgactgta cagccggcca gcgtgacaga | 840 |
| tgatcctagt | gccctgcaca cacgcctggc acggcttagc gccactgagc cagagttggg | 900 |
| tgactatcgg | gagctggtcc tcgactgcag atttgctcca aaacgcaggc gccgggggc | 960 |
| cccagaaggc | ggacagccct accctgtgct gcaggtggcc cactccgctc cagtgggtgc | 1020 |
| ccaacttgcc | actgagctga gcatcgccga gggccaggaa gtactatttg ggtctttgt | 1080 |
| gactggcaag | gatggtggtc ctggcgtggg ccccaactct gtcgtctgtg ccttcccat | 1140 |
| tgacctgctg | gacacactaa ttgatgaggg tgtggagcgc tgttgtgaat ccccagtcca | 1200 |

```
tccaggcctc cggcgaggcc tcgacttctt ccagtcgccc agttttgcc ccaacccgcc    1260
tggcctggaa gccctcagcc ccaacaccag ctgccgccac ttccctctgc tggtcagtag    1320
cagcttctca cgtgtggacc tattcaatgg gctgttggga ccagtacagg tcactgcatt    1380
gtatgtgaca cgccttgaca acgtcacagt ggcacacatg ggcacaatgg atgggcgtat    1440
cctgcaggtg gagctggtca ggtcactaaa ctacttgctg tatgtgtcca acttctcact    1500
gggtgacagt gggcagcccg tgcagcggga tgtcagtcgt cttggggacc acctactctt    1560
tgcctctggg gaccaggttt ccaggtacc tatccgaggc cctggctgcc gccacttcct    1620
gacctgtggg cgttgcctaa gggcatggca tttcatgggc tgtggctggt gtgggaacat    1680
gtgcggccag cagaaggagt gtcctggctc ctggcaacag gaccactgcc cacctaagct    1740
tactgagttc caccccaca gtggacctct aaggggcagt acaaggctga ccctgtgtgg    1800
ctccaacttc taccttcacc cttctggtct ggtgcctgag gaacccatc aggtcactgt    1860
gggccaaagt ccctgccggc cactgccaa ggacagctca aaactcagac cagtgccccg    1920
gaaagacttt gtagaggagt ttgagtgtga actggagccc ttgggcaccc aggcagtggg    1980
gcctaccaac gtcagcctca ccgtgactaa catgccaccg ggcaagcact tccgggtaga    2040
cggcacctcc gtgctgagag gcttctcttt catggagcca gtgctgatag cagtgcaacc    2100
cctctttggc ccacgggcag gaggcacctg tctcactctt gaaggccaga gtctgtctgt    2160
aggcaccagc cgggctgtgc tggtcaatgg gactgagtgt ctgctagcac gggtcagtga    2220
ggggcagctt ttatgtgcca caccccctgg ggccacggtg ccagtgtcc cccttagcct    2280
gcaggtgggg ggtgcccagg tacctggttc ctggaccttc cagtacagag aagaccctgt    2340
cgtgctaagc atcagcccca actgtggcta catcaactcc cacatcacca tctgtggcca    2400
gcatctaact tcagcatggc acttagtgct gtcattccat gacgggctta gggcagtgga    2460
aagcaggtgt gagaggcagc ttccagagca gcagctgtgc cgccttcctg aatatgtggt    2520
ccgagacccc cagggatggg tggcaggaa tctgagtgcc cgaggggatg gagctgctgg    2580
ctttacactg cctggctttc gcttcctacc cccacccat ccacccagtg ccaacctagt    2640
tccactgaag cctgaggagc atgccattaa gtttgagtat attgggctgg gcgctgtggc    2700
tgactgtgtg ggtatcaacg tgaccgtggg tggtgagagc tgccagcacg agttccgggg    2760
ggacatggtt gtctgccccc tgccccatc cctgcagctt ggccaggatg tgccccatt    2820
gcaggtctgc gtagatggtg aatgtcatat cctgggtaga gtggtgcggc cagggccaga    2880
tggggtccca cagagcacgc tccttggtat cctgctgcct ttgctgctgc ttgtggctgc    2940
actggcgact gcactggtct tcagctactg gtggcggagg aagcagctag ttcttcctcc    3000
caacctgaat gacctggcat ccctggacca gactgctgga gccacacccc tgcctattct    3060
gtactcgggc tctgactaca gaagtggcct tgcactccct gccattgatg gtctggattc    3120
caccacttgt gtccatggag catccttctc cgatagtgaa gatgaatcct gtgtgccact    3180
gctgcggaaa gagtccatcc agctaaggga cctggactct cgcgctcttgg ctgaggtcaa    3240
ggatgtgctg attcccccatg agcgggtggt cacccacagt gaccgagtca ttggcaaagg    3300
ccactttgga gttgtctacc acggagaata catagaccag gccagaatc gaatccaatg    3360
tgccatcaag tcactaagtc gcatcacaga gatgcagcag gtggaggcct tcctgcgaga    3420
ggggctgctc atgcgtggcc tgaaccacc gaatgtgctg gctctcattg gtatcatgtt    3480
gccacctgag ggcctgcccc atgtgctgct gccctatatg tgccacggtg acctgctcca    3540
gttcatccgc tcacctcagc ggaaccccac cgtgaaggac ctcatcagct ttggcctgca    3600
```

```
ggtagcccgc ggcatggagt acctggcaga gcagaagttt gtgcacaggg acctggctgc    3660
gcggaactgc atgctggacg agtcattcac agtcaaggtg gctgactttg gtttggcccg    3720
cgacatcctg gacagggagt actatagtgt tcaacagcat cgccacgctc gcctacctgt    3780
gaagtggatg cgcgctggag agcctgcagac ctatagattt accaccaagt ctgatgtgtg    3840
gtcatttggt gtgctgctgt gggaactgct gacacggggt gccccaccat accgccacat    3900 tgacccttt gaccttaccc acttcctggc ccagggtcgg cgcctgcccc agcctgagta    3960
ttgccctgat tctctgtacc aagtgatgca gcaatgctgg gaggcagacc cagcagtgcg    4020
acccaccttc agagtactag tgggggaggt ggagcagata tgtctgcac tgcttgggga    4080 ccattatgtg cagctgccag caacctacat gaacttgggc cccagcacct cgcatgagat    4140
gaatgtgcgt ccagaacagc cgcagttctc acccatgcca gggaatgtac gccggccccg    4200
gccactctca gagcctcctc ggcccacttg acttagttct tgggctggac ctgcttagct    4260
gccttgagct aaccccaagg ctgcctctgg gccatgccag gccagagcag tggccctcca    4320
ccttgttcct gcccttaac tttcagaggc aataggtaaa tgggcccatt aggtccctca    4380
ctccacagag tgagccagtg agggcagtcc tgcaacatgt atttatggag tgcctgctgt    4440
ggaccctgtc ttctgggcac agtggactca gcagtgacca caccaacact gacccttgaa    4500
ccaataaagg aacaaatgac tattaaagca caaaaaaaa a                         4541

<210> SEQ ID NO 13
<211> LENGTH: 4139
<212> TYPE: DNA
<213> ORGANISM: homo sapien

<400> SEQUENCE: 13
atggagctcc tcccgccgct gcctcagtcc ttcctgttgc tgctgctgtt gcctgccaag      60
cccgcggcgg gcgaggactg gcagtgcccg cgcaccccct acgcggcctc tcgcgacttt     120
gacgtgaagt acgtggtgcc cagcttctcc gccggaggcc tggtacaggc catggtgacc     180
tacgagggcg acagaaatga gagtgctgtg tttgtagcca tacgcaatcg cctgcatgtg     240
cttgggcctg acctgaagtc tgtccagagc ctggccacgg gcctgctgg agaccctggc     300 tgccagacgt gtgcagcctg tggcccagga ccccacggcc ctcccggtga cacagacaca     360
aaggtgctgg tgctggatcc cgcgctgcct gcgctggtca gttgtggctc cagcctgcag     420
ggccgctgct tcctgcatga cctagagccc aagggacag ccgtgcatct ggcagcgcca     480
gcctgcctct tctcagccca ccataaccgg cccgatgact gccccgactg tgtggccagc     540
ccattgggca cccgtgtaac tgtggttgag caaggccagg cctcctattt ctacgtggca     600
tcctcactgg acgcagccgt ggctgccagc ttcagcccac gctcagtgtc tatcaggcgt     660
ctcaaggctg acgcctcggg attcgcaccg ggctttgtgg cgttgtcagt gctgcccaag     720
catcttgtct cctacagtat tgaatacgtg cacagcttcc acgggagc cttcgtatac     780 ttcctgactg tacagccggc cagcgtgaca gatgatccta gtgccctgca cacgcctg     840 gcacggctta gcgccactga gccagagttg ggtgactatc gggagctggt cctcgactgc     900
agatttgctc aaaacgcag gcgccggggg gccagaag gcgacagcc ctaccctgtg      960 ctgcgggtgg cccactccgc tccagtgggt gcccaacttg ccactgagct gagcatcgcc    1020
gagggccagg aagtactatt tggggtcttt gtgactggca aggatggtgg tcctggcgtg    1080
ggccccaact ctgtcgtctg tgccttcccc attgacctgc tggacacact aattgatgag    1140
```

-continued

```
ggtgtggagc gctgttgtga atccccagtc catccaggcc tccggcgagg cctcgacttc    1200
ttccagtcgc ccagttttg  ccccaacccg cctggcctgg aagccctcag ccccaacacc    1260
agctgccgcc acttccctct gctggtcagt agcagcttct cacgtgtgga cctattcaat    1320
gggctgttgg gaccagtaca ggtcactgca ttgtatgtga cacgccttga caacgtcaca    1380
gtggcacaca tgggcacaat ggatgggcgt atcctgcagg tggagctggt caggtcacta    1440
aactacttgc tgtatgtgtc caacttctca ctgggtgaca gtgggcagcc cgtgcagcgg    1500
gatgtcagtc gtcttgggga ccacctactc tttgcctctg ggaccaggt  tttccaggta    1560 cctatccaag gccctggctg ccgccacttc ctgacctgtg ggcgttgcct aagggcatgg    1620
catttcatgg gctgtggctg gtgtgggaac atgtgcggcc agcagaagga gtgtcctggc    1680
tcctggcaac aggaccactg cccacctaag cttactgagt tccaccccca cagtggacct    1740
ctaaggggca gtacaaggct gaccctgtgt ggctccaact tctaccttca cccttctggt    1800
ctggtgcctg agggaaccca tcaggtcact gtgggccaaa gtccctgccg gccactgccc    1860
aaggacagct caaaactcag accagtgccc cggaaagact ttgtagagga gtttgagtgt    1920
gaactggagc ccttgggcac ccaggcagtg gggcctacca acgtcagcct caccgtgact    1980
aacatgccac cgggcaagca cttccgggta dacggcacct ccgtgctgag aggcttctct    2040
ttcatggagc cagtgctgat agcagtgcaa cccctctttg gcccacgggc aggaggcacc    2100
tgtctcactc ttgaaggcca gagtctgtct gtaggcacca gccgggctgt gctggtcaat    2160
gggactgagt gtctgctagc acgggtcagt gaggggcagc ttttatgtgc cacacccct    2220 ggggccacgg tggccagtgt ccccttagc  ctgcaggtgg gggtgccca  ggtacctggt    2280 tcctggacct tccagtacag agaagaccct gtcgtgctaa gcatcagccc caactgtggc    2340
tacatcaact cccacatcac catctgtggc cagcatctaa cttcagcatg gcacttagtg    2400
ctgtcattcc atgacgggct tagggcagtg gaaagcaggt gtgagaggca gcttccagag    2460
cagcagctgt gccgccttcc tgaatatgtg gtccgagacc cccagggatg ggtggcaggg    2520
aatctgagtg cccgagggga tggagctgct ggctttacac tgcctggctt tcgcttccta    2580
cccccacccc atccacccag tgccaaccta gttccactga agcctgagga gcatgccatt    2640
aagtttgagt atattgggct gggcgctgtg gctgactgtg tgggtatcaa cgtgaccgtg    2700
ggtggtgaga gctgccagca cgagttccgg ggggacatgg ttgtctgccc cctgccccca    2760
tccctgcagc ttggccagga tggtgcccca ttgcaggtct gcgtagatgg tgaatgtcat    2820
atcctgggta gagtggtgcg gccagggcca gatggggtcc cacagagcac gctccttggt    2880
atcctgctgc ctttgctgct gcttgtggct gcactggcga ctgcactggt cttcagctac    2940
tggtggcgga ggaagcagct agttcttcct cccaacctga tgacctggc  atccctggac    3000 cagactgctg gagccacacc cctgcctatt ctgtactcgg gctctgacta cagaagtggc    3060
cttgcactcc ctgccattga tggtctggat tccaccactt gtgtccatgg agcatccttc    3120
tccgatagtg aagatgaatc ctgtgtgcca ctgctgcgga aagagtccat ccagctaagg    3180
gacctggact ctgcgctctt ggctgaggtc actttggagt tgtctaccac ggagaataca    3240
tagaccaggc ccagaatcga atccaatgtg ccatcaagtc actaagtcgc atcacagaga    3300
tgcagcaggt ggaggccttc ctgcgagagg ggctgctcat gcgtggcctg aaccacccga    3360
atgtgctggc tctcattggt atcatgttgc cacctgaggg cctgcccat  gtgctgctgc    3420 cctatatgtg ccacggtgac ctgctccagt tcatccgctc acctcagcgg aaccccaccg    3480
tgaaggacct catcagcttt ggcctgcagg tagcccgcgg catggagtac ctggcagagc    3540
```

```
agaagtttgt gcacagggac ctggctgcgc ggaactgcat gctggacgag tcattcacag    3600
tcaaggtggc tgactttggt ttggcccgcg acatcctgga cagggagtac tatagtgttc    3660
aacagcatcg ccacgctcgc ctacctgtga agtggatggc gctggagagc ctgcagacct    3720
atagatttac caccaagtct gatgtgtggt catttggtgt gctgctgtgg gaactgctga    3780
cacggggtgc cccaccatac cgccacattg acccttttga ccttacccac ttcctggccc    3840
agggtcggcg cctgccccag cctgagtatt gccctgattc tctgtaccaa gtgatgcagc    3900
aatgctggga ggcagaccca gcagtgcgac ccaccttcag agtactagtg ggggaggtgg    3960
agcagatagt gtctgcactg cttggggacc attatgtgca gctgccagca acctacatga    4020
acttgggccc cagcacctcg catgagatga atgtgcgtcc agaacagccg cagttctcac    4080
ccatgccagg gaatgtacgc cggccccggc cactctcaga gcctcctcgg cccacttga     4139

<210> SEQ ID NO 14
<211> LENGTH: 765
<212> TYPE: DNA
<213> ORGANISM: homo sapien

<400> SEQUENCE: 14
atggagctcc tcccgccgct gcctcagtcc ttcctgttgc tgctgcccta tatgtgccac      60
ggtgacctgc tccagttcat ccgctcacct cagcggaacc ccaccgtgaa ggacctcatc     120
agctttggcc tgcaggtagc ccgcggcatg gagtacctgg cagagcagaa gtttgtgcac     180
agggacctgg ctgcgcggaa ctgcatgctg acgagtcat tcacagtcaa ggtggctgac     240
tttggtttgg cccgcgacat cctggacagg gagtactata gtgttcaaca gcatcgccac     300
gctcgcctac ctgtgaagtg gatggcgctg agagcctgc agacctatag atttaccacc     360
aagtctgatg tgtggtcatt tggtgtgctg ctgtgggaac tgctgacacg gggtgcccca     420
ccataccgcc acattgaccc ttttgacctt acccacttcc tggcccaggg tcggcgcctg     480
ccccagcctg agtattgccc tgattctctg taccaagtga tgcagcaatg ctgggaggca     540
gacccagcag tgcgacccac cttcagagta ctagtggggg aggtggagca gatagtgtct     600
gcactgcttg ggaccatta tgtgcagctg ccagcaacct acatgaactt gggccccagc     660
acctcgcatg agatgaatgt gcgtccagaa cagccgcagt tctcacccat gccagggaat     720
gtacgccggc cccggccact ctcagagcct cctcggccca cttga                    765

<210> SEQ ID NO 15
<211> LENGTH: 1725
<212> TYPE: DNA
<213> ORGANISM: homo sapien

<400> SEQUENCE: 15
atggagctcc tcccgccgct gcctcagtcc ttcctgttgc tgctgctgtt gcctgccaag      60
cccgcggcgg cgaggactg cagtgcccg cgcaccccct acgcggcctc tcgcgacttt     120
gacgtgaagt acgtggtgcc cagcttctcc gccggaggcc tggtacaggc catggtgacc     180
tacgagggcg acagaaatga gagtgctgtg tttgtagcca tacgcaatcg cctgcatgtg     240
cttgggcctg acctgaagtc tgtccagagc ctggccacgg gcctgctgg agaccctggc     300 tgccagacgt gtcagcctg tggcccagga ccccacggcc ctcccggtga cacagacaca     360
aaggtgctgg tgctggatcc cgcgctgcct gcgctggtca gttgtggctc cagcctgcag     420
ggccgctgct tcctgcatga cctagagccc caagggacag ccgtgcatct ggcagcgcca     480
```

```
gcctgcctct tctcagccca ccataaccgg cccgatgact gccccgactg tgtggccagc    540
ccattgggca cccgtgtaac tgtggttgag caaggccagg cctcctattt ctacgtggca    600
tcctcactgg acgcagccgt ggctggcagc ttcagcccac gctcagtgtc tatcaggcgt    660
ctcaaggctg acgcctcggg attcgcaccg ggctttgtgg cgttgtcagt gctgcctttg    720
ctgctgcttg tggctgcact ggcgactgca ctggtcttca gctactggtg gcggaggaag    780
cagctagttc ttcctcccaa cctgaatgac ctggcatccc tggaccagac tgctggagcc    840
acacccctgc ctattctgta tcgggctct gactacagaa gtggccttgc actccctgcc    900
attgatggtc tggattccac cacttgtgtc catggagcat ccttctccga tagtgaagat    960
gaatcctgtg tgccactgct gcggaaagag tccatccagc taagggacct ggactctgcg    1020
ctcttggctg aggtcaagga tgtgctgatt ccccatgagc gggtggtcac ccacagtgac    1080
cgagtcattg gcaaaggcca cttggagtt gtctaccacg agaatacat agaccaggcc    1140 cagaatcgaa tccaatgtgc catcaagtca ctaagtcgca tcacagagat gcagcaggtg    1200
gaggccttcc tgcgagaggg gctgctcatg cgtggcctga accacccgaa tgtgctggct    1260
ctcattggta tcatgttgcc acctgagggc ctgccccatg tgctgctgcc ctatatgtgc    1320
cacggtgacc tgctccagtt catccgctca cctcagcgga accccaccgt gaaggacctc    1380
atcagctttg gcctgcaggt agcccgcggc atggagtacc tggcagagca gaagtttgtg    1440
cacagggacc tggctgcgcg gaactgcatg taccaagtga tgcagcaatg ctgggaggca    1500
gacccagcag tgcgacccac cttcagagta ctagtggggg aggtggagca gatagtgtct    1560
gcactgcttg ggaccatta tgtgcagctg ccagcaacct acatgaactt gggccccagc    1620
acctcgcatg agatgaatgt gcgtccagaa cagccgcagt tctcacccat gccagggaat    1680
gtacgccggc cccggccact ctcagagcct cctcggccca cttga    1725

<210> SEQ ID NO 16
<211> LENGTH: 2727
<212> TYPE: DNA
<213> ORGANISM: homo sapien

<400> SEQUENCE: 16
atggagctcc tcccgccgct gcctcagtcc ttcctgttgc tgctgctgtt gcctgccaag    60
cccgcggcgg gcgaggactg gcagtgcccg cgcaccccct acgcggcctc tcgcgacttt    120
gacgtgaagt acgtggtgcc cagcttctcc gccggaggcc tggtacaggc catggtgacc    180
tacgagggcg acagaaatga gagtgctgtg tttgtagcca tacgcaatcg cctgcatgtg    240
cttgggcctg acctgaagtc tgtccagagc ctggccacgg gccctgctgg agaccctggc    300
tgccagacgt gtgcagcctg tggcccagga ccccacggcc ctcccggtga cacagacaca    360
aaggtgctgg tgctggatcc cgcgctgcct gcgctggtca gttgtggctc cagcctgcag    420
ggccgctgct tcctgcatga cctagagccc aagggacag ccgtgcatct ggcagcgcca    480
gcctgcctct tctcagccca ccataaccgg cccgatgact gccccgactg tgtggccagc    540
ccattgggca cccgtgtaac tgtggttgag caaggccagg cctcctattt ctacgtggca    600
tcctcactgg acgcagccgt ggctgccagc ttcagcccac gctcagtgtc tatcaggcgt    660
ctcaaggctg acgcctcggg attcgcaccg ggctttgtgg cgttgtcagt gctgcccaag    720
catcttgtct cctacagtat tgaatacgtg cacagcttcc acacgggagc cttcgtatac    780
ttcctgactg tacagccggc cagcgtgaca atgatcctg tgccctgca cacgcgcctg    840 gcacggctta gcgccactga gccagagttg ggtgactatc gggagctggt cctcgactgc    900
```

```
agatttgctc caaaacgcag gcgccggggg gccccagaag gcggacagcc ctaccctgtg      960
ctgcgggtgg cccactccgc tccagtgggt gcccaacttg ccactgagct gagcatcgcc     1020
gagggccagg aagtactatt tggggtcttt gtgactggca aggatggtgg tcctggcgtg     1080
ggccccaact ctgtcgtctg tgccttcccc attgacctgc tggacacact aattgatgag     1140
ggtgtggagc gctgttgtga atccccagtc catccaggcc tccggcgagg cctcgacttc     1200
ttccagtcgc ccagttttttg ccccaacccg cctggcctgg aagccctcag ccccaacacc     1260
agctgccgcc acttccctct gctggtcagt agcagcttct cacgtgtgga cctattcaat     1320
gggctgttgg gaccagtaca ggtcactgca ttgtatgtga cacgccttga caacgtcaca     1380
gtggcacaca tgggcacaat ggatgggcgt atcctgcagg tggagctggt caggtcacta     1440
aactacttgc tgtatgtgtc caacttctca ctgggtgaca gtgggcagcc cgtgcagcgg     1500
gatgtcagtc gtcttgggga ccacctactc tttgcctctg ggaccaggt tttccaggta     1560 cctatccaag gccctggctg ccgccacttc ctgacctgtg ggcgttgcct aagggcatgg     1620
catttcatgg gctgtggctg gtgtgggaac atgtgcggcc agcagaagga gtgtcctggc     1680
tcctggcaac aggaccactg cccacctaag cttactgagt tccacccca cagtggacct     1740 ctaaggggca gtacaaggct gaccctgtgt ggctccaact tctaccttca cccttctggt     1800
ctggtgcctg agggaaccca tcaggtcact gtgggccaaa gtccctgccg gccactgccc     1860
aaggacagct caaaactcag accagtgccc cggaaagact ttgtagagga gtttgagtgt     1920
gaactggagc ccttgggcac ccaggcagtg gggcctacca acgtcagcct caccgtgact     1980
aacatgccac cgggcaagca cttccgggta gacggcacct ccgtgctgag aggcttctct     2040
ttcatggagc cagtgctgat agcagtgcaa cccctctttg gcccacgggc aggaggcacc     2100
tgtctcactc ttgaaggcca gagtctgtct gtaggcacca gccgggctgt gctggtcaat     2160
gggactgagt gtctgctagc acgggtcagt gaggggcagc ttttatgtgc cacacccct     2220 ggggccacgg tggccagtgt cccccttagc ctgcaggtgg ggggtgccca ggtacctggt     2280
tcctggacct tccagtacag agaagaccct gtcgtgctaa gcatcagccc caactgtggc     2340
tacatcaact cccacatcac catctgtggc cagcatctaa cttcagcatg gcacttagtg     2400
ctgtcattcc atgacgggct tagggcagtg gaaagcaggc agtgtgagag gcagcttcca     2460
gagcagcagc tgtgccgcct tcctgaatat gtggtccgag accccagggg atgggtggca     2520
gggaatctga gtgcccgagg ggatggagct gctggcttta cactgcctgg ctttcgcttc     2580 ctaccccac cccatccacc cagtgccaac ctagttccac tgaagcctga ggagcatgcc     2640
attaagtttg aggtaagtgt aagggatagg ggcagggaca gttggggatc tgaaagtagg     2700
ggccagccta ctggctggtc ctcatga                                        2727

<210> SEQ ID NO 17
<211> LENGTH: 1626
<212> TYPE: DNA
<213> ORGANISM: homo sapien

<400> SEQUENCE: 17
atggagctcc tcccgccgct gcctcagtcc ttcctgttgc tgctgctgtt gcctgccaag       60
cccgcggcgg gcgaggactg gcagtgcccg cgcacccct acgcggcctc tcgcgacttt      120
gacgtgaagt acgtggtgcc cagcttctcc gccggaggcc tggtacaggc catggtgacc      180
tacgagggcg acagaaatga gagtgctgtg tttgtagcca tacgcaatcg cctgcatgtg      240
```

| | |
|---|---|
| cttgggcctg acctgaagtc tgtccagagc ctggccacgg gccctgctgg agaccctggc | 300 |
| tgccagacgt gtgcagcctg tggcccagga ccccacggcc ctcccggtga cacagacaca | 360 |
| aaggtgctgg tgctggatcc cgcgctgcct gcgctggtca gttgtggctc cagcctgcag | 420 |
| ggccgctgct tcctgcatga cctagagccc aagggacag ccgtgcatct ggcagcgcca | 480 |
| gcctgcctct tctcagccca ccataaccgg cccgatgact gccccgactg tgtggccagc | 540 |
| ccattgggca cccgtgtaac tgtggttgag caaggccagg cctcctattt ctacgtggca | 600 |
| tcctcactgg acgcagccgt ggctgccagc ttcagcccac gctcagtgtc tatcaggcgt | 660 |
| ctcaaggctg acgcctcggg attcgcaccg ggctttgtgg cgttgtcagt gctgcccaag | 720 |
| catcttgtct cctacagtat tgaatacgtg cacagcttcc acgggagc cttcgtatac | 780 |
| ttcctgactg tacagccggc cagcgtgaca atgatccta gtgccctgca cacgcctg | 840 |
| gcacggctta gcgccactga gccagagttg ggtgactatc gggagctggt cctcgactgc | 900 |
| agatttgctc caaaacgcag gcgccggggg gccccagaag gcggacagcc ctaccctgtg | 960 |
| ctgcgggtgg cccactccgc tccagtgggt gcccaacttg ccactgagct gagcatcgcc | 1020 |
| gagggccagg aagtactatt tggggtcttt gtgactggca aggatggtgg tcctggcgtg | 1080 |
| ggccccaact ctgtcgtctg tgccttcccc attgacctgc tggacacact aattgatgag | 1140 |
| ggtgtggagc gctgttgtga atccccagtc catccaggcc tccggcgagg cctcgacttc | 1200 |
| ttccagtcgc ccagttttg ccccaacccg gtttttcagg tacctatcca aggccctggc | 1260 |
| tgccgccact tcctgaccct gggcgttgc ctaagggcat ggcatttcat gggctgtggc | 1320 |
| tggtgtggga acatgtgcgg ccagcagaag gagtgtcctg ctcctggca acaggaccac | 1380 |
| tgcccaccta agcttactga gttccacccc cacagtggac ctctaagggg cagtacaagg | 1440 |
| ctgaccctgt gtggctccaa cttctacctt caccttctg gtctggtgcc tgagggaacc | 1500 |
| catcaggtca ctgtgggcca aagtccctgc cggccactgc caaggacag ctcaaaactc | 1560 |
| aggtacaatc tggtccctcc cctcccttc cctgaagggg gaaaccaagc agccccttcc | 1620 |
| ccatga | 1626 |

<210> SEQ ID NO 18
<211> LENGTH: 1944
<212> TYPE: DNA
<213> ORGANISM: homo sapien

<400> SEQUENCE: 18

| | |
|---|---|
| atggagctcc tcccgccgct gcctcagtcc ttcctgttgc tgctgctgtt gcctgccaag | 60 |
| cccgcggcgg gcgaggactg gcagtgcccg cgcaccccct acgcggcctc tcgcgacttt | 120 |
| gacgtgaagt acgtggtgcc cagcttctcc gccggaggcc tggtacaggc catggtgacc | 180 |
| tacgagggcg acagaaatga gagtgctgtg tttgtagcca tacgcaatcg cctgcatgtg | 240 |
| cttgggcctg acctgaagtc tgtccagagc ctggccacgg gccctgctgg agaccctggc | 300 |
| tgccagacgt gtgcagcctg tggcccagga ccccacggcc ctcccggtga cacagacaca | 360 |
| aaggtgctgg tgctggatcc cgcgctgcct gcgctggtca gttgtggctc cagcctgcag | 420 |
| ggccgctgct tcctgcatga cctagagccc aagggacag ccgtgcatct ggcagcgcca | 480 |
| gcctgcctct tctcagccca ccataaccgg cccgatgact gccccgactg tgtggccagc | 540 |
| ccattgggca cccgtgtaac tgtggttgag caaggccagg cctcctattt ctacgtggca | 600 |
| tcctcactgg acgcagccgt ggctgccagc ttcagcccac gctcagtgtc tatcaggcgt | 660 |
| ctcaaggctg acgcctcggg attcgcaccg ggctttgtgg cgttgtcagt gctgcccaag | 720 |

```
catcttgtct cctacagtat tgaatacgtg cacagcttcc acacgggagc cttcgtatac    780
ttcctgactg tacagccggc cagcgtgaca gatgatccta gtgccctgca cacacgcctg    840
gcacggctta gcgccactga gccagagttg ggtgactatc gggagctggt cctcgactgc    900
agatttgctc caaaacgcag gcgccggggg cccccagaag gcggacagcc tacccctgtg    960
ctgcgggtgg cccactccgc tccagtgggt gcccaacttg ccactgagct gagcatcgcc   1020
gagggccagg aagtactatt tggggtcttt gtgactggca aggatggtgg tcctggcgtg   1080
ggccccaact ctgtcgtctg tgccttcccc attgacctgc tggacacact aattgatgag   1140
ggtgtggagc gctgttgtga atccccagtc catccaggcc tccggcgagg cctcgacttc   1200
ttccagtcgc ccagtttttg ccccaacccg cctggcctgg aagccctcag ccccaacacc   1260
agctgccgcc acttccctct gctggtcagt agcagcttct cacgtgtgga cctattcaat   1320
gggctgttgg gaccagtaca ggtcactgca ttgtatgtga cacgccttga caacgtcaca   1380
gtggcacaca tgggcacaat ggatgggcgt atcctgcagg tggagctggt caggtcacta   1440
aactacttgc tgtatgtgtc caacttctca ctgggtgaca gtgggcagcc cgtgcagcgg   1500
gatgtcagtc gtcttgggga ccacctactc tttgcctctg ggaccaggt tttccaggta   1560
cctatccaag gccctggctg ccgccacttc ctgacctgtg ggcgttgcct aagggcatgg   1620
catttcatgg gctgtggctg gtgtgggaac atgtgcggcc agcagaagga gtgtcctggc   1680
tcctggcaac aggaccactg cccacctaag cttactgagt tccaccccca cagtggacct   1740
ctaaggggca gtacaaggct gaccctgtgt ggctccaact tctaccttca cccttctggt   1800
ctggtgcctg agggaaccca tcaggtcact gtgggccaaa gtccctgccg ccactgccc    1860
aaggacagct caaaactcag gtacaatctg gtccctcccc tcccttttcc tgaaggggga   1920
aaccaagcag ccccttcccc atga                                          1944

<210> SEQ ID NO 19
<211> LENGTH: 1488
<212> TYPE: DNA
<213> ORGANISM: homo sapien

<400> SEQUENCE: 19
atggagctcc tcccgccgct gcctcagtcc ttcctgttgc tgctgctgtt gcctgccaag     60
cccgcggcgg cgaggactg gcagtgcccg cgcaccccct acgcggcctc tcgcgacttt    120
gacgtgaagt acgtggtgcc cagcttctcc gccggaggcc tggtacaggc catggtgacc    180
tacgagggcg acagaaatga gagtgctgtg tttgtagcca tacgcaatcg cctgcatgtg    240
cttgggcctg acctgaagtc tgtccagagc ctggccacgg gccctgctgg agaccctggc    300
tgccagacgt gtcagcctg tggcccagga ccccacggcc ctcccggtga cacagacaca    360
aaggtgctgg tgctggatcc cgcgctgcct gcgctggtca gttgtggctc cagcctgcag    420
ggccgctgct tcctgcatga cctagagccc aagggacag ccgtgcatct ggcagcgcca    480
gcctgcctct tctcagccca ccataaccgg cccgatgact gccccgactg tgtggccagc    540
ccattgggca cccgtgtaac tgtggttgag caaggccagg cctcctattt ctacgtggca    600
tcctcactgg acgcagccgt ggctgccagc ttcagcccac gctcagtgtc tatcaggcgt    660
ctcaaggctg acgcctcggg attcgcaccg ggctttgtgg cgttgtcagt gctgcccaag    720
catcttgtct cctacagtat tgaatacgtg cacagcttcc acacgggagc cttcgtatac    780
ttcctgactg tacagccggc cagcgtgaca gatgatccta gtgccctgca cacacgcctg    840
```

| | | |
|---|---|---|
| gcacggctta gcgccactga gccagagttg ggtgactatc gggagctggt cctcgactgc | 900 |
| agatttgctc caaaacgcag gcgccggggg gccccagaag gcggacagcc ctaccctgtg | 960 |
| ctgcgggtgg cccactccgc tccagtgggt gcccaacttg ccactgagct gagcatcgcc | 1020 |
| gagggccagg aagtactatt tggggtcttt gtgactggca aggatggtgg tcctggcgtg | 1080 |
| ggccccaact ctgtcgtctg tgccttcccc attgacctgc tggacacact aattgatgag | 1140 |
| ggtgtggagc gctgttgtga atccccagtc catccaggcc tccggcgagg cctcgacttc | 1200 |
| ttccagtcgc ccagtttttg ccccaacccg cctggcctgg aagccctcag ccccaacacc | 1260 |
| agctgccgcc acttccctct gctggtcagt agcagcttct cacgtgtgga cctattcaat | 1320 |
| gggctgttgg gaccagtaca ggtcactgca ttgtatgtga cacgccttga caacgtcaca | 1380 |
| gtggcacaca tgggcacaat ggatgggcgt atcctgcagg tgggtcctca tccccacagt | 1440 |
| cccctagccc tgggtccttg tctccatccc cattttgctc acatctga | 1488 |

<210> SEQ ID NO 20
<211> LENGTH: 1294
<212> TYPE: PRT
<213> ORGANISM: homo sapien

<400> SEQUENCE: 20

Met Glu Leu Leu Pro Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
                20                  25                  30

Pro Tyr Ala Ala Ser Arg Asp Phe Asp Val Lys Tyr Val Val Pro Ser
            35                  40                  45

Phe Ser Ala Gly Gly Leu Val Gln Ala Met Val Thr Tyr Glu Gly Asp
        50                  55                  60

Arg Asn Glu Ser Ala Val Phe Val Ala Ile Arg Asn Arg Leu His Val
65              70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp

```
            260                 265                 270
Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
        290                 295                 300

Lys Arg Arg Arg Gly Ala Pro Glu Gly Gln Pro Tyr Pro Val
305                 310                 315                 320

Leu Gln Val Ala His Ser Ala Pro Val Gly Ala Gln Leu Ala Thr Glu
                    325                 330                 335

Leu Ser Ile Ala Glu Gly Gln Glu Val Leu Phe Gly Val Phe Val Thr
                340                 345                 350

Gly Lys Asp Gly Gly Pro Gly Val Gly Pro Asn Ser Val Val Cys Ala
                355                 360                 365

Phe Pro Ile Asp Leu Leu Asp Thr Leu Ile Asp Glu Gly Val Glu Arg
            370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Val Phe Gln Val Pro Ile
                    405                 410                 415

Gln Gly Pro Gly Cys Arg His Phe Leu Thr Cys Gly Arg Cys Leu Arg
                420                 425                 430

Ala Trp His Phe Met Gly Cys Gly Trp Cys Gly Asn Met Cys Gly Gln
                435                 440                 445

Gln Lys Glu Cys Pro Gly Ser Trp Gln Gln Asp His Cys Pro Pro Lys
        450                 455                 460

Leu Thr Glu Phe His Pro His Ser Gly Pro Leu Arg Gly Ser Thr Arg
465                 470                 475                 480

Leu Thr Leu Cys Gly Ser Asn Phe Tyr Leu His Pro Ser Gly Leu Val
                    485                 490                 495

Pro Glu Gly Thr His Gln Val Thr Val Gly Gln Ser Pro Cys Arg Pro
                500                 505                 510

Leu Pro Lys Asp Ser Ser Lys Leu Arg Pro Val Pro Arg Lys Asp Phe
            515                 520                 525

Val Glu Glu Phe Glu Cys Glu Leu Glu Pro Leu Gly Thr Gln Ala Val
        530                 535                 540

Gly Pro Thr Asn Val Ser Leu Thr Val Thr Asn Met Pro Pro Gly Lys
545                 550                 555                 560

His Phe Arg Val Asp Gly Thr Ser Val Leu Arg Gly Phe Ser Phe Met
                    565                 570                 575

Glu Pro Val Leu Ile Ala Val Gln Pro Leu Phe Gly Pro Arg Ala Gly
                580                 585                 590

Gly Thr Cys Leu Thr Leu Glu Gly Gln Ser Leu Ser Val Gly Thr Ser
                595                 600                 605

Arg Ala Val Leu Val Asn Gly Thr Glu Cys Leu Leu Ala Arg Val Ser
            610                 615                 620

Glu Gly Gln Leu Leu Cys Ala Thr Pro Pro Gly Ala Thr Val Ala Ser
625                 630                 635                 640

Val Pro Leu Ser Leu Gln Val Gly Gly Ala Gln Val Pro Gly Ser Trp
                    645                 650                 655

Thr Phe Gln Tyr Arg Glu Asp Pro Val Val Leu Ser Ile Ser Pro Asn
                660                 665                 670

Cys Gly Tyr Ile Asn Ser His Ile Thr Ile Cys Gly Gln His Leu Thr
                675                 680                 685
```

```
Ser Ala Trp His Leu Val Leu Ser Phe His Asp Gly Leu Arg Ala Val
690                 695                 700
Glu Ser Arg Cys Glu Arg Gln Leu Pro Glu Gln Gln Leu Cys Arg Leu
705                 710                 715                 720
Pro Glu Tyr Val Val Arg Asp Pro Gln Gly Trp Val Ala Gly Asn Leu
                725                 730                 735
Ser Ala Arg Gly Asp Gly Ala Ala Gly Phe Thr Leu Pro Gly Phe Arg
            740                 745                 750
Phe Leu Pro Pro Pro His Pro Pro Ser Ala Asn Leu Val Pro Leu Lys
        755                 760                 765
Pro Glu Glu His Ala Ile Lys Phe Glu Tyr Ile Gly Leu Gly Ala Val
770                 775                 780
Ala Asp Cys Val Gly Ile Asn Val Thr Val Gly Gly Glu Ser Cys Gln
785                 790                 795                 800
His Glu Phe Arg Gly Asp Met Val Val Cys Pro Leu Pro Pro Ser Leu
                805                 810                 815
Gln Leu Gly Gln Asp Gly Ala Pro Leu Gln Val Cys Val Asp Gly Glu
            820                 825                 830
Cys His Ile Leu Gly Arg Val Val Arg Pro Gly Pro Asp Gly Val Pro
        835                 840                 845
Gln Ser Thr Leu Leu Gly Ile Leu Leu Pro Leu Leu Leu Leu Val Ala
850                 855                 860
Ala Leu Ala Thr Ala Leu Val Phe Ser Tyr Trp Trp Arg Arg Lys Gln
865                 870                 875                 880
Leu Val Leu Pro Pro Asn Leu Asn Asp Leu Ala Ser Leu Asp Gln Thr
                885                 890                 895
Ala Gly Ala Thr Pro Leu Pro Ile Leu Tyr Ser Gly Ser Asp Tyr Arg
            900                 905                 910
Ser Gly Leu Ala Leu Pro Ala Ile Asp Gly Leu Asp Ser Thr Thr Cys
        915                 920                 925
Val His Gly Ala Ser Phe Ser Asp Ser Glu Asp Glu Ser Cys Val Pro
930                 935                 940
Leu Leu Arg Lys Glu Ser Ile Gln Leu Arg Asp Leu Asp Ser Ala Leu
945                 950                 955                 960
Leu Ala Glu Val Lys Asp Val Leu Ile Pro His Glu Arg Val Val Thr
                965                 970                 975
His Ser Asp Arg Val Ile Gly Lys Gly His Phe Gly Val Val Tyr His
            980                 985                 990
Gly Glu Tyr Ile Asp Gln Ala Gln Asn Arg Ile Gln Cys Ala Ile Lys
        995                 1000                1005
Ser Leu Ser Arg Ile Thr Glu Met Gln Gln Val Glu Ala Phe Leu
    1010                1015                1020
Arg Glu Gly Leu Leu Met Arg Gly Leu Asn His Pro Asn Val Leu
    1025                1030                1035
Ala Leu Ile Gly Ile Met Leu Pro Pro Glu Gly Leu Pro His Val
    1040                1045                1050
Leu Leu Pro Tyr Met Cys His Gly Asp Leu Leu Gln Phe Ile Arg
    1055                1060                1065
Ser Pro Gln Arg Asn Pro Thr Val Lys Asp Leu Ile Ser Phe Gly
    1070                1075                1080
Leu Gln Val Ala Arg Gly Met Glu Tyr Leu Ala Glu Gln Lys Phe
    1085                1090                1095
```

```
Val His Arg Asp Leu Ala Ala Arg Asn Cys Met Leu Asp Glu Ser
    1100                1105                1110

Phe Thr Val Lys Val Ala Asp Phe Gly Leu Ala Arg Asp Ile Leu
    1115                1120                1125

Asp Arg Glu Tyr Tyr Ser Val Gln Gln His Arg His Ala Arg Leu
    1130                1135                1140

Pro Val Lys Trp Met Ala Leu Glu Ser Leu Gln Thr Tyr Arg Phe
    1145                1150                1155

Thr Thr Lys Ser Asp Val Trp Ser Phe Gly Val Leu Leu Trp Glu
    1160                1165                1170

Leu Leu Thr Arg Gly Ala Pro Pro Tyr Arg His Ile Asp Pro Phe
    1175                1180                1185

Asp Leu Thr His Phe Leu Ala Gln Gly Arg Arg Leu Pro Gln Pro
    1190                1195                1200

Glu Tyr Cys Pro Asp Ser Leu Tyr Gln Val Met Gln Gln Cys Trp
    1205                1210                1215

Glu Ala Asp Pro Ala Val Arg Pro Thr Phe Arg Val Leu Val Gly
    1220                1225                1230

Glu Val Glu Gln Ile Val Ser Ala Leu Leu Gly Asp His Tyr Val
    1235                1240                1245

Gln Leu Pro Ala Thr Tyr Met Asn Leu Gly Pro Ser Thr Ser His
    1250                1255                1260

Glu Met Asn Val Arg Pro Glu Gln Pro Gln Phe Ser Pro Met Pro
    1265                1270                1275

Gly Asn Val Arg Arg Pro Arg Pro Leu Ser Glu Pro Pro Arg Pro
    1280                1285                1290

Thr

<210> SEQ ID NO 21
<211> LENGTH: 1400
<212> TYPE: PRT
<213> ORGANISM: homo sapien

<400> SEQUENCE: 21

Met Glu Leu Leu Pro Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
                20                  25                  30

Pro Tyr Ala Ala Ser Arg Asp Phe Asp Val Lys Tyr Val Val Pro Ser
            35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160
```

```
Ala Cys Leu Phe Ser Ala His His Asn Arg Pro Asp Asp Cys Pro Asp
            165                 170                 175

Cys Val Ala Ser Pro Leu Gly Thr Arg Val Thr Val Val Glu Gln Gly
        180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
        290                 295                 300

Lys Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
```

```
                580             585             590
Asn Phe Tyr Leu His Pro Ser Gly Leu Val Pro Glu Gly Thr His Gln
            595                 600             605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
                660                 665                 670

Thr Ser Val Leu Arg Gly Phe Ser Phe Met Glu Pro Val Leu Ile Ala
    675                 680                 685

Val Gln Pro Leu Phe Gly Pro Arg Ala Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
                740                 745                 750

Val Gly Gly Ala Gln Val Pro Gly Ser Trp Thr Phe Gln Tyr Arg Glu
                755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
                820                 825                 830

Asp Pro Gln Gly Trp Val Ala Gly Asn Leu Ser Ala Arg Gly Asp Gly
                835                 840                 845

Ala Ala Gly Phe Thr Leu Pro Gly Phe Arg Phe Leu Pro Pro Pro His
                850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
                900                 905                 910

Met Val Val Cys Pro Leu Pro Ser Leu Gln Leu Gly Gln Asp Gly
                915                 920                 925

Ala Pro Leu Gln Val Cys Val Asp Gly Glu Cys His Ile Leu Gly Arg
                930                 935                 940

Val Val Arg Pro Gly Pro Asp Gly Val Pro Gln Ser Thr Leu Leu Gly
945                 950                 955                 960

Ile Leu Leu Pro Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
                980                 985                 990

Leu Asn Asp Leu Ala Ser Leu Asp Gln Thr Ala Gly Ala Thr Pro Leu
                995                 1000                1005
```

```
Pro Ile Leu Tyr Ser Gly Ser Asp Tyr Arg Ser Gly Leu Ala Leu
    1010            1015            1020

Pro Ala Ile Asp Gly Leu Asp Ser Thr Thr Cys Val His Gly Ala
    1025            1030            1035

Ser Phe Ser Asp Ser Glu Asp Glu Ser Cys Val Pro Leu Leu Arg
    1040            1045            1050

Lys Glu Ser Ile Gln Leu Arg Asp Leu Asp Ser Ala Leu Leu Ala
    1055            1060            1065

Glu Val Lys Asp Val Leu Ile Pro His Glu Arg Val Val Thr His
    1070            1075            1080

Ser Asp Arg Val Ile Gly Lys Gly His Phe Gly Val Val Tyr His
    1085            1090            1095

Gly Glu Tyr Ile Asp Gln Ala Gln Asn Arg Ile Gln Cys Ala Ile
    1100            1105            1110

Lys Ser Leu Ser Arg Ile Thr Glu Met Gln Gln Val Glu Ala Phe
    1115            1120            1125

Leu Arg Glu Gly Leu Leu Met Arg Gly Leu Asn His Pro Asn Val
    1130            1135            1140

Leu Ala Leu Ile Gly Ile Met Leu Pro Pro Glu Gly Leu Pro His
    1145            1150            1155

Val Leu Leu Pro Tyr Met Cys His Gly Asp Leu Leu Gln Phe Ile
    1160            1165            1170

Arg Ser Pro Gln Arg Asn Pro Thr Val Lys Asp Leu Ile Ser Phe
    1175            1180            1185

Gly Leu Gln Val Ala Arg Gly Met Glu Tyr Leu Ala Glu Gln Lys
    1190            1195            1200

Phe Val His Arg Asp Leu Ala Ala Arg Asn Cys Met Leu Asp Glu
    1205            1210            1215

Ser Phe Thr Val Lys Val Ala Asp Phe Gly Leu Ala Arg Asp Ile
    1220            1225            1230

Leu Asp Arg Glu Tyr Tyr Ser Val Gln Gln His Arg His Ala Arg
    1235            1240            1245

Leu Pro Val Lys Trp Met Ala Leu Glu Ser Leu Gln Thr Tyr Arg
    1250            1255            1260

Phe Thr Thr Lys Ser Asp Val Trp Ser Phe Gly Val Leu Leu Trp
    1265            1270            1275

Glu Leu Leu Thr Arg Gly Ala Pro Pro Tyr Arg His Ile Asp Pro
    1280            1285            1290

Phe Asp Leu Thr His Phe Leu Ala Gln Gly Arg Arg Leu Pro Gln
    1295            1300            1305

Pro Glu Tyr Cys Pro Asp Ser Leu Tyr Gln Val Met Gln Gln Cys
    1310            1315            1320

Trp Glu Ala Asp Pro Ala Val Arg Pro Thr Phe Arg Val Leu Val
    1325            1330            1335

Gly Glu Val Glu Gln Ile Val Ser Ala Leu Leu Gly Asp His Tyr
    1340            1345            1350

Val Gln Leu Pro Ala Thr Tyr Met Asn Leu Gly Pro Ser Thr Ser
    1355            1360            1365

His Glu Met Asn Val Arg Pro Glu Gln Pro Gln Phe Ser Pro Met
    1370            1375            1380

Pro Gly Asn Val Arg Arg Pro Arg Pro Leu Ser Glu Pro Pro Arg
    1385            1390            1395
```

-continued

```
Pro Thr
    1400

<210> SEQ ID NO 22
<211> LENGTH: 1080
<212> TYPE: PRT
<213> ORGANISM: homo sapien

<400> SEQUENCE: 22

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Ala Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365
```

-continued

```
Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
                420                 425                 430

Phe Ser Arg Val Asp Leu Phe Asn Gly Leu Leu Gly Pro Val Gln Val
            435                 440                 445

Thr Ala Leu Tyr Val Thr Arg Leu Asp Asn Val Thr Val Ala His Met
        450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
                500                 505                 510

Ser Gly Asp Gln Val Phe Gln Val Pro Ile Gly Pro Gly Cys Arg
            515                 520                 525

His Phe Leu Thr Cys Gly Arg Cys Leu Arg Ala Trp His Phe Met Gly
        530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
                580                 585                 590

Asn Phe Tyr Leu His Pro Ser Gly Leu Val Pro Glu Gly Thr His Gln
                595                 600                 605

Val Thr Val Gly Gln Ser Pro Cys Arg Pro Leu Pro Lys Asp Ser Ser
        610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
                660                 665                 670

Thr Ser Val Leu Arg Gly Phe Ser Phe Met Glu Pro Val Leu Ile Ala
            675                 680                 685

Val Gln Pro Leu Phe Gly Pro Arg Ala Gly Thr Cys Leu Thr Leu
        690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
                740                 745                 750

Val Gly Gly Ala Gln Val Pro Gly Ser Trp Thr Phe Gln Tyr Arg Glu
            755                 760                 765

Asp Pro Val Val Leu Ser Ile Ser Pro Asn Cys Gly Tyr Ile Asn Ser
        770                 775                 780
```

```
His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
            805                 810                 815

Gln Leu Pro Glu Gln Gln Leu Cys Arg Leu Pro Glu Tyr Val Val Arg
        820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro His
    850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Ala Asp Cys Val Gly Ile
                885                 890                 895

Asn Val Thr Val Gly Gly Glu Ser Cys Gln His Glu Phe Arg Gly Asp
                900                 905                 910

Met Val Val Cys Pro Leu Pro Ser Leu Gln Leu Gly Gln Asp Gly
            915                 920                 925

Ala Pro Leu Gln Val Cys Val Asp Gly Glu Cys His Ile Leu Gly Arg
    930                 935                 940

Val Val Arg Pro Gly Pro Asp Gly Val Pro Gln Ser Thr Leu Leu Gly
945                 950                 955                 960

Ile Leu Leu Pro Leu Leu Leu Val Ala Leu Ala Thr Ala Leu
                965                 970                 975

Val Phe Ser Tyr Trp Trp Arg Arg Lys Gln Leu Val Leu Pro Pro Asn
            980                 985                 990

Leu Asn Asp Leu Ala Ser Leu Asp Gln Thr Ala Gly Ala Thr Pro Leu
            995             1000                1005

Pro Ile Leu Tyr Ser Gly Ser Asp Tyr Arg Ser Gly Leu Ala Leu
        1010            1015                1020

Pro Ala Ile Asp Gly Leu Asp Ser Thr Thr Cys Val His Gly Ala
        1025            1030            1035

Ser Phe Ser Asp Ser Glu Asp Glu Ser Cys Val Pro Leu Leu Arg
        1040            1045            1050

Lys Glu Ser Ile Gln Leu Arg Asp Leu Asp Ser Ala Leu Leu Ala
        1055            1060            1065

Glu Val Thr Leu Glu Leu Ser Thr Thr Glu Asn Thr
        1070            1075            1080

<210> SEQ ID NO 23
<211> LENGTH: 254
<212> TYPE: PRT
<213> ORGANISM: homo sapien

<400> SEQUENCE: 23

Met Glu Leu Leu Pro Pro Leu Pro Gln Ser Phe Leu Leu Leu Pro
1               5                   10                  15

Tyr Met Cys His Gly Asp Leu Leu Gln Phe Ile Arg Ser Pro Gln Arg
            20                  25                  30

Asn Pro Thr Val Lys Asp Leu Ile Ser Phe Gly Leu Gln Val Ala Arg
        35                  40                  45

Gly Met Glu Tyr Leu Ala Glu Gln Lys Phe Val His Arg Asp Leu Ala
    50                  55                  60

Ala Arg Asn Cys Met Leu Asp Glu Ser Phe Thr Val Lys Val Ala Asp
65                  70                  75                  80
```

```
Phe Gly Leu Ala Arg Asp Ile Leu Asp Arg Glu Tyr Tyr Ser Val Gln
                85                  90                  95

Gln His Arg His Ala Arg Leu Pro Val Lys Trp Met Ala Leu Glu Ser
            100                 105                 110

Leu Gln Thr Tyr Arg Phe Thr Thr Lys Ser Asp Val Trp Ser Phe Gly
        115                 120                 125

Val Leu Leu Trp Glu Leu Leu Thr Arg Gly Ala Pro Pro Tyr Arg His
    130                 135                 140

Ile Asp Pro Phe Asp Leu Thr His Phe Leu Ala Gln Gly Arg Arg Leu
145                 150                 155                 160

Pro Gln Pro Glu Tyr Cys Pro Asp Ser Leu Tyr Gln Val Met Gln Gln
                165                 170                 175

Cys Trp Glu Ala Asp Pro Ala Val Arg Pro Thr Phe Arg Val Leu Val
            180                 185                 190

Gly Glu Val Glu Gln Ile Val Ser Ala Leu Leu Gly Asp His Tyr Val
        195                 200                 205

Gln Leu Pro Ala Thr Tyr Met Asn Leu Gly Pro Ser Thr Ser His Glu
    210                 215                 220

Met Asn Val Arg Pro Glu Gln Pro Gln Phe Ser Pro Met Pro Gly Asn
225                 230                 235                 240

Val Arg Arg Pro Arg Pro Leu Ser Glu Pro Arg Pro Thr
                245                 250

<210> SEQ ID NO 24
<211> LENGTH: 574
<212> TYPE: PRT
<213> ORGANISM: homo sapien

<400> SEQUENCE: 24

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
```

```
                    195                 200                 205
Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Leu
225                 230                 235                 240

Leu Leu Leu Val Ala Ala Leu Ala Thr Ala Leu Val Phe Ser Tyr Trp
                245                 250                 255

Trp Arg Arg Lys Gln Leu Val Leu Pro Pro Asn Leu Asn Asp Leu Ala
            260                 265                 270

Ser Leu Asp Gln Thr Ala Gly Ala Thr Pro Leu Pro Ile Leu Tyr Ser
        275                 280                 285

Gly Ser Asp Tyr Arg Ser Gly Leu Ala Leu Pro Ala Ile Asp Gly Leu
    290                 295                 300

Asp Ser Thr Thr Cys Val His Gly Ala Ser Phe Ser Asp Ser Glu Asp
305                 310                 315                 320

Glu Ser Cys Val Pro Leu Leu Arg Lys Glu Ser Ile Gln Leu Arg Asp
                325                 330                 335

Leu Asp Ser Ala Leu Leu Ala Glu Val Lys Asp Val Leu Ile Pro His
            340                 345                 350

Glu Arg Val Val Thr His Ser Asp Arg Val Ile Gly Lys Gly His Phe
        355                 360                 365

Gly Val Val Tyr His Gly Glu Tyr Ile Asp Gln Ala Gln Asn Arg Ile
    370                 375                 380

Gln Cys Ala Ile Lys Ser Leu Ser Arg Ile Thr Glu Met Gln Gln Val
385                 390                 395                 400

Glu Ala Phe Leu Arg Glu Gly Leu Leu Met Arg Gly Leu Asn His Pro
                405                 410                 415

Asn Val Leu Ala Leu Ile Gly Ile Met Leu Pro Pro Glu Gly Leu Pro
            420                 425                 430

His Val Leu Leu Pro Tyr Met Cys His Gly Asp Leu Leu Gln Phe Ile
        435                 440                 445

Arg Ser Pro Gln Arg Asn Pro Thr Val Lys Asp Leu Ile Ser Phe Gly
    450                 455                 460

Leu Gln Val Ala Arg Gly Met Glu Tyr Leu Ala Glu Gln Lys Phe Val
465                 470                 475                 480

His Arg Asp Leu Ala Ala Arg Asn Cys Met Tyr Gln Val Met Gln Gln
                485                 490                 495

Cys Trp Glu Ala Asp Pro Ala Val Arg Pro Thr Phe Arg Val Leu Val
            500                 505                 510

Gly Glu Val Glu Gln Ile Val Ser Ala Leu Leu Gly Asp His Tyr Val
        515                 520                 525

Gln Leu Pro Ala Thr Tyr Met Asn Leu Gly Pro Ser Thr Ser His Glu
    530                 535                 540

Met Asn Val Arg Pro Glu Gln Pro Gln Phe Ser Pro Met Pro Gly Asn
545                 550                 555                 560

Val Arg Arg Pro Arg Pro Leu Ser Glu Pro Pro Arg Pro Thr
                565                 570

<210> SEQ ID NO 25
<211> LENGTH: 908
<212> TYPE: PRT
<213> ORGANISM: homo sapien

<400> SEQUENCE: 25
```

-continued

```
Met Glu Leu Leu Pro Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
            115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
            165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
    195                 200                 205

Ala Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
            245                 250                 255

Ala Phe Val Tyr Phe Leu Thr Val Gln Pro Ala Ser Val Thr Asp Asp
        260                 265                 270

Pro Ser Ala Leu His Thr Arg Leu Ala Arg Leu Ser Ala Thr Glu Pro
    275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
            325                 330                 335

Leu Ser Ile Ala Glu Gly Gln Glu Val Leu Phe Gly Val Phe Val Thr
        340                 345                 350

Gly Lys Asp Gly Gly Pro Gly Val Gly Pro Asn Ser Val Val Cys Ala
    355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Gly Leu Glu Ala Leu
        405                 410                 415

Ser Pro Asn Thr Ser Cys Arg His Phe Pro Leu Leu Val Ser Ser Ser
```

-continued

```
                420             425             430
Phe Ser Arg Val Asp Leu Phe Asn Gly Leu Gly Pro Val Gln Val
        435             440             445
Thr Ala Leu Tyr Val Thr Arg Leu Asp Asn Val Thr Val Ala His Met
    450             455             460
Gly Thr Met Asp Gly Arg Ile Leu Gln Val Glu Leu Val Arg Ser Leu
465             470             475             480
Asn Tyr Leu Leu Tyr Val Ser Asn Phe Ser Leu Gly Asp Ser Gly Gln
            485             490             495
Pro Val Gln Arg Asp Val Ser Arg Leu Gly Asp His Leu Leu Phe Ala
        500             505             510
Ser Gly Asp Gln Val Phe Gln Val Pro Ile Gln Gly Pro Gly Cys Arg
        515             520             525
His Phe Leu Thr Cys Gly Arg Cys Leu Arg Ala Trp His Phe Met Gly
        530             535             540
Cys Gly Trp Cys Gly Asn Met Cys Gly Gln Gln Lys Glu Cys Pro Gly
545             550             555             560
Ser Trp Gln Gln Asp His Cys Pro Pro Lys Leu Thr Glu Phe His Pro
            565             570             575
His Ser Gly Pro Leu Arg Gly Ser Thr Arg Leu Thr Leu Cys Gly Ser
        580             585             590
Asn Phe Tyr Leu His Pro Ser Gly Leu Val Pro Glu Gly Thr His Gln
        595             600             605
Val Thr Val Gly Gln Ser Pro Cys Arg Pro Leu Pro Lys Asp Ser Ser
    610             615             620
Lys Leu Arg Pro Val Pro Arg Lys Asp Phe Val Glu Glu Phe Glu Cys
625             630             635             640
Glu Leu Glu Pro Leu Gly Thr Gln Ala Val Gly Pro Thr Asn Val Ser
            645             650             655
Leu Thr Val Thr Asn Met Pro Pro Gly Lys His Phe Arg Val Asp Gly
            660             665             670
Thr Ser Val Leu Arg Gly Phe Ser Phe Met Glu Pro Val Leu Ile Ala
        675             680             685
Val Gln Pro Leu Phe Gly Pro Arg Ala Gly Gly Thr Cys Leu Thr Leu
    690             695             700
Glu Gly Gln Ser Leu Ser Val Gly Thr Ser Arg Ala Val Leu Val Asn
705             710             715             720
Gly Thr Glu Cys Leu Leu Ala Arg Val Ser Glu Gly Gln Leu Leu Cys
            725             730             735
Ala Thr Pro Pro Gly Ala Thr Val Ala Ser Val Pro Leu Ser Leu Gln
            740             745             750
Val Gly Gly Ala Gln Val Pro Gly Ser Trp Thr Phe Gln Tyr Arg Glu
        755             760             765
Asp Pro Val Val Leu Ser Ile Ser Pro Asn Cys Gly Tyr Ile Asn Ser
        770             775             780
His Ile Thr Ile Cys Gly Gln His Leu Thr Ser Ala Trp His Leu Val
785             790             795             800
Leu Ser Phe His Asp Gly Leu Arg Ala Val Glu Ser Arg Gln Cys Glu
            805             810             815
Arg Gln Leu Pro Glu Gln Gln Leu Cys Arg Leu Pro Glu Tyr Val Val
        820             825             830
Arg Asp Pro Gln Gly Trp Val Ala Gly Asn Leu Ser Ala Arg Gly Asp
        835             840             845
```

```
Gly Ala Ala Gly Phe Thr Leu Pro Gly Phe Arg Phe Leu Pro Pro
    850             855                 860

His Pro Pro Ser Ala Asn Leu Val Pro Leu Lys Pro Glu Glu His Ala
865                 870                 875                 880

Ile Lys Phe Glu Val Ser Val Arg Asp Arg Gly Arg Asp Ser Trp Gly
                885                 890                 895

Ser Glu Ser Arg Gly Gln Pro Thr Gly Trp Ser Ser
            900                 905

<210> SEQ ID NO 26
<211> LENGTH: 541
<212> TYPE: PRT
<213> ORGANISM: homo sapien

<400> SEQUENCE: 26

Met Glu Leu Leu Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
                20                  25                  30

Pro Tyr Ala Ala Ser Arg Asp Phe Asp Val Lys Tyr Val Val Pro Ser
                35                  40                  45

Phe Ser Ala Gly Gly Leu Val Gln Ala Met Val Thr Tyr Glu Gly Asp
50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
                100                 105                 110

Gly Pro Pro Gly Asp Thr Asp Thr Lys Val Leu Val Leu Asp Pro Ala
                115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
                180                 185                 190

Gln Ala Ser Tyr Phe Tyr Val Ala Ser Ser Leu Asp Ala Ala Val Ala
            195                 200                 205

Ala Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
                260                 265                 270

Pro Ser Ala Leu His Thr Arg Leu Ala Arg Leu Ser Ala Thr Glu Pro
            275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
```

```
                305                 310                 315                 320
Leu Arg Val Ala His Ser Ala Pro Val Gly Ala Gln Leu Ala Thr Glu
                    325                 330                 335

Leu Ser Ile Ala Glu Gly Gln Glu Val Leu Phe Gly Val Phe Val Thr
                    340                 345                 350

Gly Lys Asp Gly Gly Pro Gly Val Gly Pro Asn Ser Val Val Cys Ala
                    355                 360                 365

Phe Pro Ile Asp Leu Leu Asp Thr Leu Ile Asp Glu Gly Val Glu Arg
                    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Val Phe Gln Val Pro Ile
                    405                 410                 415

Gln Gly Pro Gly Cys Arg His Phe Leu Thr Cys Gly Arg Cys Leu Arg
                    420                 425                 430

Ala Trp His Phe Met Gly Cys Gly Trp Cys Gly Asn Met Cys Gly Gln
                    435                 440                 445

Gln Lys Glu Cys Pro Gly Ser Trp Gln Gln Asp His Cys Pro Pro Lys
                    450                 455                 460

Leu Thr Glu Phe His Pro His Ser Gly Pro Leu Arg Gly Ser Thr Arg
465                 470                 475                 480

Leu Thr Leu Cys Gly Ser Asn Phe Tyr Leu His Pro Ser Gly Leu Val
                    485                 490                 495

Pro Glu Gly Thr His Gln Val Thr Val Gly Gln Ser Pro Cys Arg Pro
                    500                 505                 510

Leu Pro Lys Asp Ser Ser Lys Leu Arg Tyr Asn Leu Val Pro Pro Leu
                    515                 520                 525

Pro Phe Pro Glu Gly Gly Asn Gln Ala Ala Pro Ser Pro
                    530                 535                 540

<210> SEQ ID NO 27
<211> LENGTH: 647
<212> TYPE: PRT
<213> ORGANISM: homo sapien

<400> SEQUENCE: 27

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
                20                  25                  30

Pro Tyr Ala Ala Ser Arg Asp Phe Asp Val Lys Tyr Val Val Pro Ser
                35                  40                  45

Phe Ser Ala Gly Gly Leu Val Gln Ala Met Val Thr Tyr Glu Gly Asp
                50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
                100                 105                 110

Gly Pro Pro Gly Asp Thr Asp Thr Lys Val Leu Val Leu Asp Pro Ala
                115                 120                 125

Leu Pro Ala Leu Val Ser Cys Gly Ser Ser Leu Gln Gly Arg Cys Phe
                130                 135                 140
```

-continued

```
Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
            165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
            195                 200                 205

Ala Ser Phe Ser Pro Arg Ser Val Ser Ile Arg Arg Leu Lys Ala Asp
            210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
            245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
            275                 280                 285

Glu Leu Gly Asp Tyr Arg Glu Leu Val Leu Asp Cys Arg Phe Ala Pro
290                 295                 300

Lys Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
            325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
            355                 360                 365

Phe Pro Ile Asp Leu Leu Asp Thr Leu Ile Asp Glu Gly Val Glu Arg
            370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
            405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
            435                 440                 445

Thr Ala Leu Tyr Val Thr Arg Leu Asp Asn Val Thr Val Ala His Met
450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
            485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Gln Gly Pro Gly Cys Arg
            515                 520                 525

His Phe Leu Thr Cys Gly Arg Cys Leu Arg Ala Trp His Phe Met Gly
            530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
```

```
                     565                 570                 575
His Ser Gly Pro Leu Arg Gly Ser Thr Arg Leu Thr Leu Cys Gly Ser
                580                 585                 590

Asn Phe Tyr Leu His Pro Ser Gly Leu Val Pro Glu Gly Thr His Gln
            595                 600                 605

Val Thr Val Gly Gln Ser Pro Cys Arg Pro Leu Pro Lys Asp Ser Ser
        610                 615                 620

Lys Leu Arg Tyr Asn Leu Val Pro Pro Leu Pro Phe Pro Glu Gly Gly
625                 630                 635                 640

Asn Gln Ala Ala Pro Ser Pro
                645

<210> SEQ ID NO 28
<211> LENGTH: 495
<212> TYPE: PRT
<213> ORGANISM: homo sapien

<400> SEQUENCE: 28

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Ala Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285
```

```
Glu Leu Gly Asp Tyr Arg Glu Leu Val Leu Asp Cys Arg Phe Ala Pro
    290                 295                 300

Lys Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
                340                 345                 350

Gly Lys Asp Gly Gly Pro Gly Val Gly Pro Asn Ser Val Val Cys Ala
                355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
                420                 425                 430

Phe Ser Arg Val Asp Leu Phe Asn Gly Leu Leu Gly Pro Val Gln Val
                435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Gly Pro His Pro His Ser
465                 470                 475                 480

Pro Leu Ala Leu Gly Pro Cys Leu His Pro His Phe Ala His Ile
                485                 490                 495

<210> SEQ ID NO 29
<211> LENGTH: 5107
<212> TYPE: DNA
<213> ORGANISM: homo sapien

<400> SEQUENCE: 29
gaagctgggg caagtaattt tccccaattt acagggaaaa accgaaattc agaaaagttt      60
aatgtcaccc aggggctgga gcccagacct ctggcagctc tcactttcac aatgcccttg     120
ggctgactag gctgcagagg ggtttcaccc aaccccaggg cacctcaag tgtccccacc      180 aaaccttcct aacacctgtc cactaagctg tactaggccc ttgcaactga cctatgggac     240
ctgaggcctg gccctcatg gctcctgtca ccaggtctca ggtcagggtc cagcaggccc     300
tgagctgacg tgtggagcca gagccaccca atcccgtagg acaggtttc acaacttccc      360 ggatggggct gtggtgggtc acagtgcagc ctccagccag aaggatgggg tggctcccac     420
tcctgctgct tctgactcaa tgcttagggg tccctggtaa gtgccccaa ccctgatccc      480 catctgcctt caggaggggg ttggccccat tctcctattc taggatgaga aaaagtcgg     540 ggagccagag gctcagtggg catgggcag tgaccttgcc ctcttgagca cagctgggaa      600
gccctaggaa cacatagaca ttgcccactt aggcctctat tagcacgtct gctctagcac     660
tgaagcagtg tcaggaccac acagatgcac gcacacagca ggcagtgacc cctcctgagc     720
ctgatctacc cctctaacct agcatatgcc tttgtgcagg tgagaccca gatttggagt      780 ctgaatgcct agccagggcc cctggctggg taatgtgatg gctctgagcc ttagcattct     840
catttgagag atgaggtggg gcaagcttca tcacccactg ctctcacaga gcgtatgtgt     900
tagatctgag cccggtgcct gggccactaa acagaggcac cggtgataac taccaagtct     960
```

-continued

```
gggcctgctt cccaggggaa attttttttca caagtatctg tgcaggggc tagactggcc    1020
cttgaaagtg catacagggt ccatcccaga agccttgtag cttttgatccc ctgaatgaac    1080
aaagtgtgga catgccaata cacattactg acatgtatgc ccacctgacc tgcacccact    1140
catgcctact ctgcagggca cgcgctcgcca ttgaatgact tccaagtgct ccggggcaca    1200
gagctacagc acctgctaca tgcggtggtg cccgggcctt ggcaggagga tgtggcagat    1260
gctgaagagt gtgctggtcg ctgtgggccc ttaatggact gccggtgagt ggccactggg    1320
cctagataag actgggggca gggaagcctg ggctgtggcg ttaccctgtg ccttcttctc    1380
tccagggcct tccactacaa cgtgagcagc catggttgcc aactgctgcc atggactcaa    1440
cactcgcccc acacgaggct gcggcgttct gggcgctgtg acctcttcca gaagaaaggc    1500
aagtgggggt ggagagggc agggtgggag cagggggacc tcagcccaag ttgatcttct    1560
gtctcttgct cccagactac gtacggacct gcatcatgaa caatgggggtt gggtaccggg    1620
gcaccatggc cacgaccgtg ggtggcctgc cctgccaggc ttggagccac aagttcccaa    1680
atgatcacaa gtgagacaaa caccttccct ccgtcccggc ctgggggcctt cccccagcac    1740
acactatagt gatgctctgg gccctcaggt acacgcccac tctccggaat ggcctggaag    1800
agaacttctg ccgtaacccct gatggcgacc ccggaggtcc ttggtgctac acaacagacc    1860
ctgctgtgcg cttccagagc tgcggcatca atcctgccg ggagggtaag cggcgccggg    1920
tcaagctggg agagtggagg acaagcccca cgtccatcca cgaacccact ggctctttgt    1980
ctccagccgc gtgtgtctgg tgcaatggcg aggaataccg cggcgcggta gaccgcacgg    2040
agtcagggcg cgagtgccag cgctgggatc ttcagcaccc gcaccagcac ccttcgagc    2100
cgggcaagta cgcgtaggcg gtatcggcgt cctgggggcc gggctaggga aggtccagga    2160
ctccaggggc agggctccgt gtagggcaat tgggcggggc cagataagcc agagtcccag    2220
ggtcttgttc acgcccccatt accgccccca ggttcctcga ccaaggtctg gacgacaact    2280
attgccggaa tcctgacggc tccgagcggc catggtgcta cactacggat ccgcagatcg    2340
agcgagagtt ctgtgacctc ccccgctgcg gtaggcggcg gggaccaggc ctgggagggt    2400
acctgggaac cttggggagg ggcgtggctt ggccggggag gtaagagggg ctgggcgtga    2460
cctgagagca taccccgtgg agtaccgtac acctgggaaa ggcgggtttg gtcccagccc    2520
cagagggatc tcagctctcg ctcggggccc gacctatctc ggtccatcta agggtccgag    2580
gcacagcccc gccaagaggc cacaactgtc agctgcttcc gcgggaaggg tgagggctac    2640
cggggcacag ccaataccac cactgcgggc gtaccttgcc agcgttggga cgcgcaaatc    2700
ccgcatcagc accgatttac gccagaaaaa tacgcgtgca agtgaggtgg gggggggggg    2760
cgggcgttgg gacgtgctgc tgcgggtgag acgggaggaa ggtagtcacg ggctcaaggc    2820
tggaggctgg cgggctaggg ctgagtggag cgcctgctta gagaccttcg ggagaacttc    2880
tgccggaacc ccgacggctc agaggcgccc tggtgcttca cactgcggcc cggcatgcgc    2940
gcggcctttt gctaccagat ccggcgttgt acagacgacg tgcggcccca gggtgaggcc    3000
caagcttggg ggctacagag ccgggctgga agcctggaac cggagggccg gggcgaggtc    3060
tcggcctgat ggctgcccgc acccgccaca gactgctacc acggcgcagg ggagcagtac    3120
cgcggcacgg tcagcaagac ccgcaagggt gtccagtgcc agcgctggtc cgctgagacg    3180
ccgcacaagc cgcagtgagt ccctggtgct cccggccccg ccaggcgcct aaccctgggg    3240
cggcatgctt tggtgtctgg gaccagagcc tggaaatggt tgagactacc ctgccacgat    3300
tttgctcccg cttccgccta ggttcacgtt tacctccgaa ccgcatgcac aactggagga    3360
```

```
gaacttctgc cggaacccag atggggatag ccatgggccc tggtgctaca cgatggaccc   3420
aaggacccca ttcgactact gtgccctgcg acgctgcggt gagcactagt gacgcttccc   3480
ccatgaccct gcctcagccc ccacccaaag gctggctccc ttaacccag tgaactttgt    3540 cttcagctg atgaccagcc gccatcaatc ctggaccccc caggttagga gttgggccag   3600
ttatgggtca ggccctttag cccacgacat ccacacagtc tgggtttcat ccagcccacc   3660
ccatcctaca gaccaggtgc agtttgagaa gtgtggcaag agggtggatc ggctggatca   3720
gcggcgttcc aagctgcgcg tggttggggg ccatccgggc aactcaccct ggacagtcag   3780
cttgcggaat cggtgaggca caactgcctg tctcccacag agaggagctg aggttgtgtc   3840
ctctgtggtt atcccactgg gggctgggaa tctatccctg cccccagagg tcctagccag   3900
aagatggcag gtctagcatc tgtcccagga gtctgttacc tgtcctaatt ccccactcct   3960
ctaggcaggg ccagcatttc tgcgggggt ctctagtgaa ggagcagtgg atactgactg    4020
cccggcagtg cttctcctcc tggtgagcct cccttgtgtt tggggaccca gtctcatccc   4080
accttccccc ttccccaggc aagctaacaa gtgagccttg gggcaatgga ctgagagtca   4140
caaatgacct agcagagctt ctctcccagc catatgcctc tcacgggcta tgaggtatgg   4200
ttgggcaccc tgttccagaa cccacagcat ggagagccaa gcctacagcg ggtcccagta   4260
gccaagatgg tgtgtgggcc ctcaggctcc cagcttgtcc tgctcaagct ggagaggtat   4320
gtggacaacc tgggagggtg tgaggtgggg ctgggccttg tggcctcaga ccctgagtgc   4380
ccccattctt gctaaagatc tgtgaccctg aaccagcgtg tggccctgat ctgcctgccc   4440
cctgaatggt atgtggtgcc tccagggacc aagtgtgaga ttgcaggctg gggtgagacc   4500
aaaggtaaga gcacagtgca caggactgct ggtggccagg aggcccagcc ctggatcttc   4560
ctgcaggacc ctctccctct ccccattccc ctcactgcag gtacgggtaa tgacacagtc   4620
ctaaatgtgg ccttgctgaa tgtcatctcc aaccaggagt gtaacatcaa gcaccgagga   4680
cgtgtgcggg agagtgagat gtgcactgag ggactgttgg cccctgtggg ggcctgtgag   4740
gttggtggca gggccctggg ccagccctgg aagggtatgg ggggctagaa atgaactatt   4800
ttatcatgaa gcaggctagt cattgctgtg cccggggcc ctcatcagtt ctcctacctg     4860
ccagggtgac tacggggggcc cacttgcctg ctttaccccac aactgctggg tcctggaagg   4920
aattataatc cccaaccgag tatgcgcaag gtcccgctgg ccagctgtct tcacgcgtgt   4980
ctctgtgttt gtggactgga ttcacaaggt catgagactg ggttaggccc agccttgatg   5040
ccatatgcct tggggaggac aaaacttctt gtcagacata aagccatgtt tcctcttat    5100 gcctgta                                                              5107
```

<210> SEQ ID NO 30
<211> LENGTH: 5107
<212> TYPE: DNA
<213> ORGANISM: homo sapien

<400> SEQUENCE: 30

```
gaagctgggg caagtaattt tccccaattt acagggaaaa accgaaattc agaaaagttt    60
aatgtcaccc aggggctgga gcccagacct ctggcagctc tcactttcac aatgcccttg   120
ggctgactag gctgcagagg ggtttcaccc caaccccagg gcacctcaag tgtccccacc   180
aaaccttcct aacacctgtc cactaagctg tactaggccc ttgcaactga cctatgggac   240
ctgaggcctg gcccctcatg gctcctgtca ccaggtctca ggtcagggtc cagcaggccc   300
```

```
tgagctgacg tgtggagcca gagccaccca atcccgtagg gacaggtttc acaacttccc    360
ggatggggct gtggtgggtc acagtgcagc ctccagccag aaggatgggg tggctcccac    420
tcctgctgct tctgactcaa tgcttagggg tccctggtaa gtgcccccaa ccctgatccc    480
catctgcctt caggaggggg ttggccccat tctcctattc taggatgaga aaaaagtcgg    540
ggagccagag gctcagtggg catggggcag tgaccttgcc ctcttgagca cagctgggaa    600
gccctaggaa cacatagaca ttgcccactt aggcctctat tagcacgtct gctctagcac    660
tgaagcagtg tcaggaccac acagatgcac gcacacagca ggcagtgacc cctcctgagc    720
ctgatctacc cctctaacct agcatatgcc tttgtgcagg tgagagccca gatttggagt    780
ctgaatgcct agccagggcc cctggctggg taatgtgatg gctctgagcc ttagcattct    840
catttgagag atgaggtggg gcaagcttca tcacccactg ctctcacaga gcgtatgtgt    900
tagatctgag cccggtgcct gggccactaa acagaggcac cggtgataac taccaagtct    960
gggcctgctt cccaggggaa attttttttca caagtatctg tgcaggggc tagactggcc    1020 cttgaaagtg catacagggt ccatcccaga agccttgtag ctttgatccc ctgaatgaac    1080
aaagtgtgga catgccaata cacattactg acatgtatgc ccacctgacc tgcacccact    1140
catgcctact ctgcagggca gcgctcgcca ttgaatgact tccaagtgct ccggggcaca    1200
gagctacagc acctgctaca tgcggtggtg cccgggcctt ggcaggagga tgtggcagat    1260
gctgaagagt gtgctggtcg ctgtgggccc ttaatggact gccggtgagt ggccactggg    1320
cctagataag actgggggca gggaagcctg ggctgtggcg ttaccctgtg ccttcttctc    1380
tccagggcct tccactacaa cgtgagcagc catggttgcc aactgctgcc atggactcaa    1440
cactcgcccc acacgaggct gcggcgttct gggcgctgtg acctcttcca gaagaaaggc    1500
aagtgggggt ggagaggggc agggtgggag acagggggacc tcagcccaag ttgatcttct    1560
gtctcttgct cccagactac gtacggacct gcatcatgaa caatggggtt gggtaccggg    1620
gcaccatggc cacgaccgtg ggtggcctgc cctgccaggc ttggagccac aagttcccaa    1680
atgatcacaa gtgagacaaa caccttccct ccgtcccggc ctggggcctt cccccagcac    1740
acactatagt gatgctctgg gccctcaggt acacgcccac tctccggaat ggcctggaag    1800
agaacttctg ccgtaacccct gatggcgacc ccggaggtcc ttggtgctac acaacagacc    1860
ctgctgtgcg cttccagagc tgcggcatca atcctgccg ggagggtaag cggcgccggg    1920
tcaagctggg agagtggagg acaagcccca cgtccatcca cgaacccact ggctctttgt    1980
ctccagccgc gtgtgtctgg tgcaatggcg aggaatacccg cggcgcggta gaccgcacgg    2040
agtcagggcg cgagtgccag cgctgggatc ttcagcaccc gcaccagcac cccttcgagc    2100
cgggcaagta cgcgtaggcg gtatcggcgt cctgggggcc gggctaggga aggtccagga    2160
ctccaggggc agggctccgt gtagggcaat tgggcggggc cagataagcc agagtcccag    2220
ggtcttgttc acgccccatt accgccccca ggttcctcga ccaaggtctg gacgacaact    2280
attgccggaa tcctgacggc tccgagcggc catggtgcta cactacggat ccgcagatcg    2340
agcgagagtt ctgtgaccct cccgctgcg gtaggcggcg gggaccaggc ctgggagggt    2400
acctgggaac cttggggagg ggcgtggctt ggccggggag gtaagagggg ctgggcgtga    2460
cctgagagca taccccgtgg agtaccgtac acctgggaaa ggcgggtttg gtcccagccc    2520
cagagggatc tcagctctcg ctcggggccc gacctatctc ggtccatcta agggtccgag    2580
gcacagcccc gccaagaggc cacaactgtc agctgcttcc gcgggaaggg tgagggctac    2640
cggggcacag ccaataccac cactgcgggc gtaccttgcc agcgttggga cgcgcaaatc    2700
```

```
ccgcatcagc accgatttac gccagaaaaa tacgcgtgca agtgaggtgg ggggggggg    2760 cgggcgttgg gacgtgctgc tgcgggtgag acgggaggaa ggtagtcacg ggctcaaggc    2820
tggaggctgg cgggctaggg ctgagtggag cgcctgctta gagaccttcg ggagaacttc    2880
tgccggaacc ccgacggctc agaggcgccc tggtgcttca cactgcggcc cggcatgcgc    2940
gcggcctttt gctaccagat ccggcgttgt acagacgacg tgcggcccca gggtgaggcc    3000
caagcttggg ggctacagag ccgggctgga agcctgaaac cggagggccg gggcgaggtc    3060
tcggcctgat ggctgcccgc acccgccaca gactgctacc acggcgcagg ggagcagtac    3120
cgcggcacgg tcagcaagac ccgcaagggt gtccagtgcc agcgctggtc cgctgagacg    3180
ccgcacaagc cgcagtgagt ccctggtgct cccggccccg ccagggccct aaccctgggg    3240
cggcatgctt tggtgtctgg gaccagagcc tggaaatggt tgagactacc ctgccacgat    3300
tttgctcccg cttccgccta ggttcacgtt tacctccgaa ccgcatgcac aactgggagga   3360 gaacttctgc cggaacccag atggggatag ccatgggccc tggtgctaca cgatggaccc    3420
aaggacccca ttcgactact gtgccctgcg acgctgcggt gagcactagt gacgcttccc    3480 ccatgacect gcctcagccc ccacccaaag gctggctccc ttaacccag tgaactttgt     3540 cttcagctg atgaccagcc gccatcaatc ctggaccccc caggttagga gttgggccag     3600
ttatgggtca ggccctttag cccacgacat ccacacagtc tgggtttcat ccagcccacc    3660
ccatcctaca gaccaggtgc agtttgagaa gtgtggcaag agggtggatc ggctggatca    3720
gcggcgttcc aagctgcgcg tggttggggg ccatccgggc aactcaccct ggacagtcag    3780
cttgcggaat cggtgaggca caactgcctg tctcccacag agaggagctg aggttgtgtc    3840
ctctgtggtt atcccactgg gggctgggaa tctatccctg cccccagagg tcctagccag    3900
aagatggcag gtctagcatc tgtcccagga gtctgttacc tgtcctaatt ccccactcct    3960
ctaggcaggg ccagcatttc tgcgggggt ctctagtgaa ggagcagtgg atactgactg     4020
cccggcagtg cttctcctcc tggtgagcct cccttgtgtt tggggaccca gtctcatccc    4080
accttccccc ttccccaggc aagctaacaa gtgagccttg gggcaatgga ctgagagtca    4140
caaatgacct agcagagctt ctctcccagc catatgcctc tcacgggcta tgaggtatgg    4200
ttgggcaccc tgttccagaa cccacagcat ggagagccaa gcctacagcg ggtcccagta    4260
gccaagatgg tgtgtgggcc ctcaggctcc cagcttgtcc tgctcaagct ggagaggtat    4320
gtggacaacc tgggagggtg tgaggtgggg ctgggccttg tggcctcaga ccctgagtgc    4380
ccccattctt gctaaagatc tgtgaccctg aaccagcgtg tggccctgat ctgcctgccc    4440
cctgaatggt atgtggtgcc tccagggacc aagtgtgaga ttgcaggctg gggtgagacc    4500
aaaggtaaga gcacagtgca caggactgct ggtggcagg aggcccagcc ctggatcttc     4560
ctgcaggacc ctctccctct ccccattccc ctcactgcag gtacgggtaa tgacacagtc    4620
ctaaatgtgg ccttgctgaa tgtcatctcc aaccaggagt gtaacatcaa gcaccgagga    4680
cgtgtgcggg agagtgagat gtgcactgag ggactgttgg cccctgtggg ggcctgtgag    4740
gttggtggca gggccctggg ccagccctgg aagggtatgg ggggctagaa atgaactatt    4800
ttatcatgaa gcaggctagt cattgctgtg gcccggggcc ctcatcagtt ctcctacctg    4860
ccagggtgac tacgggggcc cacttgcctg ctttaccac aactgctggg tcctggaagg     4920
aattataatc cccaaccgag tatgcgcaag gtcctgctgg ccagctgtct tcacgcgtgt    4980
ctctgtgttt gtggactgga ttcacaaggt catgagactg ggttaggccc agccttgatg    5040
```

```
ccatatgcct tggggaggac aaaacttctt gtcagacata aagccatgtt tcctctttat    5100
gcctgta                                                              5107

<210> SEQ ID NO 31
<211> LENGTH: 2621
<212> TYPE: DNA
<213> ORGANISM: homo sapien

<400> SEQUENCE: 31
gaagcugggg caaguaauuu uccccaauuu acagggaaaa accgaaauuc agaaaaguuu      60
aaugucaccc aggggcugga gcccagaccu cuggcagcuc ucacuuucac aaugcccuug     120
ggcugacuag gcugcagagg gguuucaccc caaccccagg gcaccucaag uguccccacc     180
aaaccuuccu aacaccuguc cacuaagcug uacuaggccc uugcaacuga ccuaugggac     240
cugaggccug gccccucaug gcuccuguca ccaggucuca ggucaggguc cagcaggccc     300
ugagcugacg guggagcca gagccaccca aucccguagg gacagguuuc acaacuuccc      360 ggaugggcu guggugggguc acagugcagc cuccagccag aaggauggggg uggcucccac    420 uccugcugcu ucugacucaa ugcuuagggg ucccgggca gcgcucgcca uugaaugacu      480
uccaagugcc ccggggcaca gagcuacagc accugcuaca ugcgguggug cccgggccuu    540
ggcaggagga guggcagau gcugaagagu gucuggucg cugugggccc uuaauggacu      600
gccgggccuu ccacuacaac gugagcagcc augguugcca acugcugcca uggacucaac    660
acucgcccca cacgaggcug cggcguucug ggcgcuguga ccucuuccag aagaaagacu    720
acguacggac cugcaucaug aacaaugggg uugggguaccg gggcaccaug gccacgaccg    780 ugggugccu gcccugccag gcuuggagcc acaaguuccc aaaugaucac aaguacacgc     840
ccacucuccg gaauggccug gaagagaacu ucugccguaa cccugauggc gaccccggag    900
guccuuggug cuacacaaca gacccugcug ugcgcuucca gagcugcggc aucaaauccu    960
gccgggaggc cgcgugugu cuggugcaaug gcgaggaaua ccgcggcgcg guagaccgca   1020
cggagucagg gcgcgagugc cagcgcuggg aucuucagca cccgcaccag caccccuucg    1080
agccgggcaa guucucgac caaggucugg acgacaacua uugccggaau ccugacggcu    1140
ccgagcggcc augguguuac acuacggauc cgcagaucga gcgagaguuc ugugaccucc    1200
cccgcugcgg guccgaggca cagcccccgcc aagaggccac aacugucagc ugcuuccgcg    1260
ggaaggguga gggcuaccgg ggcacagcca auaccaccac ugcgggcgua ccuugccagc    1320
guugggacgc gcaaauccccg caucagcacc gauuuacgcc agaaaaauac gcgugcaaag    1380
accuucggga gaacuucugc cggaaccccg acggcucaga ggcgcccugg ugcuucacac    1440
ugcggcccgg caugcgcgcg ccuuuugcu accagaucg gcguuguaca gacgacgugc      1500
ggccccagga cugcuaccac ggcgcagggg agcaguaccg cggcacgguc agcaagaccc    1560
gcaagggugu ccagugccag cgcugguccg cugagacgcc gcacaagccg caguucacgu     1620
uuaccuccga accgcaugca caacuggagg agaacuucug ccggaaccca gauggggaua    1680
gccaugggcc cuggugcuac acgauggacc caaggacccc auucgacuac ugugcccugc    1740
gacgcugcgc ugaugaccag ccgccaucaa uccuggaccc cccagaccag gugcaguuug    1800
agaagugugg caagagggug gaucggcugg aucagcggcg uuccaagcug cgcgugguug    1860
ggggccaucc gggcaacuca cccuggacag ucagcuugcg gaaucggcag ggccagcauu    1920
ucugcggggg gucucuagug aaggagcagu ggauacugac ugcccggcag ugcucuccuu    1980
ccugccauau gccucucacg ggcuaugagg uauggugggg cacccuguuc cagaacccac    2040
```

| | |
|---|---|
| agcauggaga gccaagccua cagcgggucc caguagccaa gauggugugu gggcccucag | 2100 |
| gcucccagcu uguccugcuc aagcuggaga gaucugugac ccugaaccag cguguggccc | 2160 |
| ugaucugccu gcccccugaa ugguaugugg ugccuccagg gaccaagugu gagauugcag | 2220 |
| gcugggguga gaccaaaggu acggguaaug acacaguccu aaauguggcc uugcugaaug | 2280 |
| ucaucuccaa ccaggagugu aacaucaagc accgaggacg ugugcgggag agugagaugu | 2340 |
| gcacugaggg acuguuggcc ccugugggg ccugugaggg ugacuacggg ggcccacuug | 2400 |
| ccugcuuuac ccacaacugc uggguccugg aaggaauuau aauccccaac cgaguaugcg | 2460 |
| caaggucccg cuggccagcu ucuucacgc gugucucugu guuguggac uggauucaca | 2520 |
| aggucaugag acugguuag gcccagccuu gaugccauau gccuugggga ggacaaaacu | 2580 |
| ucuugucaga cauaaagcca uguuccucu uuaugccugu a | 2621 |

<210> SEQ ID NO 32
<211> LENGTH: 2621
<212> TYPE: DNA
<213> ORGANISM: homo sapien

<400> SEQUENCE: 32

| | |
|---|---|
| gaagcugggg caaguaauuu uccccaauuu acagggaaaa accgaaauuc agaaaaguuu | 60 |
| aaugucaccc aggggcugga gcccagaccu cuggcagcuc ucacuuucac aaugcccuug | 120 |
| ggcugacuag gcugcagagg gguuucaccc caaccccagg gcaccucaag uguccccacc | 180 |
| aaaccuuccu aacaccugac cacuaagcug uacuaggccc uugcaacuga ccuauggggac | 240 |
| cugaggccug gccccucaug gcuccuguca ccaggucuca ggucagggus cagcaggccc | 300 |
| ugagcugacg uguggagcca gagccaccca aucccguagg gacagguuuc acaacuuccc | 360 |
| ggaugggggcu guggugggggс acagugcagc cuccagccag aaggauggggg uggcucccac | 420 |
| uccugcugcu ucugacucaa ugcuuagggg ucccugggca gcgucgcca uugaaugacu | 480 |
| uccaagugcu ccggggcaca gagcuacagc accgcuaca ugcgguggug cccgggccuu | 540 |
| ggcaggagga uguggcagau gcugaagagu gugcuggucg cuguggggccc uuaauggacu | 600 |
| gccgggccuu ccacuacaac gugagcagcc augguugcca acugcugcca uggacucaac | 660 |
| acucgcccca cacgaggcug cggcguucug ggcgcuguga ccucuuccag aagaaagacu | 720 |
| acguacggac cugcaucaug aacaauggggg uuggguaccg gggcaccaug gccacgaccg | 780 |
| ugggguggccu gcccugccag gcuggagcc acaaguuccc aaaugaucac aaguacacgc | 840 |
| ccacucuccg gaauggccug gaagagaacu cugccguaa cccugauggc gaccccggag | 900 |
| guccuugguug cuacacaaca gacccugcug ugcgcuucca gagcugcggc aucaaauccu | 960 |
| gccgggaggc cgcugugguc uggugcaaug gcgaggaaua ccgcggcgcg guagaccgca | 1020 |
| cggagucagg gcgcgagugc cagcgcuggg aucuucagca cccgcaccag caccccuucg | 1080 |
| agccgggcaa guuccucgac caaggucugg acgacaacua uugccggaau ccugacggcu | 1140 |
| ccgagcggcc auggugcuac acuacggauc cgcagaucga gcgagaguuc ugugaccucc | 1200 |
| cccgcugcgg guccgaggca cagccccgcc aagaggccac aacugucagc ugcuuccgcg | 1260 |
| ggaaggguga gggcuaccgg ggcacagcca auaccaccac ugcgggcgua ccuugccagc | 1320 |
| guugggacgc gcaaaucccg caucagcacc gauuuacgcc agaaaaauac gcgugcaaag | 1380 |
| accuucggga gaacuucugc cggaaccccg acggcucaga ggcgcccugg ugcuucacac | 1440 |
| ugcggcccgg caugcgcgcg gccuuuugcu accagauccg gcguuguaca gacgacgugc | 1500 |

-continued

| | |
|---|---|
| ggccccagga cugcuaccac ggcgcagggg agcaguaccg cggcacgguc agcaagaccc | 1560 |
| gcaagggugu ccagugccag cgcugguccg cugagacgcc gcacaagccg caguucacgu | 1620 |
| uuaccuccga accgcaugca caacuggagg agaacuucug ccggaaccca gaugggaua | 1680 |
| gccaugggcc cuggugcuac acgauggacc caaggacccc auucgacuac ugugcccugc | 1740 |
| gacgcugcgc ugaugaccag ccgccaucaa uccuggaccc cccagaccag gugcaguuug | 1800 |
| agaagugugg caagaggguag gaucggcugg aucagcggcg uuccaagcug cgcgugguug | 1860 |
| ggggccaucc gggcaacuca cccuggacag ucagcuugcg gaaucggcag ggccagcauu | 1920 |
| ucugcggggg gucucuagug aaggagcagu ggauacugac ugcccggcag ugcuucuccu | 1980 |
| ccugccauau gccucucacg ggcuaugagg uaugguuggg cacccuguuc cagaacccac | 2040 |
| agcauggaga gccaagccua cagcgggucc caguagccaa gaugguguagu gggcccucag | 2100 |
| gcucccagcu uguccugcuc aagcuggaga gaucugugac ccugaaccag cgugugggccc | 2160 |
| ugaucgccu gccccugaa ugguaugugg ugccuccagg gaccaagugu gagauugcag | 2220 |
| gcuggggugu gaccaaaggu acggguaaug acacaguccu aaaugguggcc uugcugaaug | 2280 |
| ucaucuccaa ccaggagugu aacaucaagc accgaggacg ugugcgggag agugagaugu | 2340 |
| gcacugaggg acuguuggcc ccugugggggg ccugugaggg ugacuacggg ggcccacuug | 2400 |
| ccugcuuuac ccacaacugc uggguccugg aaggaauuau aaucccaac cgaguaugcg | 2460 |
| caagguccug cuggccagcu gucuucacgc gugucucugu guuugugggac uggauucaca | 2520 |
| aggucaugag acugggguuag gcccagccuu gaugccauau gccuggggga ggacaaaacu | 2580 |
| ucuugucaga cauaaagcca uguuccucu uuaugccugu a | 2621 |

<210> SEQ ID NO 33
<211> LENGTH: 2621
<212> TYPE: DNA
<213> ORGANISM: homo sapien

<400> SEQUENCE: 33

| | |
|---|---|
| gaagctgggg caagtaattt tccccaattt acagggaaaa accgaaattc agaaaagttt | 60 |
| aatgtcaccc aggggctgga gcccagacct ctggcagctc tcactttcac aatgcccttg | 120 |
| ggctgactag gctgcagagg ggtttcaccc caaccccagg gcacctcaag tgtccccacc | 180 |
| aaaccttcct aacacctgtc cactaagctg tactaggccc ttgcaactga cctatgggac | 240 |
| ctgaggcctg gcccctcatg gctcctgtca ccaggtctca ggtcagggtc cagcaggccc | 300 |
| tgagctgacg tgtggagcca gagccaccca atcccgtagg gacaggtttc acaacttccc | 360 |
| ggatggggct gtggtgggtc acagtgcagc ctccagccag aaggatgggg tggctcccac | 420 |
| tcctgctgct tctgactcaa tgcttagggg tccctgggca gcgctcgcca ttgaatgact | 480 |
| tccaagtgct ccggggcaca gagctacagc acctgctaca tgcggtggtg cccgggcctt | 540 |
| ggcaggagga tgtggcagat gctgaagagt gtgctggtcg ctgtgggccc ttaatggact | 600 |
| gccgggcctt ccactacaac gtgagcagcc atggttgcca actgctgcca tggactcaac | 660 |
| actcgcccca cacgaggctg cggcgttctg ggcgctgtga cctcttccag aagaaagact | 720 |
| acgtacggac ctgcatcatg aacaatgggg ttgggtaccg gggcaccatg gccacgaccg | 780 |
| tgggtggcct gccctgccag gcttggagcc acaagttccc aaatgatcac aagtacacgc | 840 |
| ccactctccg gaatgccctg gaagagaact tctgccgtaa ccctgatggc ccccggag | 900 |
| gtccttggtg ctacacaaca gaccctgctg tgcgcttcca gagctgcggc atcaatcct | 960 |
| gccgggaggc cgcgtgtgtc tggtgcaatg gcgaggaata ccgcggcgcg gtagaccgca | 1020 |

```
cggagtcagg gcgcgagtgc cagcgctggg atcttcagca cccgcaccag cacccctcg      1080 agccgggcaa gttcctcgac caaggtctgg acgacaacta ttgccggaat cctgacggct     1140
ccgagcggcc atggtgctac actacggatc cgcagatcga gcgagagttc tgtgacctcc     1200
cccgctgcgg gtccgaggca cagccccgcc aagaggccac aactgtcagc tgcttccgcg     1260
ggaagggtga gggctaccgg ggcacagcca ataccaccac tgcgggcgta ccttgccagc     1320
gttgggacgc gcaaatcccg catcagcacc gatttacgcc agaaaaatac gcgtgcaaag     1380
accttcggga gaacttctgc cggaaccccg acggctcaga ggcgccctgg tgcttcacac     1440 tgcggccccgg catgcgcgcg gcctttgct accagatccg gcgttgtaca gacgacgtgc     1500
ggccccagga ctgctaccac ggcgcagggg agcagtaccg cggcacggtc agcaagaccc     1560
gcaagggtgt ccagtgccag cgctggtccg ctgagacgcc gcacaagccg cagttcacgt     1620
ttacctccga accgcatgca caactggagg agaacttctg ccggaaccca gatgtgggata    1680 gccatgggcc ctggtgctac acgatggacc caaggacccc attcgactac tgtgccctgc     1740
gacgctgcgc tgatgaccag ccgccatcaa tcctggaccc cccagaccag gtgcagtttg     1800
agaagtgtgg caagagggtg gatcggctgg atcagcggcg ttccaagctg cgcgtggttg     1860
ggggccatcc gggcaactca ccctggacag tcagcttgcg gaatcggcag ggccagcatt     1920
tctgcggggg gtctctagtg aaggagcagt ggatactgac tgcccggcag tgcttctcct     1980
cctgccatat gcctctcacg ggctatgagg tatggttggg caccctgttc cagaacccac     2040
agcatggaga gccaagccta cagcgggtcc cagtagccaa gatggtgtgt gggccctcag     2100
gctcccagct tgtcctgctc aagctggaga gatctgtgac cctgaaccag cgtgtggccc     2160
tgatctgcct gcccctgaa tggtatgtgg tgcctccagg gaccaagtgt gagattgcag       2220
gctggggtga gaccaaaggt acgggtaatg acacagtcct aaatgtggcc ttgctgaatg     2280
tcatctccaa ccaggagtgt aacatcaagc accgaggacg tgtgcgggag agtgagatgt     2340
gcactgaggg actgttggcc cctgtggggg cctgtgaggg tgactacggg ggcccacttg     2400
cctgctttac ccacaactgc tgggtcctgg aaggaattat aatccccaac cgagtatgcg     2460
caaggtcccg ctggccagct gtcttcacgc gtgtctctgt gtttgtggac tggattcaca     2520
aggtcatgag actgggttag gcccagcctt gatgccatat gccttgggga ggacaaaact     2580
tcttgtcaga cataaagcca tgtttcctct ttatgcctgt a                          2621
```

<210> SEQ ID NO 34
<211> LENGTH: 2621
<212> TYPE: DNA
<213> ORGANISM: homo sapien

<400> SEQUENCE: 34

```
gaagctgggg caagtaattt tccccaattt acagggaaaa accgaaattc agaaaagttt       60
aatgtcaccc aggggctgga gcccagacct ctggcagctc tcactttcac aatgcccttg      120
ggctgactag gctgcagagg ggtttcaccc caaccccagg gcacctcaag tgtccccacc      180
aaaccttcct aacacctgtc cactaagctg tactaggccc ttgcaactga cctatgggac      240
ctgaggcctg gcccctcatg gctcctgtca ccaggtctca ggtcagggtc cagcaggccc      300
tgagctgacg tgtggagcca gagccaccca atcccgtagg acaggtttc acaacttccc       360 ggatggggct gtggtgggtc acagtgcagc ctccagccag aaggatgggg tggctcccac      420
tcctgctgct tctgactcaa tgcttagggg tccctgggca gcgctcgcca ttgaatgact      480
```

```
tccaagtgct ccggggcaca gagctacagc acctgctaca tgcggtggtg cccgggcctt    540
ggcaggagga tgtggcagat gctgaagagt gtgctggtcg ctgtgggccc ttaatggact    600
gccgggcctt ccactacaac gtgagcagcc atggttgcca actgctgcca tggactcaac    660
actcgcccca cacgaggctg cggcgttctg ggcgctgtga cctcttccag aagaaagact    720
acgtacggac ctgcatcatg aacaatgggg ttgggtaccg gggcaccatg ccacgaccg    780
tgggtggcct gccctgccag gcttggagcc acaagttccc aaatgatcac aagtacacgc    840
ccactctccg gaatggcctg aagagaact tctgccgtaa ccctgatggc gaccccggag    900
gtccttggtg ctacacaaca gaccctgctg tgcgcttcca gagctgcggc atcaaatcct    960
gccgggaggc cgcgtgtgtc tggtgcaatg gcgaggaata ccgcggcgcg gtagaccgca   1020
cggagtcagg gcgcgagtgc cagcgctggg atcttcagca cccgcaccag cacccctccg   1080
agccgggcaa gttcctcgac caaggtctgg acgacaacta ttgccggaat cctgacggct   1140
ccgagcggcc atggtgctac actacgatc cgcagatcga gcgagagttc tgtgacctcc   1200
cccgctgcgg gtccgaggca cagccccgcc aagaggccac aactgtcagc tgcttccgcg   1260
ggaagggtga gggctaccgg ggcacagcca ataccaccac tgcgggcgta ccttgccagc   1320
gttgggacgc gcaaatcccg catcagcacc gatttacgcc agaaaaatac gcgtgcaaag   1380
accttcggga gaacttctgc cggaaccccg acggctcaga ggcgccctgg tgcttcacac   1440
tgcggccccgg catgcgcgcg gccttttgct accagatccg gcgttgtaca gacgacgtgc   1500
ggccccagga ctgctaccac ggcgcagggg agcagtaccg cggcacggtc agcaagaccc   1560
gcaagggtgt ccagtgccag cgctggtccg ctgagacgcc gcacaagccg cagttcacgt   1620
ttacctccga accgcatgca caactggagg agaacttctg ccggaaccca gatggggata   1680
gccatgggcc ctggtgctac acgatggacc caaggacccc attcgactac tgtgccctgc   1740
gacgctgcgc tgatgaccag ccgccatcaa tcctggaccc cccagaccag gtgcagtttg   1800
agaagtgtgg caagagggtg gatcggctgg atcagcggcg ttccaagctg cgcgtggttg   1860
ggggccatcc gggcaactca ccctggacag tcagcttgcg gaatcggcag ggccagcatt   1920
tctgcggggg gtctctagtg aaggagcagt ggatactgac tgcccggcag tgcttctcct   1980
cctgccatat gcctctcacg ggctatgagg tatggttggg caccctgttc cagaacccac   2040
agcatggaga gccaagccta cagcgggtcc cagtagccaa gatggtgtgt gggccctcag   2100
gctcccagct tgtcctgctc aagctggaga gatctgtgac cctgaaccag cgtgtggccc   2160
tgatctgcct gccccctgaa tggtatgtgg tgcctccagg gaccaagtgt gagattgcag   2220
gctggggtga gaccaaaggt acgggtaatg acacagtcct aaatgtggcc ttgctgaatg   2280
tcatctccaa ccaggagtgt aacatcaagc accgaggacg tgtgcgggag agtgagatgt   2340
gcactgaggg actgttggcc cctgtggggg cctgtgaggg tgactacggg ggcccacttg   2400
cctgctttac ccacaactgc tgggtcctgg aaggaattat aatccccaac cgagtatgcg   2460
caaggtcctg ctggccagct gtcttcacgc gtgtctctgt gtttgtggac tggattcaca   2520
aggtcatgag actgggttag gcccagcctt gatgccatat gccttgggga ggacaaaact   2580
tcttgtcaga cataaagcca tgtttcctct ttatgcctgt a                      2621
```

<210> SEQ ID NO 35
<211> LENGTH: 725
<212> TYPE: PRT
<213> ORGANISM: homo sapien

<400> SEQUENCE: 35

-continued

```
Met Gly Leu Trp Trp Val Thr Val Gln Pro Pro Ala Arg Arg Met Gly
 1               5                  10                  15

Trp Leu Pro Leu Leu Leu Leu Thr Gln Cys Leu Gly Val Pro Gly
            20                  25                  30

Gln Arg Ser Pro Leu Asn Asp Phe Gln Val Leu Arg Gly Thr Glu Leu
            35                  40                  45

Gln His Leu Leu His Ala Val Val Pro Gly Pro Trp Gln Glu Asp Val
        50                  55                  60

Ala Asp Ala Glu Glu Cys Ala Gly Arg Cys Gly Pro Leu Met Asp Cys
 65                  70                  75                  80

Arg Ala Phe His Tyr Asn Val Ser Ser His Gly Cys Gln Leu Leu Pro
                85                  90                  95

Trp Thr Gln His Ser Pro His Thr Arg Leu Arg Arg Ser Gly Arg Cys
            100                 105                 110

Asp Leu Phe Gln Lys Lys Asp Tyr Val Arg Thr Cys Ile Met Asn Asn
            115                 120                 125

Gly Val Gly Tyr Arg Gly Thr Met Ala Thr Thr Val Gly Gly Leu Pro
130                 135                 140

Cys Gln Ala Trp Ser His Lys Phe Pro Asn Asp His Lys Tyr Thr Pro
145                 150                 155                 160

Thr Leu Arg Asn Gly Leu Glu Glu Asn Phe Cys Arg Asn Pro Asp Gly
            165                 170                 175

Asp Pro Gly Gly Pro Trp Cys Tyr Thr Thr Asp Pro Ala Val Arg Phe
            180                 185                 190

Gln Ser Cys Gly Ile Lys Ser Cys Arg Glu Ala Ala Cys Val Trp Cys
            195                 200                 205

Asn Gly Glu Glu Tyr Arg Gly Ala Val Asp Arg Thr Glu Ser Gly Arg
210                 215                 220

Glu Cys Gln Arg Trp Asp Leu Gln His Pro His Gln His Pro Phe Glu
225                 230                 235                 240

Pro Gly Lys Phe Leu Asp Gln Gly Leu Asp Asp Asn Tyr Cys Arg Asn
            245                 250                 255

Pro Asp Gly Ser Glu Arg Pro Trp Cys Tyr Thr Thr Asp Pro Gln Ile
            260                 265                 270

Glu Arg Glu Phe Cys Asp Leu Pro Arg Cys Gly Ser Glu Ala Gln Pro
            275                 280                 285

Arg Gln Glu Ala Thr Thr Val Ser Cys Phe Arg Gly Lys Gly Glu Gly
290                 295                 300

Tyr Arg Gly Thr Ala Asn Thr Thr Thr Ala Gly Val Pro Cys Gln Arg
305                 310                 315                 320

Trp Asp Ala Gln Ile Pro His Gln His Arg Phe Thr Pro Glu Lys Tyr
            325                 330                 335

Ala Cys Lys Asp Leu Arg Glu Asn Phe Cys Arg Asn Pro Asp Gly Ser
            340                 345                 350

Glu Ala Pro Trp Cys Phe Thr Leu Arg Pro Gly Met Arg Ala Ala Phe
            355                 360                 365

Cys Tyr Gln Ile Arg Arg Cys Thr Asp Asp Val Arg Pro Gln Asp Cys
370                 375                 380

Tyr His Gly Ala Gly Glu Gln Tyr Arg Gly Thr Val Ser Lys Thr Arg
385                 390                 395                 400

Lys Gly Val Gln Cys Gln Arg Trp Ser Ala Glu Thr Pro His Lys Pro
            405                 410                 415
```

-continued

```
Gln Phe Thr Phe Thr Ser Glu Pro His Ala Gln Leu Glu Glu Asn Phe
                420                 425                 430

Cys Arg Asn Pro Asp Gly Asp Ser His Gly Pro Trp Cys Tyr Thr Met
            435                 440                 445

Asp Pro Arg Thr Pro Phe Asp Tyr Cys Ala Leu Arg Arg Cys Ala Asp
450                 455                 460

Asp Gln Pro Pro Ser Ile Leu Asp Pro Pro Asp Gln Val Gln Phe Glu
465                 470                 475                 480

Lys Cys Gly Lys Arg Val Asp Arg Leu Asp Gln Arg Ser Lys Leu
                485                 490                 495

Arg Val Val Gly Gly His Pro Gly Asn Ser Pro Trp Thr Val Ser Leu
                500                 505                 510

Arg Asn Arg Gln Gly Gln His Phe Cys Gly Gly Ser Leu Val Lys Glu
            515                 520                 525

Gln Trp Ile Leu Thr Ala Arg Gln Cys Phe Ser Ser Cys His Met Pro
            530                 535                 540

Leu Thr Gly Tyr Glu Val Trp Leu Gly Thr Leu Phe Gln Asn Pro Gln
545                 550                 555                 560

His Gly Glu Pro Ser Leu Gln Arg Val Pro Val Ala Lys Met Val Cys
                565                 570                 575

Gly Pro Ser Gly Ser Gln Leu Val Leu Leu Lys Leu Glu Arg Ser Val
                580                 585                 590

Thr Leu Asn Gln Arg Val Ala Leu Ile Cys Leu Pro Pro Glu Trp Tyr
            595                 600                 605

Val Val Pro Pro Gly Thr Lys Cys Glu Ile Ala Gly Trp Gly Glu Thr
610                 615                 620

Lys Gly Thr Gly Asn Asp Thr Val Leu Asn Val Ala Leu Leu Asn Val
625                 630                 635                 640

Ile Ser Asn Gln Glu Cys Asn Ile Lys His Arg Gly Arg Val Arg Glu
                645                 650                 655

Ser Glu Met Cys Thr Glu Gly Leu Leu Ala Pro Val Gly Ala Cys Glu
                660                 665                 670

Gly Asp Tyr Gly Gly Pro Leu Ala Cys Phe Thr His Asn Cys Trp Val
            675                 680                 685

Leu Glu Gly Ile Ile Ile Pro Asn Arg Val Cys Ala Arg Ser Arg Trp
690                 695                 700

Pro Ala Val Phe Thr Arg Val Ser Val Phe Val Asp Trp Ile His Lys
705                 710                 715                 720

Val Met Arg Leu Gly
            725

<210> SEQ ID NO 36
<211> LENGTH: 725
<212> TYPE: PRT
<213> ORGANISM: homo sapien

<400> SEQUENCE: 36

Met Gly Leu Trp Trp Val Thr Val Gln Pro Pro Ala Arg Arg Met Gly
1               5                   10                  15

Trp Leu Pro Leu Leu Leu Leu Thr Gln Cys Leu Gly Val Pro Gly
            20                  25                  30

Gln Arg Ser Pro Leu Asn Asp Phe Gln Val Leu Arg Gly Thr Glu Leu
            35                  40                  45

Gln His Leu Leu His Ala Val Val Pro Gly Pro Trp Gln Glu Asp Val
50                  55                  60
```

-continued

```
Ala Asp Ala Glu Glu Cys Ala Gly Arg Cys Gly Pro Leu Met Asp Cys
 65                  70                  75                  80

Arg Ala Phe His Tyr Asn Val Ser Ser His Gly Cys Gln Leu Leu Pro
                 85                  90                  95

Trp Thr Gln His Ser Pro His Thr Arg Leu Arg Arg Ser Gly Arg Cys
            100                 105                 110

Asp Leu Phe Gln Lys Lys Asp Tyr Val Arg Thr Cys Ile Met Asn Asn
        115                 120                 125

Gly Val Gly Tyr Arg Gly Thr Met Ala Thr Thr Val Gly Gly Leu Pro
    130                 135                 140

Cys Gln Ala Trp Ser His Lys Phe Pro Asn Asp His Lys Tyr Thr Pro
145                 150                 155                 160

Thr Leu Arg Asn Gly Leu Glu Glu Asn Phe Cys Arg Asn Pro Asp Gly
                165                 170                 175

Asp Pro Gly Gly Pro Trp Cys Tyr Thr Thr Asp Pro Ala Val Arg Phe
            180                 185                 190

Gln Ser Cys Gly Ile Lys Ser Cys Arg Glu Ala Ala Cys Val Trp Cys
        195                 200                 205

Asn Gly Glu Glu Tyr Arg Gly Ala Val Asp Arg Thr Glu Ser Gly Arg
    210                 215                 220

Glu Cys Gln Arg Trp Asp Leu Gln His Pro His Gln His Pro Phe Glu
225                 230                 235                 240

Pro Gly Lys Phe Leu Asp Gln Gly Leu Asp Asp Asn Tyr Cys Arg Asn
                245                 250                 255

Pro Asp Gly Ser Glu Arg Pro Trp Cys Tyr Thr Thr Asp Pro Gln Ile
            260                 265                 270

Glu Arg Glu Phe Cys Asp Leu Pro Arg Cys Gly Ser Glu Ala Gln Pro
        275                 280                 285

Arg Gln Glu Ala Thr Thr Val Ser Cys Phe Arg Gly Lys Gly Glu Gly
    290                 295                 300

Tyr Arg Gly Thr Ala Asn Thr Thr Ala Gly Val Pro Cys Gln Arg
305                 310                 315                 320

Trp Asp Ala Gln Ile Pro His Gln His Arg Phe Thr Pro Glu Lys Tyr
                325                 330                 335

Ala Cys Lys Asp Leu Arg Glu Asn Phe Cys Arg Asn Pro Asp Gly Ser
            340                 345                 350

Glu Ala Pro Trp Cys Phe Thr Leu Arg Pro Gly Met Arg Ala Ala Phe
        355                 360                 365

Cys Tyr Gln Ile Arg Arg Cys Thr Asp Asp Val Arg Pro Gln Asp Cys
    370                 375                 380

Tyr His Gly Ala Gly Glu Gln Tyr Arg Gly Thr Val Ser Lys Thr Arg
385                 390                 395                 400

Lys Gly Val Gln Cys Gln Arg Trp Ser Ala Glu Thr Pro His Lys Pro
                405                 410                 415

Gln Phe Thr Phe Thr Ser Glu Pro His Ala Gln Leu Glu Glu Asn Phe
            420                 425                 430

Cys Arg Asn Pro Asp Gly Asp Ser His Gly Pro Trp Cys Tyr Thr Met
        435                 440                 445

Asp Pro Arg Thr Pro Phe Asp Tyr Cys Ala Leu Arg Arg Cys Ala Asp
    450                 455                 460

Asp Gln Pro Pro Ser Ile Leu Asp Pro Pro Asp Gln Val Gln Phe Glu
465                 470                 475                 480
```

Lys Cys Gly Lys Arg Val Asp Arg Leu Asp Gln Arg Arg Ser Lys Leu
                485                 490                 495

Arg Val Val Gly Gly His Pro Gly Asn Ser Pro Trp Thr Val Ser Leu
            500                 505                 510

Arg Asn Arg Gln Gly Gln His Phe Cys Gly Gly Ser Leu Val Lys Glu
            515                 520                 525

Gln Trp Ile Leu Thr Ala Arg Gln Cys Phe Ser Ser Cys His Met Pro
            530                 535                 540

Leu Thr Gly Tyr Glu Val Trp Leu Gly Thr Leu Phe Gln Asn Pro Gln
545                 550                 555                 560

His Gly Glu Pro Ser Leu Gln Arg Val Pro Val Ala Lys Met Val Cys
                565                 570                 575

Gly Pro Ser Gly Ser Gln Leu Val Leu Leu Lys Leu Glu Arg Ser Val
            580                 585                 590

Thr Leu Asn Gln Arg Val Ala Leu Ile Cys Leu Pro Pro Glu Trp Tyr
            595                 600                 605

Val Val Pro Pro Gly Thr Lys Cys Glu Ile Ala Gly Trp Gly Glu Thr
            610                 615                 620

Lys Gly Thr Gly Asn Asp Thr Val Leu Asn Val Ala Leu Leu Asn Val
625                 630                 635                 640

Ile Ser Asn Gln Glu Cys Asn Ile Lys His Arg Gly Arg Val Arg Glu
                645                 650                 655

Ser Glu Met Cys Thr Glu Gly Leu Leu Ala Pro Val Gly Ala Cys Glu
            660                 665                 670

Gly Asp Tyr Gly Gly Pro Leu Ala Cys Phe Thr His Asn Cys Trp Val
            675                 680                 685

Leu Glu Gly Ile Ile Ile Pro Asn Arg Val Cys Ala Arg Ser Cys Trp
690                 695                 700

Pro Ala Val Phe Thr Arg Val Ser Val Phe Val Asp Trp Ile His Lys
705                 710                 715                 720

Val Met Arg Leu Gly
            725

<210> SEQ ID NO 37
<211> LENGTH: 5107
<212> TYPE: DNA
<213> ORGANISM: homo sapien

<400> SEQUENCE: 37
gaagctgggg caagtaattt tccccaattt acagggaaaa accgaaattc agaaaagttt        60
aatgtcaccc aggggctgga gcccagacct ctggcagctc tcactttcac aatgcccttg       120
ggctgactag gctgcagagg ggtttcaccc caacccagg gcacctcaag tgtccccacc        180
aaaccttcct aacacctgtc cactaagctg tactaggccc ttgcaactga cctatgggac       240
ctgaggcctg cccctcatg gctcctgtca ccaggtctca ggtcagggtc cagcaggccc        300
tgagctgacg tgtggagcca gagccaccca atcccgtagg gacaggtttc acaacttccc       360
ggatggggct gtggtgggtc acagtgcagc ctccagccag aaggatgggg tggctcccac       420
tcctgctgct tctgactcaa tgcttagggg tccctggtaa gtgccccaa ccctgatccc        480 catctgcctt caggaggggg ttggccccat tctcctattc taggatgaga aaaagtcgg        540 ggagccagag gctcagtggg catggggcag tgaccttgcc ctcttgagca cagctgggaa       600
gccctaggaa cacatagaca ttgcccactt aggcctctat tagcacgtct gctctagcac       660
tgaagcagtg tcaggaccac acagatgcac gcacacagca ggcagtgacc cctcctgagc       720

```
ctgatctacc cctctaacct agcatatgcc tttgtgcagg tgagagccca gatttggagt    780
ctgaatgcct agccagggcc cctggctggg taatgtgatg gctctgagcc ttagcattct    840
catttgagag atgaggtggg gcaagcttca tcacccactg ctctcacaga gcgtatgtgt    900
tagatctgag cccggtgcct gggccactaa acagaggcac cggtgataac taccaagtct    960
gggcctgctt cccaggggaa attttttttca caagtatctg tgcaggggggc tagactggcc   1020 cttgaaagtg catacagggt ccatcccaga agccttgtag ctttgatccc ctgaatgaac   1080
aaagtgtgga catgccaata cacattactg acatgtatgc ccacctgacc tgcacccact   1140
catgcctact ctgcagggca gcgctcgcca ttgaatgact tccaagtgct ccggggcaca   1200
gagctacagc acctgctaca tgcggtggtg cccgggcctt ggcaggagga tgtggcagat   1260
gctgaagagt gtgctggtcg ctgtgggccc ttaatggact gccggtgagt ggccactggg   1320
cctagataag actgggggca gggaagcctg ggctgtggcg ttaccctgtg ccttcttctc   1380
tccagggcct ccactacaa cgtgagcagc catggttgcc aactgctgcc atggactcaa   1440
cactcgcccc acacgaggct gcggcgttct gggcgctgtg acctcttcca gaagaaaggc   1500
aagtgggggt ggagagggc agggtgggag acagggacc tcagcccaag ttgatcttct   1560
gtctcttgct cccagactac gtacggacct gcatcatgaa caatggggtt gggtaccggg   1620
gcaccatggc cacgaccgtg ggtggcctgc cctgccaggc ttggagccac aagttcccaa   1680
atgatcacaa gtgagacaaa caccttccct ccgtcccggc ctggggcctt cccccagcac   1740
acactatagt gatgctctgg gccctcaggt acacgcccac tctccggaat ggcctggaag   1800
agaacttctg ccgtaaccct gatggcgacc ccggaggtcc ttggtgctac acaacagacc   1860
ctgctgtgcg cttccagagc tgcggcatca atcctgccg ggagggtaag cggcgccggg   1920
tcaagctggg agagtggagg gacaagccca cgtccatcca cgaacccact ggctctttgt   1980
ctccagccgc gtgtgtctgg tgcaatggcg aggaataccg cggcgcggta gaccgcacgg   2040
agtcagggcg cgagtgccag cgctgggatc ttcagcaccc gcaccagcac cccttcgagc   2100
cgggcaagta cgcgtaggcg gtatcggcgt cctgggggcc gggctaggga aggtccagga   2160 ctccagggc agggctccgt gtagggcaat tgggcggggc cagataagcc agagtcccag   2220
ggtcttgttc acgccccatt accgccccca ggttcctcga ccaaggtctg gacgacaact   2280
attgccggaa tcctgacggc tccgagcggc atggtgcta cactacgat ccgcagatcg   2340 agcgagagtt ctgtgacctc cccctgctgcg gtaggcggcg gggaccaggc ctgggagggt   2400
acctgggaac cttggggagg ggcgtggctt ggccggggag gtaagagggg ctgggcgtga   2460
cctgagagca taccccgtgg agtaccgtac acctgggaaa ggcgggttgg gtcccagccc   2520
cagagggatc tcagctctcg ctcggggccc gacctatctc ggtccatcta agggtccgag   2580
gcacagcccc gccaagaggc cacaactgtc agctgcttcc gcgggaaggg tgagggctac   2640
cggggcacag ccaataccac cactgcgggc gtaccttgcc agcgttggga cgcgcaaatc   2700
ccgcatcagc accgatttac gccagaaaaa tacgcgtgca agtgaggtgg ggggggggg   2760 cgggcgttgg gacgtgctgc tgcgggtgag acgggaggaa ggtagtcacg ggctcaaggc   2820
tggaggctgg cgggctaggg ctgagtggag cgcctgctta gagaccttcg ggagaacttc   2880
tgccggaacc ccgacggctc agaggcgccc tggtgcttca cactgcggcc cggcatgcgc   2940
gcggcctttt gctaccagat ccggcgttgt acagacgacg tgcggcccca gggtgaggcc   3000
caagcttggg ggctacagag ccgggctgga agcctggaac cggagggccg gggcgaggtc   3060
```

```
tcggcctgat ggctgcccgc acccgccaca gactgctacc acggcgcagg ggagcagtac   3120
cgcggcacgg tcagcaagac ccgcaagggt gtccagtgcc agcgctggtc cgctgagacg   3180
ccgcacaagc cgcagtgagt ccctggtgct cccggccccg ccagggccct aaccctgggg   3240
cggcatgctt tggtgtctgg gaccagagcc tggaaatggt tgagactacc ctgccacgat   3300
tttgctcccg cttccgccta ggttcacgtt tacctccgaa ccgcatgcac aactggagga   3360
gaacttctgc cggaacccag atggggatag ccatgggccc tggtgctaca cgatggaccc   3420
aaggacccca ttcgactact gtgccctgcg acgctgcggt gagcactagt gacgcttccc   3480
ccatgaccct gcctcagccc ccacccaaag gctggctccc ttaacccag tgaactttgt    3540 cttcagctg atgaccagcc gccatcaatc ctgaccccc caggttagga gttgggccag     3600
ttatgggtca ggccctttag cccacgacat ccacacagtc tgggtttcat ccagcccacc   3660
ccatcctaca gaccaggtgc agtttgagaa gtgtggcaag agggtggatc ggctggatca   3720
gcggcgttcc aagctgcgcg tggttggggg ccatccgggc aactcaccct ggacagtcag   3780
cttgcggaat cggtgaggca caactgcctg tctcccacag agaggagctg aggttgtgtc   3840
ctctgtggtt atcccactgg gggctgggaa tctatccctg cccccagagg tcctagccag   3900
aagatggcag gtctagcatc tgtcccagga gtctgttacc tgtcctaatt ccccactcct   3960
ctaggcaggg ccagcatttc tgcgggggt ctctagtgaa ggagcagtgg atactgactg     4020
cccggcagtg cttctcctcc tggtgagcct cccttgtgtt tggggaccca gtctcatccc    4080
accttccccc ttcccaggc aagctaacaa gtgagccttg ggcaatgga ctgagagtca      4140 caaatgacct agcagagctt ctctcccagc catatgcctc tcacgggcta tgaggtatgg   4200
ttgggcaccc tgttccagaa cccacagcat ggagagccaa gcctacagcg ggtcccagta   4260
gccaagatgt gtgtgtgggcc ctcaggctcc cagcttgtcc tgctcaagct ggagaggtat  4320
gtggacaacc tgggagggtg tgaggtgggg ctgggccttg tggcctcaga ccctgagtgc   4380
ccccattctt gctaaagatc tgtgaccctg aaccagcgtg tggccctgat ctgcctgccc   4440
cctgaatggt atgtggtgcc tccagggacc aagtgtgaga ttgcaggctg gggtgagacc   4500
aaaggtaaga gcacagtgca caggactgct ggtggccagg aggcccagcc ctggatcttc   4560
ctgcaggacc ctctccctct ccccattccc ctcactgcag gtacgggtaa tgacacagtc   4620
ctaaatgtgg ccttgctgaa tgtcatctcc aaccaggagt gtaacatcaa gcactgagga   4680
cgtgtgcggg agagtgagat gtgcactgag ggactgttgg cccctgtggg ggcctgtgag   4740
gttggtggca gggccctggg ccagccctgg aagggtatgg ggggctagaa atgaactatt   4800
ttatcatgaa gcaggctagt cattgctgtg gcccggggcc ctcatcagtt ctcctacctg   4860
ccagggtgac tacgggggcc cacttgcctg ctttacccac aactgctggg tcctggaagg   4920
aattataatc cccaaccgag tatgcgcaag gtcccgctgg ccagctgtct tcacgcgtgt   4980
ctctgtgttt gtggactgga ttcacaaggt catgagactg ggttaggccc agccttgatg   5040
ccatatgcct tggggaggac aaaacttctt gtcagacata aagccatgtt tcctctttat   5100
gcctgta                                                              5107
```

<210> SEQ ID NO 38
<211> LENGTH: 2621
<212> TYPE: DNA
<213> ORGANISM: homo sapien

<400> SEQUENCE: 38

```
gaagcugggg caaguaauuu uccccaauuu acagggaaaa accgaaauuc agaaaaguuu   60
```

-continued

```
aaugucaccc aggggcugga gcccagaccu cuggcagcuc ucacuuucac aaugcccuug    120
ggcugacuag gcugcagagg gguuucaccc caaccccagg gcaccucaag uguccccacc    180
aaaccuuccu aacaccuguc cacuaagcug uacuaggccc uugcaacuga ccuaugggac    240
cugaggccug gccccucaug gcuccuguca ccaggucuca ggucaggguc cagcaggccc    300
ugagcugacg uguggagcca gagccaccca aucccguagg gacagguuuc acaacuuccc    360 ggaugggggcu gugguggguc acagugcagc cuccagccag aaggaugggg uggcucccac    420
uccugcugcu ucugacucaa ugcuuagggg ucccugggca gcgcucgcca uugaaugacu    480
uccaagugcu ccggggcaca gagcuacagc accugcuaca ugcggugguug cccgggccuu    540 ggcaggagga uguggcagau gcugaagagu gugcuggucg cuguggggccc uuaauggacu    600 gccgggccuu ccacuacaac gugagcagcc augguugcca acugcugcca uggacucaac    660
acucgcccca cacgaggcug cggcguucug ggcgcuguga ccucuuccag aagaaagacu    720
acguacggac cugcaucaug aacaaugggg uuggguaccg gggcaccaug gccacgaccg    780
uggguggccu gcccugccag gcuuggagcc acaaguuccc aaaugaucac aaguacacgc    840
ccacucuccg gaauggccug gaagagaacu ucugccguaa cccugauggc gaccccggag    900
guccuuggug cuacacaaca gacccugcug ugcgcuucca gagcugcggc aucaaauccu    960
gccgggaggc cgcgugguuc uggugcaaug gcgaggaaua ccgcggcgcg guagaccgca    1020
cggagucagg gcgcgagugc cagcgcuggg aucuucagca cccgcaccag caccccuucg    1080
agccgggcaa guuccucgac caaggucugg acgacaacua uugccggaau ccugacggcu    1140
ccgagcggcc auggugcuac acuacggauc cgcagaucga gcgagaguuc ugugaccucc    1200
cccgcugcgg guccgaggca cagccccgcc aagaggccac aacugucagc ugcuuccgcg    1260
ggaaggguga gggcuaccgg ggcacagcca auaccaccac ugcgggcgua ccuugccagc    1320
guugggacgc gcaaaucccg caucagcacc gauuuacgcc agaaaaauac gcgugcaaag    1380
accuucggga gaacuucugc cggaaccccg acggcucaga ggcgcccugg ugcuucacac    1440
ugcggcccgg caugcgcgcg gccuuuugcu accagaucg gcguuguaca gacgacgugc    1500
ggccccagga cugcuaccac ggcgcagggg agcaguaccg cggcacgguc agcaagaccc    1560
gcaagggugu ccagugccag cgcuggguccg cugagacgcc gcacaagccc caguucacgu    1620
uuaccuccga accgcaugca caacuggagg agaacuucug ccggaacccca gauggggaua    1680 gccaugggcc cuggugcuac acgauggacc caaggacccc auucgacuac ugugcccugc    1740
gacgcugcgc ugaugaccag ccgccaucaa uccuggaccc cccagaccag gugcaguuug    1800
agaagugugg caagagggug gaucggcugg aucagcggcg uuccaagcug cgcguggulug    1860 ggggccaucc gggcaacuca cccggacag ucagcuugcg gaaucggcag gccagcauu    1920 ucugcggggg gucucuagug aaggagcagu ggauacugac ugcccggcag ugcuucuccu    1980
ccugccauau gccucucacg ggcuaugagg uauggulugg cacccuguuc cagaacccac    2040
agcauggaga gccaagccua cagcggguccu cagucagccaa gauggugugu gggcccucag    2100
gcucccagcu uguccugcuc aagcuggaga gaucucugac ccugaaccag cguguggccc    2160
ugaucugccu gccccccugaa ugguaugugg ugccuccagg gaccaagugu gagauugcag    2220 gcuggggguga gaccaaaggu acggguaaug acacaguccu aaauguggcc uugcugaaug    2280
ucaucuccaa ccaggagugu aacaucaagc acugaggacg ugcgcggag agugagaugu    2340 gcacugaggg acuguuggcc ccugugggg ccugugaggu ugacuacggg ggcccacuug    2400
```

```
ccugcuuuac ccacaacugc uggguccugg aaggaauuau aauccccaac cgaguaugcg    2460
caagguCCcg cuggccagcu gucuucacgc gugucucugu guuguggac uggauucaca    2520 aggucaugag acuggguuag gcccagccuu gaugccauau gccuugggga ggacaaaacu    2580
ucuugucaga cauaaagcca uguuuccucu uuaugccugu a                       2621
```

<210> SEQ ID NO 39
<211> LENGTH: 2621
<212> TYPE: DNA
<213> ORGANISM: homo sapien

<400> SEQUENCE: 39

```
gaagctgggg caagtaattt tccccaattt acagggaaaa accgaaattc agaaaagttt      60
aatgtcaccc aggggctgga gcccagacct ctggcagctc tcactttcac aatgcccttg     120
ggctgactag gctgcagagg ggtttcaccc caaccccagg gcacctcaag tgtccccacc     180
aaaccttcct aacacctgtc cactaagctg tactaggccc ttgcaactga cctatgggac     240
ctgaggcctg gccctcatg gctcctgtca ccaggtctca ggtcagggtc cagcaggccc      300
tgagctgacg tgtggagcca gagccaccca atcccgtagg acaggtttc acaacttccc     360 ggatggggct gtggtgggtc acagtgcagc ctccagccag aaggatgggg tggctcccac    420
tcctgctgct tctgactcaa tgcttagggg tccctgggca gcgctcgcca ttgaatgact    480
tccaagtgct ccggggcaca gagctacagc acctgctaca tgcggtggtg cccgggcctt    540
ggcaggagga tgtggcagat gctgaagagt gtgctggtcg ctgtgggccc ttaatggact    600
gccgggcctt ccactacaac gtgagcagcc atggttgcca actgctgcca tggactcaac    660
actcgcccca cacgaggctg cggcgttctg ggcgctgtga cctcttccag aagaaagact    720
acgtacggac ctgcatcatg aacaatgggg ttgggtaccg gggcaccatg gccacgaccg    780
tgggtggcct gccctgccag gcttggagcc acaagttccc aaatgatcac aagtacacgc    840
ccactctccg gaatggcctg aagagaact tctgccgtaa ccctgatggc gaccccggag    900
gtccttggtg ctacacaaca gaccctgctg tgcgcttcca gagctgcggc atcaaatcct    960
gccgggaggc cgcgtgtgtc tggtgcaatg gcgaggaata ccgcggcgcg gtagaccgca    1020
cggagtcagg gcgcgagtgc cagcgctggg atcttcagca cccgcaccag caccccttcg    1080
agccgggcaa gttcctcgac caaggtctgg acgacaacta ttgccggaat cctgacggct    1140
ccgagcggcc atggtgctac actacggatc cgcagatcga gcgagagttc tgtgacctcc    1200
cccgctgcgg gtccgaggca cagccccgcc aagaggccac aactgtcagc tgcttccgcg    1260
ggaagggtga gggctaccgg ggcacagcca ataccaccac tgcgggcgta ccttgccagc    1320
gttgggacgc gcaaatcccg catcagcacc gatttacgcc agaaaaatac gcgtgcaaag    1380
accttcggga gaacttctgc cggaacccg acggctcaga ggcgcctgg tgcttcacac      1440 tgcggcccgg catgcgcgcg gccttttgct accagatccg gcgttgtaca gacgacgtgc    1500 ggcccagga ctgctaccac ggcgcagggg agcagtaccg cggcacggtc agcaagaccc     1560
gcaagggtgt ccagtgccag cgctggtccg ctgagacgcc gcacaagccg cagttcacgt    1620
ttacctccga accgcatgca caactggagg agaacttctg ccggaaccca gatgggggata   1680 gccatgggcc ctggtgctac acgatggacc caaggacccc attcgactac tgtgccctgc    1740
gacgtgcgcg tgatgaccag ccgccatcaa tcctggaccc ccagaccag gtgcagtttg     1800 agaagtgtgg caagagggtg gatcggctgg atcagcggg ttccaagctg cgcgtggttg     1860
ggggccatcc gggcaactca ccctggacag tcagcttgcg gaatcggcag ggccagcatt    1920
```

```
tctgcggggg gtctctagtg aaggagcagt ggatactgac tgcccggcag tgcttctcct   1980
cctgccatat gcctctcacg ggctatgagg tatggttggg caccctgttc cagaacccac   2040
agcatggaga gccaagccta cagcgggtcc cagtagccaa gatggtgtgt gggccctcag   2100
gctcccagct tgtcctgctc aagctggaga gatctgtgac cctgaaccag cgtgtggccc   2160
tgatctgcct gccccctgaa tggtatgtgg tgcctccagg gaccaagtgt gagattgcag   2220
gctgggtga gaccaaaggt acgggtaatg acacagtcct aaatgtggcc ttgctgaatg    2280
tcatctccaa ccaggagtgt aacatcaagc actgaggacg tgtgcgggag agtgagatgt   2340
gcactgaggg actgttggcc cctgtggggg cctgtgaggg tgactacggg ggcccacttg   2400
cctgctttac ccacaactgc tgggtcctgg aaggaattat aatccccaac cgagtatgcg   2460
caaggtcccg ctggccagct gtcttcacgc gtgtctctgt gtttgtggac tggattcaca   2520
aggtcatgag actgggttag gcccagcctt gatgccatat gccttgggga ggacaaaact   2580
tcttgtcaga cataaagcca tgtttcctct ttatgcctgt a                       2621
```

<210> SEQ ID NO 40
<211> LENGTH: 650
<212> TYPE: PRT
<213> ORGANISM: homo sapien

<400> SEQUENCE: 40

```
Met Gly Leu Trp Trp Val Thr Val Gln Pro Ala Arg Arg Met Gly
1               5                   10                  15

Trp Leu Pro Leu Leu Leu Leu Leu Thr Gln Cys Leu Gly Val Pro Gly
            20                  25                  30

Gln Arg Ser Pro Leu Asn Asp Phe Gln Val Leu Arg Gly Thr Glu Leu
        35                  40                  45

Gln His Leu Leu His Ala Val Val Pro Gly Pro Trp Gln Glu Asp Val
    50                  55                  60

Ala Asp Ala Glu Glu Cys Ala Gly Arg Cys Gly Pro Leu Met Asp Cys
65                  70                  75                  80

Arg Ala Phe His Tyr Asn Val Ser Ser His Gly Cys Gln Leu Leu Pro
                85                  90                  95

Trp Thr Gln His Ser Pro His Thr Arg Leu Arg Arg Ser Gly Arg Cys
            100                 105                 110

Asp Leu Phe Gln Lys Lys Asp Tyr Val Arg Thr Cys Ile Met Asn Asn
        115                 120                 125

Gly Val Gly Tyr Arg Gly Thr Met Ala Thr Thr Val Gly Gly Leu Pro
    130                 135                 140

Cys Gln Ala Trp Ser His Lys Phe Pro Asn Asp His Lys Tyr Thr Pro
145                 150                 155                 160

Thr Leu Arg Asn Gly Leu Glu Glu Asn Phe Cys Arg Asn Pro Asp Gly
                165                 170                 175

Asp Pro Gly Gly Pro Trp Cys Tyr Thr Thr Asp Pro Ala Val Arg Phe
            180                 185                 190

Gln Ser Cys Gly Ile Lys Ser Cys Arg Glu Ala Ala Cys Val Trp Cys
        195                 200                 205

Asn Gly Glu Glu Tyr Arg Gly Ala Val Asp Arg Thr Glu Ser Gly Arg
    210                 215                 220

Glu Cys Gln Arg Trp Asp Leu Gln His Pro His Gln His Pro Phe Glu
225                 230                 235                 240

Pro Gly Lys Phe Leu Asp Gln Gly Leu Asp Asp Asn Tyr Cys Arg Asn
```

```
                245                 250                 255
Pro Asp Gly Ser Glu Arg Pro Trp Cys Tyr Thr Thr Asp Pro Gln Ile
            260                 265                 270
Glu Arg Glu Phe Cys Asp Leu Pro Arg Cys Gly Ser Glu Ala Gln Pro
            275                 280                 285
Arg Gln Glu Ala Thr Thr Val Ser Cys Phe Arg Gly Lys Gly Glu Gly
            290                 295                 300
Tyr Arg Gly Thr Ala Asn Thr Thr Thr Ala Gly Val Pro Cys Gln Arg
305                 310                 315                 320
Trp Asp Ala Gln Ile Pro His Gln His Arg Phe Thr Pro Glu Lys Tyr
                325                 330                 335
Ala Cys Lys Asp Leu Arg Glu Asn Phe Cys Arg Asn Pro Asp Gly Ser
                340                 345                 350
Glu Ala Pro Trp Cys Phe Thr Leu Arg Pro Gly Met Arg Ala Ala Phe
                355                 360                 365
Cys Tyr Gln Ile Arg Arg Cys Thr Asp Asp Val Arg Pro Gln Asp Cys
            370                 375                 380
Tyr His Gly Ala Gly Glu Gln Tyr Arg Gly Thr Val Ser Lys Thr Arg
385                 390                 395                 400
Lys Gly Val Gln Cys Gln Arg Trp Ser Ala Glu Thr Pro His Lys Pro
                405                 410                 415
Gln Phe Thr Phe Thr Ser Glu Pro His Ala Gln Leu Glu Glu Asn Phe
            420                 425                 430
Cys Arg Asn Pro Asp Gly Asp Ser His Gly Pro Trp Cys Tyr Thr Met
            435                 440                 445
Asp Pro Arg Thr Pro Phe Asp Tyr Cys Ala Leu Arg Arg Cys Ala Asp
            450                 455                 460
Asp Gln Pro Pro Ser Ile Leu Asp Pro Pro Asp Gln Val Gln Phe Glu
465                 470                 475                 480
Lys Cys Gly Lys Arg Val Asp Arg Leu Asp Gln Arg Arg Ser Lys Leu
                485                 490                 495
Arg Val Val Gly Gly His Pro Gly Asn Ser Pro Trp Thr Val Ser Leu
                500                 505                 510
Arg Asn Arg Gln Gly Gln His Phe Cys Gly Gly Ser Leu Val Lys Glu
            515                 520                 525
Gln Trp Ile Leu Thr Ala Arg Gln Cys Phe Ser Ser Cys His Met Pro
            530                 535                 540
Leu Thr Gly Tyr Glu Val Trp Leu Gly Thr Leu Phe Gln Asn Pro Gln
545                 550                 555                 560
His Gly Glu Pro Ser Leu Gln Arg Val Pro Val Ala Lys Met Val Cys
                565                 570                 575
Gly Pro Ser Gly Ser Gln Leu Val Leu Leu Lys Leu Glu Arg Ser Val
            580                 585                 590
Thr Leu Asn Gln Arg Val Ala Leu Ile Cys Leu Pro Pro Glu Trp Tyr
            595                 600                 605
Val Val Pro Pro Gly Thr Lys Cys Glu Ile Ala Gly Trp Gly Glu Thr
            610                 615                 620
Lys Gly Thr Gly Asn Asp Thr Val Leu Asn Val Ala Leu Leu Asn Val
625                 630                 635                 640
Ile Ser Asn Gln Glu Cys Asn Ile Lys His
                645                 650
```

MACROPHAGE STIMULATING 1 RECEPTOR (MST1R) VARIANTS AND USES THEREOF

REFERENCE TO A SEQUENCE LISTING

This application includes a Sequence Listing submitted electronically as a text file named 18923802901SEQ, created on Aug. 8, 2020, with a size of 205,731 bytes. The Sequence Listing is incorporated herein by reference.

FIELD

The present disclosure provides methods of treating patients having inflammatory bowel disease (IBD) or primary sclerosing cholangitis (PSC).

BACKGROUND

IBD is group of inflammatory conditions of the colon and small intestine that cause over 50,000 deaths annually. The causes of IBD are complex, and contributing factors may include diet, genetics, and the composition of an individual's gut microflora. Medical treatment is largely based on factors specific to an individual.

Crohn's disease (CD) and ulcerative colitis (UC) are among the most common forms of IBD. Both CD and UC are inflammatory diseases, but while UC is localized to the colon, CD can affect any part of the gastrointestinal tract, from mouth to anus. Neither CD nor UC are currently medically curable, and current treatments range from surgical removal of parts of the intestine to administration of anti-inflammatory and/or immunosuppressive drugs. Unfortunately, current treatments for CD and UC are often ineffective and can result in significant side effects.

PSC was originally defined as a chronic cholestatic liver disease characterized by fibrosing inflammation of segments of the extrahepatic bile ducts. PSC results in a progressive narrowing or obliteration of bile duct lumens, progression to secondary biliary cirrhosis, with complications of portal hypertension, hepatic failure, and cholangiocarcinoma. It is an idiopathic disorder characterized by inflammation and obliteration of both intra-hepatic and extrahepatic bile ducts. Further, roughly two-thirds or more of all PSC patients have concomitant IBD. However, the relationship between these two diseases remains undefined. Cholangiocytes account for 3%-5% of the hepatic cell population and line a complex network of interconnecting conduits in the liver, termed the intrahepatic biliary ductal system. One of the pathological conditions manifested in both the intrahepatic and extrahepatic bile ducts is PSC. Medical treatment of PSC has included corticosteroids, antibiotics, immunosuppressants, and cholecystogues alone or in combination. In general, results with all have been disappointing, and, in the absence of a liver transplant, the median age from diagnosis to death is 10 years. Thus, there is a continuing need for new methods and compositions for the treatment of IBD and/or PSC.

MST1 encodes macrophage stimulating protein (MSP; alternately designated MST1 protein), a liver-secreted protein that binds to its cognate receptor MST1R (alternately designated Recepteur d'Origine Nantais, or RON), which is expressed on macrophages, Kupffer cells, and epithelial cells of the intestine, among other cell types. MST1/MST1R signaling drives macrophage polarization, cellular chemotaxis, and epithelial wound repair. Previous genome-wide association studies (GWAS) in PSC and IBD patients and healthy controls have identified a common missense variant in MST1 (3:49684099:G:A; rs3197999) that associates with increased risk of PSC (OR 1.3, p=2e-26) and IBD (OR 1.2, p=1e-47) in published meta-GWAS. Functional studies have shown that 3:49684099:G:A rs3197999 associates with decreased MST1 protein levels in human serum. Collectively, these data indicate that decreased MST1 is associated with increased risk of PSC and IBD.

MST1R is a cell surface receptor for MST1 with tyrosine kinase activity. The mature form of this protein is a heterodimer of disulfide-linked alpha and beta subunits, generated by proteolytic cleavage of a single-chain precursor. MST1R functions as a tyrosine kinase that transduces signals from the extracellular matrix into the cytoplasm by binding to MST1 ligand. To date, MST1R has not been independently associated with IBD or PSC in genetic association studies.

SUMMARY

The present disclosure provides methods of treating a patient having IBD, the method comprising administering to the patient an agonist of the MST1/MST1R pathway.

The present disclosure also provides methods of treating a patient having PSC, the method comprising administering to the patient an agonist of the MST1/MST1R pathway.

The present disclosure also provides, in some embodiments, such methods wherein the presence or absence of an MST1 and/or MST1R variant nucleic acid molecule or variant polypeptide associated with an increased risk of developing IBD and/or PSC is detected in a biological sample from the patient.

BRIEF DESCRIPTION OF THE FIGURES

The accompanying figures, which are incorporated in and constitute a part of this specification, illustrate several aspects and together with the description serve to explain some principles of the present disclosure.

The patent or application file contains at least one drawing executed in color. Copies of this patent or patent application publication with color drawings will be provided by the Office upon request and payment of the necessary fee.

DESCRIPTION

Figure 1:
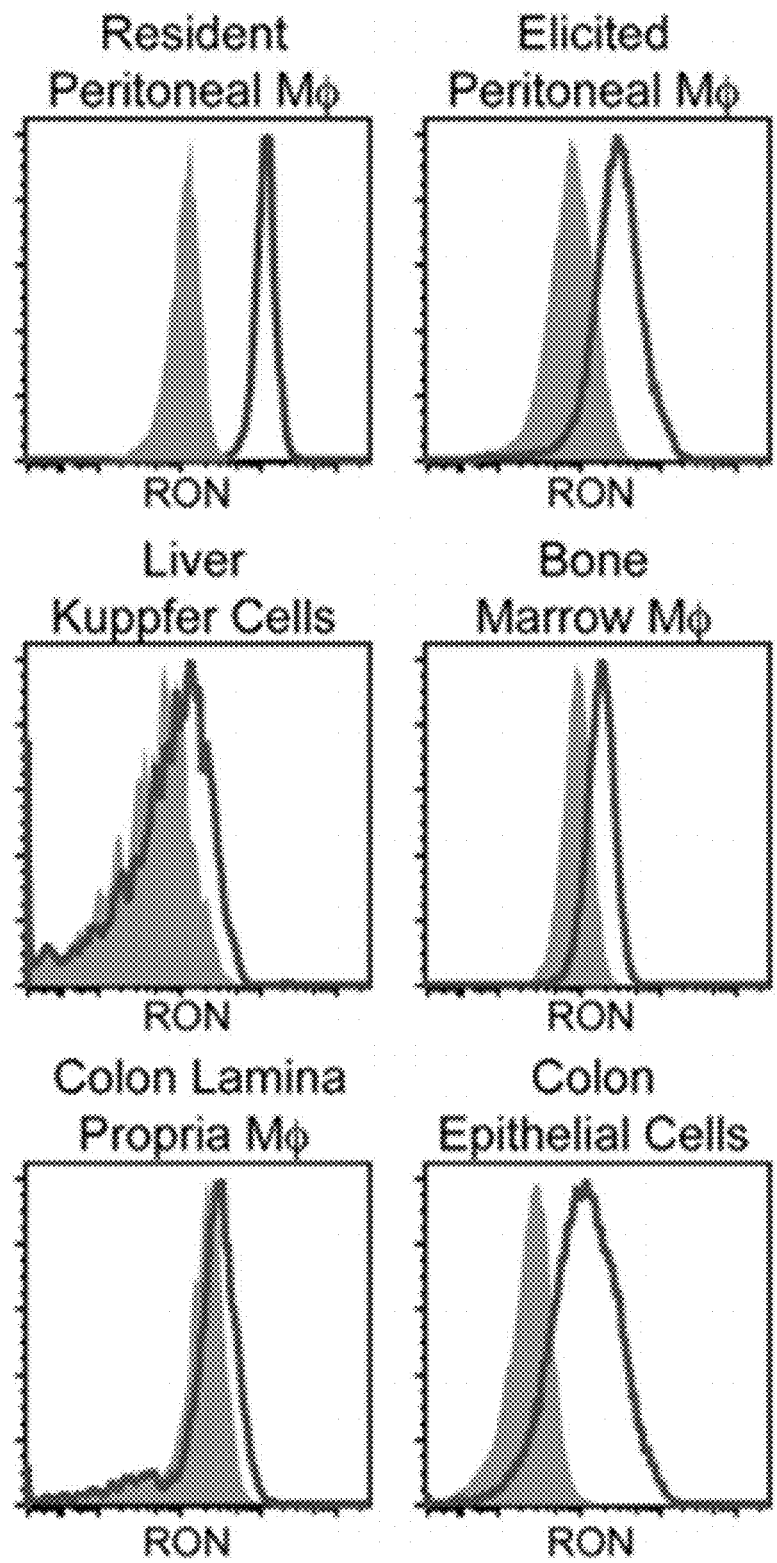
FIG. 1 shows MST1R protein expression in mouse peritoneal macrophages, liver Kuppfer cells, bone marrow macrophages, colon lamina propria macrophages, and colon epithelial cells by flow cytometry (Kauder et al., PLoS ONE, 2013, 8, e83958).

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

As used herein, the phrase "corresponding to", or grammatical variations thereof, when used in the context of the numbering of a particular amino acid or nucleotide sequence or position refers to the numbering of a specified reference sequence when the particular amino acid or nucleotide sequence is compared to the reference sequence (e.g., with the reference sequence herein being the nucleic acid molecule or polypeptide of (wild type) MST1R). In other words, the residue (e.g., amino acid or nucleotide) number or residue (e.g., amino acid or nucleotide) position of a particular polymer is designated with respect to the reference sequence rather than by the actual numerical position of the residue within the particular amino acid or nucleotide sequence. For example, a particular amino acid sequence or nucleotide sequence can be aligned to a reference sequence by introducing gaps to optimize residue matches between the two sequences. In these cases, although the gaps are present, the numbering of the residue in the particular amino acid or nucleotide sequence is made with respect to the reference sequence to which it has been aligned. A variety of computational algorithms exist that can be used for performing a sequence alignment to identify a nucleotide or amino acid position in one polymeric molecule that corresponds to a nucleotide or amino acid position in another polymeric molecule. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

It has been observed in accordance with the present disclosure that an aggregate burden of certain variations in MST1R associate with a risk of developing IBD or PSC. It is believed that variants in MST1R gene or protein have not been associated with IBD or PSC in genome-wide or exome-wide association studies. Therefore, humans having MST1R alterations that associate with IBD or PSC may be treated such that IBD or PSC is inhibited, the symptoms thereof are reduced, and/or development of symptoms is repressed. It is also believed that humans having IBD or PSC may be treated with molecules that promote MST1/MST1R signaling.

For purposes of the present disclosure, any particular human can be categorized as having any combination of the following MST1 and/or MST1R genotypes: i) MST1 and/or MST1R reference; ii) heterozygous for an MST1 and/or MST1R variant nucleic acid molecule associated with an increased risk of developing IBD and/or PSC, and iii) homozygous for an MST1 and/or MST1R variant nucleic acid molecule associated with an increased risk of developing IBD and/or PSC. A human is MST1 and/or MST1R reference when the human does not have a copy of an MST1 and/or MST1R variant nucleic acid molecule associated with an increased risk of developing IBD and/or PSC. A human is heterozygous for an MST1 and/or MST1R variant nucleic acid molecule associated with an increased risk of developing IBD and/or PSC when the human has a single copy of an MST1 and/or MST1R variant nucleic acid molecule associated with an increased risk of developing IBD and/or PSC. A human is homozygous for an MST1 and/or MST1R variant nucleic acid molecule associated with an increased risk of developing IBD and/or PSC when the human has two copies of any of the MST1 and/or MST1R variant nucleic acid molecule associated with an increased risk of developing IBD and/or PSC.

An MST1 and/or MST1R variant nucleic acid molecule associated with an increased risk of developing IBD and/or PSC is any MST1 and/or MST1R nucleic acid molecule (such as, a genomic nucleic acid molecule, an mRNA molecule, or a cDNA molecule produced from the mRNA molecule) encoding an MST1 and/or MST1R polypeptide having a partial loss-of-function, a complete loss-of-function, a predicted partial loss-of-function, or a predicted complete loss-of-function (collectively, "predicted loss-of-function" variant nucleic acid molecule). A human who has an MST1 and/or MST1R polypeptide having a partial loss-of-function (or predicted partial loss-of-function) is hypomorphic for MST1 and/or MST1R. The MST1 and/or MST1R predicted loss-of-function variant nucleic acid molecule can be any one or more of the variant nucleic acid molecules described herein.

An MST1 and/or MST1R variant nucleic acid molecule associated with an increased risk of developing IBD and/or PSC is also any MST1 and/or MST1R deleterious missense variant nucleic acid molecule. The MST1 and/or MST1R deleterious missense variant nucleic acid molecule can be any one or more of the variant nucleic acid molecules described herein.

For human subjects or patients that are genotyped or determined to be heterozygous or homozygous for an MST1 and/or MST1R variant nucleic acid molecule associated with an increased risk of developing IBD and/or PSC, such human subjects or patients are associated with having increased odds of developing IBD and/or PSC.

In any of the embodiments described herein, the MST1 and/or MST1R variant nucleic acid molecule associated with an increased risk of developing IBD and/or PSC can be any MST1 and/or MST1R nucleic acid molecule (such as, for example, genomic nucleic acid molecule, mRNA molecule, or cDNA molecule produced from the mRNA molecule) encoding an MST1 and/or MST1R polypeptide having a partial loss-of-function, a complete loss-of-function, a predicted partial loss-of-function, or a predicted complete loss-of-function. In any of the embodiments described herein, the MST1 and/or MST1R variant nucleic acid molecule associated with an increased risk of developing IBD and/or PSC can also be any MST1 and/or MST1R missense variant nucleic acid molecule (such as, for example, genomic nucleic acid molecule, mRNA molecule, or cDNA molecule produced from the mRNA molecule).

The nucleotide sequence of an MST1R reference genomic nucleic acid molecule is set forth in SEQ ID NO:1, which is 16,636 nucleotides in length. The first nucleotide recited in SEQ ID NO:1 corresponds to the nucleotide at position 49,903,637 of chromosome 3 (see, hg38_knownGene_ENSG00000164078.12).

Numerous variant genomic nucleic acid molecules of MST1R exist, including, but not limited to (using the human genome reference build GRch38): 3:49903264:CG:C, 3:49903084:C:T, 3:49890026:G:T, 3:49902417:A:G, 3:49902560:A:T, and 3:49903387:G:T. Thus, for example, using the reference genomic nucleotide sequence (SEQ ID NO:1) as a base sequence (with the first nucleotide listed therein designated as position 49,903,637), the first listed variant (3:49903264:CG:C) has a CG dinucleotide replaced with a cytosine (designated the "variant nucleotide") at position 49,903,264, effectively deleting the guanine (designated the "variant position"). In another example, the second listed variant (3:49903084:C:T) has a cytosine replaced with a thymine (designated the "variant nucleotide") at position 49,903,084 (designated the "variant position"). Any of these MST1R predicted loss-of-function variant genomic nucleic acid molecules can be detected in any of the methods described herein.

The nucleotide sequences of MST1R reference mRNA molecules produced through alternative splicing are set forth in SEQ ID NOs:2-10. The variant nucleotides at their respective variant positions for the variant genomic nucleic acid molecules described herein also have corresponding variant nucleotides at their respective variant positions for the variant mRNA molecules based upon the MST1R reference mRNA sequences according to SEQ ID NOs:2-10. Any of these MST1R variant mRNA molecules can be detected in any of the methods described herein.

The nucleotide sequences of MST1R reference cDNA molecules are set forth in SEQ ID NOs:11-19. The variant nucleotides at their respective variant positions for the variant genomic nucleic acid molecules described herein also have corresponding variant nucleotides at their respective variant positions for the variant cDNA molecules based upon the MST1R reference cDNA sequence according to SEQ ID NOs:11-19. Any of these MST1R variant cDNA molecules can be detected in any of the methods described herein.

The amino acid sequences of MST1R reference polypeptide isoforms are set forth in SEQ ID NOs:20-28. Using the translated nucleotide sequence of either the MST1R mRNA or cDNA molecules, the MST1R variant polypeptides have corresponding translated variant amino acids at variant positions (codons). Any of these MST1R variant polypeptides can be detected in any of the methods described herein.

The nucleotide sequence of an MST1 reference genomic nucleic acid molecule is set forth in SEQ ID NO:29, which is 5,107 nucleotides in length. The first nucleotide recited in SEQ ID NO:29 corresponds to the nucleotide at position 49,689,053 of chromosome 3 according to GRCh38/hg38 human genome assembly (see, hg38_knownGene_ENSG00000449682.2).

The nucleotide sequence of the rs3197999 variant genomic nucleic acid molecule is set forth in SEQ ID NO:30. Compared to the reference genomic nucleic acid molecule sequence (SEQ ID NO:29), the nucleotide sequence of the rs3197999 variant genomic nucleic acid molecule (SEQ ID NO:30) comprises a thymine rather than a cytosine at position 4,955. Compared to the reference genomic nucleic acid molecule sequence (SEQ ID NO:29), the nucleotide sequence of the rs3197999 variant genomic nucleic acid molecule (SEQ ID NO:30) comprises a TGC codon rather than a CGC codon at positions 4,955 to 4,957. This MST1 predicted loss-of-function variant genomic nucleic acid molecule can be detected in any of the methods described herein.

The nucleotide sequence of the rs142690032 variant genomic nucleic acid molecule is set forth in SEQ ID NO:37. Compared to the reference genomic nucleic acid molecule sequence (SEQ ID NO:29), the nucleotide sequence of the rs142690032 variant genomic nucleic acid molecule (SEQ ID NO:37) comprises a thymine rather than a cytosine at position 4,675. Compared to the reference genomic nucleic acid molecule sequence (SEQ ID NO:29), the nucleotide sequence of the rs142690032 variant genomic nucleic acid molecule (SEQ ID NO:37) comprises an ACT codon rather than an ACC codon at positions 4,673 to 4,675. This MST1 predicted loss-of-function variant genomic nucleic acid molecule can be detected in any of the methods described herein.

The nucleotide sequence of an MST1 reference mRNA molecule is set forth in SEQ ID NO:31.

The nucleotide sequence of the rs3197999 mRNA molecule is set forth in SEQ ID NO:32. Compared to the reference mRNA molecule sequence (SEQ ID NO:31), the nucleotide sequence of the rs3197999 variant mRNA molecule (SEQ ID NO:32) comprises a uracil rather than a cytosine at position 2,469. Compared to the reference mRNA molecule sequence (SEQ ID NO:31), the nucleotide sequence of the rs3197999 variant mRNA molecule (SEQ ID NO:32) comprises a UGC codon rather than a CGC codon at positions 2,469 to 2,471. This MST1 predicted loss-of-function variant mRNA molecule can be detected in any of the methods described herein.

The nucleotide sequence of the rs142690032 variant mRNA molecule is set forth in SEQ ID NO:38. Compared to the reference mRNA molecule sequence (SEQ ID NO:31), the nucleotide sequence of the rs142690032 variant mRNA molecule (SEQ ID NO:38) comprises a uracil rather than a cytosine at position 2,313. Compared to the reference mRNA molecule sequence (SEQ ID NO:31), the nucleotide sequence of the rs142690032 variant mRNA molecule (SEQ ID NO:38) comprises an ACU codon rather than an ACC codon at positions 2,311 to 2,313. This MST1 predicted loss-of-function variant genomic nucleic acid molecule can be detected in any of the methods described herein.

The nucleotide sequence of an MST1 reference cDNA molecule is set forth in SEQ ID NO:33.

The nucleotide sequence of the rs3197999 cDNA molecule is set forth in SEQ ID NO:34. Compared to the reference cDNA molecule sequence (SEQ ID NO:33), the nucleotide sequence of the rs3197999 variant cDNA molecule (SEQ ID NO:33) comprises a thymine rather than a cytosine at position 2,469. Compared to the reference cDNA molecule sequence (SEQ ID NO:33), the nucleotide sequence of the rs3197999 variant cDNA molecule (SEQ ID NO:34) comprises a TGC codon rather than a CGC codon at positions 2,469 to 2,471. This MST1 predicted loss-of-function variant cDNA molecule can be detected in any of the methods described herein.

The nucleotide sequence of the rs142690032 variant cDNA molecule is set forth in SEQ ID NO:39. Compared to the reference cDNA molecule sequence (SEQ ID NO:33), the nucleotide sequence of the rs142690032 variant cDNA molecule (SEQ ID NO:39) comprises a thymine rather than a cytosine at position 2,313. Compared to the reference cDNA molecule sequence (SEQ ID NO:33), the nucleotide sequence of the rs142690032 variant cDNA molecule (SEQ ID NO:39) comprises an ACT codon rather than an ACC codon at positions 2,311 to 2,313. This MST1 predicted loss-of-function variant cDNA molecule can be detected in any of the methods described herein.

The amino acid sequence of a reference MST1 polypeptide is set forth in SEQ ID NO:35 and is 725 amino acids long.

The amino acid sequence of the rs3197999 variant MST1 polypeptide is set forth in SEQ ID NO:36 and is 725 amino acids long. The SNP in the underlying nucleic acid molecules results in the substitution of the arginine at amino acid position 703 of the reference MST1 polypeptide (SEQ ID NO:35) with a cytosine. This rs3197999 variant MST1 polypeptide is referred to herein as Arg703Cys MST1 polypeptide.

The amino acid sequence of the rs142690032 variant MST1 polypeptide is set forth in SEQ ID NO:40 and is 650 amino acids long. The SNP in the underlying nucleic acid molecules results in a gain of a stop codon at the position corresponding to position 651 according to SEQ ID NO:35 (replacing an arginine). This results in expression of a variant MST1 polypeptide truncated at a position corresponding to position 650 according to SEQ ID NO:35. This rs142690032 variant MST1 polypeptide is referred to herein as Arg651STOP MST1 polypeptide. This variant MST1 polypeptide does not comprises the amino acids at positions corresponding to positions 651 to 725 of the reference MST1 polypeptide (SEQ ID NO:35).

In any of the embodiments described herein, the variant MST1 nucleic acid molecule or polypeptide can be or encode Arg703Cys or Arg651STOP. In any of the embodiments described herein, the variant MST1 nucleic acid molecule or polypeptide can be or encode Arg703Cys. In any of the embodiments described herein, the variant MST1 nucleic acid molecule or polypeptide can be or encode Arg651STOP.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure provides methods of treating a patient having IBD, the method comprising administering to the patient an agonist of the MST1/MST1R pathway. In any of the embodiments described herein, the IBD is ulcerative colitis (US) or Crohn's disease (CD). In any of the embodiments described herein, the CD is jejunoileitis, ileitis, ileocolitis, or Crohn's colitis, or any combination thereof. In any of the embodiments described herein, the UC is ulcerative proctitis, left-sided colitis, or extensive colitis, or any combination thereof.

Symptoms of Crohn's disease include, but are not limited to, frequent and/or recurring diarrhea, rectal bleeding, unexplained weight loss, fever, abdominal pain, cramping, fatigue, a feeling of low energy, and reduced appetite. Symptoms of ulcerative proctitis include, but are not limited to, rectal bleeding, rectal pain, and urgency in bowel movements. Symptoms of left-sided colitis include, but are not limited to, loss of appetite, weight loss, bloody diarrhea, and pain on the left side of the abdomen. Symptoms of extensive colitis include, but are not limited to, loss of appetite, bloody diarrhea, abdominal pain, and weight loss.

The present disclosure also provides methods of treating a patient having PSC, the method comprising administering to the patient an agonist of the MST1/MST1R pathway. In any of the embodiments described herein, the PSC is early stage PSC (e.g., stage 1 according to Ludwig et al., Hepatology, 1981, 1, 632-640). In any of the embodiments described herein, the PSC is late stage PSC (e.g., stage 4 according to Ludwig et al., Hepatology, 1981, 1, 632-640). In any of the embodiments described herein, the PSC is at any disease stage (e.g., stage 4 according to Ludwig et al., Hepatology, 1981, 1, 632-640). In some embodiments, the human subject is a female. In some embodiments, the human subject is a male.

Symptoms of PSC include, but are not limited to, jaundice, non-specific upper abdominal pain, fatigue, pruritus, right upper quadrant, pain yellowing of the skin, mucous membranes, and whites of the eyes (obstructive jaundice). Additional symptoms include a general feeling of ill health (malaise); abdominal pain, especially the upper right portion of the abdomen; nausea; dark urine; light-colored stools; unintended weight loss, and/or abnormal enlargement of the liver (hepatomegaly) and/or spleen (splenomegaly).

In any of the embodiments described herein, the agonist of the MST1/MST1R pathway is an MST1 agonist or an MST1R agonist. In some embodiments, the MST1 agonist and/or the MST1R agonist comprises a protein, a nucleic acid molecule, or a small molecule. In some embodiments, the protein is an antibody to MST1 or MST1R.

In some embodiments, the MST1 agonist is a protein, such as recombinant MST1. In some embodiments, the recombinant MST1 is a fusion protein comprising MST1 or a fragment thereof fused to a heterologous protein, for example an antibody or a fragment thereof, such as Fc fragment (e.g., Mst1-Fc). In some embodiments, the MST1 agonist is chelerythrine, recombinant Tumor Necrosis Factor Receptor Associated Factor 2 (TRAF2), or curcumin. In some embodiments, the MST1 agonist is a protease chosen from Hepatocyte Growth Factor Activator (HGFA), matriptase, hepsin, TMPRSS11D (Human Airway Prypsin-like protease; HAT), clotting factor XIIa, clotting factor Xia, and kallikrein.

In some embodiments, the MST1R agonist is recombinant Macrophage Scavenger Receptor 1 (MSR1), recombinant Hepatocyte Growth Factor-Like protein (HGFL), or recombinant Androgen Receptor (AR). In some embodiments, the MST1R agonist is an antibody chosen from mAb Zt/g4, mAb Zt/c1, mAb Zt/f2, mAb Zt/64, mAb 3F12, mAb B9, and mAb 1G4.

In any of the embodiments described herein, the patient having IBD and/or PSC can be treated with additional therapeutic agents. Examples of therapeutic agents that treat or inhibit IBD include, but are not limited to, aminosalicylates (such as COLAZAL® (balsalazide), ASACOL®, APRISO®, LIALDA®, and PENTASA® (mesalamine), DIPENTUM® (olsalazine), and AZULFIDINE® (sulfasalazine)); corticosteroids; immune modifying agents (such as IMURAN® (azathioprine), RHEUMATREX® (methotrexate), and PURINETHOL® (6-mercaptopurine (6-MP)); and antibodies (such as REMICADE® (infliximab), RENFLEXIS® (infliximab-abda), INFLECTRA® (infliximab-dyyb), HUMIRA® (dalimumab), AMJEVITA® (adalimumab-atto), CIMZIA® (certolizumab), TYSABRI® (natalizumab), ENTYVIO® (vedolizumab), STELARA® (ustekinumab), SIMPONI® and SIMPONI® ARIA (golimumab)), and recombinant MST1, or any combination thereof. Examples of therapeutic agents that treat or inhibit IBD include, but are not limited to, aminosalicylates (such as balsalazide, mesalamine, olsalazine, and sulfasalazine); corticosteroids; immune modifying agents (such as azathioprine, methotrexate, and 6-mercaptopurine (6-MP)); and antibodies (such as infliximab, infliximab-abda, infliximab-dyyb, dalimumab, adalimumab-atto, certolizumab, natalizumab, vedolizumab, ustekinumab, golimumab), and recombinant MST1, or any combination thereof. Examples of therapeutic agents that treat or inhibit PSC include, but are not limited to, medications to reduce itching and jaundice, antibiotics to treat infections, immunosuppressants, cholecystogues, and vitamin supplements, or any combination thereof.

Administration of the therapeutic agents that treat or inhibit IBD or PSC can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a patient can receive therapy for a prolonged period of time such as, for example, 6 months, 1 year, or more.

Administration of the therapeutic agents that treat or inhibit IBD or PSC can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in IBD, PSC, or both, a decrease/reduction in the severity of IBD, PSC, or both (such as, for example, a reduction or inhibition of development of IBD, PSC, or both), a decrease/reduction in symptoms and IBD-related effects, PSC-related effects, or both, delaying the onset of symptoms and IBD-related effects, PSC-related effects, or both, reducing the severity of symptoms of IBD-related effects, PSC-related effects, or both, reducing the severity of an acute episode, reducing the number of symptoms and IBD-related effects, PSC-related effects, or both, reducing the latency of symptoms and IBD-related effects, PSC-related effects, or both, an amelioration of symptoms and IBD-related effects, PSC-related effects, or both, reducing secondary symptoms, reducing secondary infections, preventing relapse to IBD, PSC, or both, decreasing the number or frequency of relapse episodes, increasing latency between symptomatic episodes, increasing time to sustained progression, speeding recovery, and/or increasing efficacy of or decreasing resistance to alternative therapeutics, following administration of the agent or composition comprising the agent. A prophylactic effect may comprise a complete or partial avoidance/inhibition or a delay of IBD, PSC, or both development/progression (such as, for example, a complete or partial avoidance/inhibition or a delay) following administration of a therapeutic protocol. Treatment of IBD, PSC, or both encompasses the treatment of patients already diagnosed as having any form of IBD, PSC, or both at any clinical stage or manifestation, the delay of the onset or evolution or aggravation or deterioration of the symptoms or signs of IBD, PSC, or both, and/or preventing and/or reducing the severity of IBD, PSC, or both.

In any of the embodiments described herein, the methods can further comprise detecting the presence or absence of an MST1 and/or MST1R variant nucleic acid molecule or variant polypeptide associated with an increased risk of developing IBD and/or PSC in a biological sample from the patient. It is understood that gene sequences within a population and mRNA molecules encoded by such genes can vary due to polymorphisms such as single-nucleotide polymorphisms. The sequences provided herein for the MST1 and/or MST1R variant nucleic acid molecules disclosed herein are only exemplary sequences. Other sequences for the MST1 and/or MST1R variant nucleic acid molecules are also possible.

The MST1 and/or MST1R variant nucleic acid molecule or variant polypeptide associated with an increased risk of developing IBD and/or PSC can be any MST1 and/or MST1R predicted loss-of-function variant or MST1 and/or MST1R missense variant, such as any of those described herein. For example, in any of the embodiments described herein, the MST1 variant nucleic acid molecule associated with an increased risk of developing IBD and/or PSC is Arg703Cys or Arg651STOP. In some embodiments, the MST1 variant nucleic acid molecule associated with an increased risk of developing IBD and/or PSC is Arg703Cys. In some embodiments, the MST1 variant nucleic acid molecule associated with an increased risk of developing IBD and/or PSC is Arg651STOP. In addition, in any of the embodiments described herein, the MST1R variant nucleic acid molecule associated with an increased risk of developing IBD and/or PSC can be 3:49903264:CG:C, 3:49903084:C:T, 3:49890026:G:T, 3:49902417:A:G, 3:49902560:A:T, or 3:49903387:G:T, or an mRNA molecule produced therefrom, or a cDNA molecule produced from the mRNA molecule. In any of the embodiments described herein, the MST1R variant nucleic acid molecule associated with an increased risk of developing IBD and/or PSC is 3:49903264:CG:C, or an mRNA molecule produced therefrom, or a cDNA molecule produced from the mRNA molecule. In any of the embodiments described herein, the MST1R variant nucleic acid molecule associated with an increased risk of developing IBD and/or PSC is 3:49903084:C:T, or an mRNA molecule produced therefrom, or a cDNA molecule produced from the mRNA molecule. In any of the embodiments described herein, the MST1R variant nucleic acid molecule associated with an increased risk of developing IBD and/or PSC is 3:49890026:G:T, or an mRNA molecule produced therefrom, or a cDNA molecule produced from the mRNA molecule. In any of the embodiments described herein, the MST1R variant nucleic acid molecule associated with an increased risk of developing IBD and/or PSC is 3:49902417:A:G, or an mRNA molecule produced therefrom, or a cDNA molecule produced from the mRNA molecule. In any of the embodiments described herein, the MST1R variant nucleic acid molecule associated with an increased risk of developing IBD and/or PSC is 3:49902560:A:T, or an mRNA molecule produced therefrom, or a cDNA molecule produced from the mRNA molecule. In any of the embodiments described herein, the MST1R variant nucleic acid molecule associated with an increased risk of developing IBD and/or PSC can be 3:49903387:G:T, or an mRNA molecule produced therefrom, or a cDNA molecule produced from the mRNA molecule.

In some embodiments, detecting the presence or absence of the MST1 and/or MST1R variant nucleic acid molecule or variant polypeptide associated with an increased risk of developing IBD and/or PSC comprises determining whether the patient has an MST1 and/or MST1R variant genomic nucleic acid molecule associated with an increased risk of developing IBD and/or PSC, an MST1 and/or MST1R variant mRNA molecule associated with an increased risk of developing IBD and/or PSC, an MST1 and/or MST1R variant cDNA molecule produced from the mRNA molecule, and/or an MST1 and/or MST1R variant polypeptide associated with an increased risk of developing IBD and/or PSC. In some embodiments, such determination is carried out by obtaining or having obtained a biological sample from the patient, and performing or having performed an assay on the biological sample to determine whether the patient has an MST1 and/or MST1R variant nucleic acid molecule or variant polypeptide associated with an increased risk of developing IBD and/or PSC. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

Determining whether a human has an MST1 and/or MST1R variant nucleic acid molecule or an MST1 and/or MST1R variant polypeptide associated with an increased risk of developing IBD and/or PSC in a biological sample can be carried out by any of the methods described herein. In some embodiments, the detecting step, determining step, or assay is carried out in vitro. In some embodiments, these methods can be carried out in situ. In some embodiments, these methods can be carried out in vivo. In any of these embodiments, the nucleic acid molecule can be present within a cell obtained from the human subject. In some embodiments, the assay is a genotyping assay for nucleic acid molecules. In some embodiments, the assay is an immunoassay for polypeptides.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. In some embodiments, the biological sample comprises a cell lysate. Such methods can further comprise obtaining a biological sample from the subject. The sample used in the methods disclosed herein will vary based on the assay format, nature of the detection method, and the tissues, cells, or extracts that are used as the sample. A biological sample can be processed differently depending on the assay being employed. For example, when detecting any MST1 and/or MST1R variant nucleic acid molecule, preliminary processing designed to isolate or enrich the sample for the genomic DNA can be employed. A variety of known techniques may be used for this purpose. When detecting the level of any MST1 and/or MST1R variant mRNA, different techniques can be used enrich the biological sample with mRNA. Various methods to detect the presence or level of a mRNA or the presence of a particular variant genomic DNA locus can be used.

In some embodiments, the methods can further comprise determining the patient's aggregate burden of having MST1 and/or MST1R variant genomic nucleic acid molecules associated with an increased risk of developing IBD and/or PSC, MST1 and/or MST1R variant mRNA molecules associated with an increased risk of developing IBD and/or PSC, MST1 and/or MST1R variant cDNA molecules produced from the mRNA molecules, and/or MST1 and/or MST1R variant polypeptides associated with an increased risk of developing IBD and/or PSC. The aggregate burden is the sum of all rare variants in the MSTR1 gene, which is run in an association test with IBD. The result of the association test suggests that rare loss-of-function and missense variants of MST1R are associated with increased odds of IBD. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the detecting step, determining step, or assay comprises sequencing at least a portion of the nucleotide sequence of the MST1 and/or MST1R nucleic acid molecule in the biological sample. The sequenced portion comprises a position corresponding to a predicted loss-of-function variant position. When a variant nucleotide at the predicted loss-of-function variant position is detected, the MST1 and/or MST1R nucleic acid molecule in the biological sample is an MST1 and/or MST1R predicted loss-of-function variant nucleic acid molecule. The predicted loss-of-function variant position within any particular MST1 and/or MST1R nucleic acid molecule is the one or more positions of the variant nucleotide sequence that are different compared to the nucleotide sequence of the corresponding reference nucleic acid molecule. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the detecting step, determining step, or assay comprises: contacting the biological sample with a primer hybridizing to a portion of the nucleotide sequence of the MST1 and/or MST1R nucleic acid molecule that is proximate to a predicted loss-of-function variant position, extending the primer at least through the predicted loss-of-function variant position, and determining whether the extension product of the primer comprises a variant nucleotide at the predicted loss-of-function variant position. In some embodiments, the detecting step, determining step, or assay comprises sequencing the entire nucleic acid molecule. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the detecting step, determining step, or assay comprises sequencing at least a portion of the nucleotide sequence of the MST1 and/or MST1R nucleic acid molecule in the biological sample. The sequenced portion comprises a position corresponding to a missense variant position. When a variant nucleotide at the missense variant position is detected, the MST1 and/or MST1R nucleic acid molecule in the biological sample is an MST1 and/or MST1R missense variant nucleic acid molecule. The missense variant position within any particular MST1 and/or MST1R nucleic acid molecule is the one or more positions of the variant nucleotide sequence that are different compared to the nucleotide sequence of the corresponding reference nucleic acid molecule. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the detecting step, determining step, or assay comprises contacting the biological sample with a primer hybridizing to a portion of the nucleotide sequence of the MST1 and/or MST1R nucleic acid molecule that is proximate to a missense variant position, extending the primer at least through the missense variant position, and determining whether the extension product of the primer comprises a variant nucleotide at the missense variant position. In some embodiments, the detecting step, determining step, or assay comprises sequencing the entire nucleic acid molecule. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the assay comprises contacting the biological sample with a primer, such as an alteration-specific primer, that specifically hybridizes to an MST1 or MST1R variant genomic sequence, variant mRNA sequence, or variant cDNA sequence and not the corresponding MST1 or MST1R reference sequence under stringent conditions. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, only an MST1 and/or MST1R genomic nucleic acid molecule is analyzed. In some embodiments, only an MST1 and/or MST1R mRNA is analyzed. In some embodiments, only an MST1 and/or MST1R cDNA obtained from MST1 and/or MST1R mRNA is analyzed. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

Illustrative examples of nucleic acid sequencing techniques include, but are not limited to, chain terminator (Sanger) sequencing and dye terminator sequencing. In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the detecting step, determining step, or assay comprises amplifying at least a portion of the MST1 and/or MST1R nucleic acid molecule, wherein the portion comprises a predicted loss-of-function variant position, labeling the amplified nucleic acid molecule with a detectable label, contacting the labeled nucleic acid molecule with a support comprising an alteration-specific probe, wherein the alteration-specific probe comprises a nucleotide sequence which hybridizes under stringent conditions to the predicted loss-of-function variant position, and detecting the detectable label. In some embodiments, the nucleic acid molecule in the sample is mRNA and the mRNA is reverse-transcribed into a cDNA prior to the amplifying step. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the detecting step, determining step, or assay comprises contacting the nucleic acid molecule in the biological sample with an alteration-specific probe comprising a detectable label, wherein the alteration-specific probe comprises a nucleotide sequence which hybridizes under stringent conditions to a predicted loss-of-function variant position, and detecting the detectable label. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the detecting step, determining step, or assay comprises amplifying at least a portion of the MST1 and/or MST1R nucleic acid molecule, wherein the portion comprises a missense variant position, labeling the amplified nucleic acid molecule with a detectable label, contacting the labeled nucleic acid molecule with a support comprising an alteration-specific probe, wherein the alteration-specific probe comprises a nucleotide sequence which hybridizes under stringent conditions to the missense variant position, and detecting the detectable label. In some embodiments, the nucleic acid molecule in the sample is mRNA and the mRNA is reverse-transcribed into a cDNA prior to the amplifying step. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the detecting step, determining step, or assay comprises contacting the nucleic acid molecule in the biological sample with an alteration-specific probe comprising a detectable label, wherein the alteration-specific probe comprises a nucleotide sequence which hybridizes under stringent conditions to a missense variant position, and detecting the detectable label. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

The alteration-specific probes or alteration-specific primers described herein comprise a nucleic acid sequence which is complementary to and/or hybridizes, or specifically hybridizes, to an MST1 or MST1R predicted loss-of-function variant nucleic acid molecule, or an MST1 or MST1R missense variant nucleic acid molecule, or the complement thereof. In some embodiments, the alteration-specific probes or alteration-specific primers comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 nucleotides. In some embodiments, the alteration-specific probes or alteration-specific primers comprise or consist of at least 15 nucleotides. In some embodiments, the alteration-specific probes or alteration-specific primers comprise or consist of at least 15 nucleotides to at least about 35 nucleotides. In some embodiments, alteration-specific probes or alteration-specific primers hybridize to MST1 or MST1R predicted loss-of-function variant genomic nucleic acid molecules, MST1R predicted loss-of-function variant mRNA molecules, and/or MST1R predicted loss-of-function variant cDNA molecules under stringent conditions. In some embodiments, alteration-specific probes or alteration-specific primers hybridize to MST1 or MST1R missense variant genomic nucleic acid molecules, MST1R missense variant mRNA molecules, and/or MST1R missense variant cDNA molecules under stringent conditions. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the assay comprises contacting the biological sample with a probe, such as an alteration-specific probe, that specifically hybridizes to an MST1 or MST1R variant genomic sequence, variant mRNA sequence, or variant cDNA sequence and not the corresponding MST1 or MST1R reference sequence under stringent conditions, and determining whether hybridization has occurred. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

In some embodiments, the methods utilize probes and primers of sufficient nucleotide length to bind to the target nucleotide sequence and specifically detect and/or identify a polynucleotide comprising an MST1 or MST1R variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, labeled primers or probes directed against purified DNA, amplified DNA, and fixed cell preparations (fluorescence in situ hybridization (FISH)) can be used for detection. In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, detecting the presence of a human MST1 and/or MST1R variant polypeptide comprises performing an assay on a sample obtained from a human subject to determine whether an MST1 and/or MST1R polypeptide in the subject contains one or more variations that causes the polypeptide to have a loss-of-function (partial or complete) or predicted loss-of-function (partial or complete), or be produced from a missense variant nucleic acid molecule. In some embodiments, the assay comprises sequencing at least a portion of the MST1 and/or MST1R polypeptide that comprises a variant position. In some embodiments, the detecting step comprises sequencing the entire polypeptide. Identification of a variant amino acid at the variant position of the MST1 and/or MST1R polypeptide indicates that the MST1 and/or MST1R polypeptide is an MST1 and/or MST1R predicted loss-of-function polypeptide, or is produced from a missense variant nucleic acid molecule. In some embodiments, the assay comprises an immunoassay for detecting the presence of a variant polypeptide. Detection of a variant amino acid at the variant position of the MST1 or MST1R polypeptide indicates that the MST1 or MST1R polypeptide is a variant MST1 or MST1R polypeptide. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

The probes and/or primers (including alteration-specific probes and alteration-specific primers) described herein comprise or consist of from about 15 to about 100, from about 15 to about 35 nucleotides. In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers (including alteration-specific probes and alteration-specific primers) specifically hybridize to any of the nucleic acid molecules disclosed herein under stringent conditions. In the context of the disclosure "specifically hybridizes" means that the probe or primer (including alteration-specific probes and alteration-specific primers) does not hybridize to a nucleic acid sequence encoding an MST1R reference genomic nucleic acid molecule, an MST1R reference mRNA molecule, and/or an MST1R reference cDNA molecule. In some embodiments, the probes (such as, for example, an alteration-specific probe) comprise a label. In some embodiments, the label is a fluorescent label, a radiolabel, or biotin.

The present disclosure also provides methods of identifying a human subject having an increased risk of developing IBD. The methods comprise determining or having determined whether the subject has any one or more of the MST1R predicted loss-of-function variant nucleic acid molecule or polypeptide produced therefrom described herein. The methods can also comprise determining or having determined whether the subject has any one or more of the MST1R missense variant nucleic acid molecule or polypeptide produced therefrom described herein. When the subject has an MST1R predicted loss-of-function variant nucleic acid molecule, or an MST1R missense variant nucleic acid molecule, or polypeptide produced therefrom, the subject has an increased risk of developing IBD. In some embodiments, when a human subject is identified as having an increased risk of developing IBD, the human subject is further treated with a therapeutic agent that treats or inhibits IBD and/or an MST1/MST1R pathway agonist, as described herein. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

The present disclosure also provides methods of identifying a human subject having an increased risk of developing PSC. The methods comprise determining or having determined whether the subject has any one or more of the MST1R predicted loss-of-function variant nucleic acid molecule or polypeptide produced therefrom described herein. The methods can also comprise determining or having determined whether the subject has any one or more of the MST1R missense variant nucleic acid molecule or polypeptide produced therefrom described herein. When the subject has an MST1R predicted loss-of-function variant nucleic acid molecule, or an MST1R missense variant nucleic acid molecule, or polypeptide produced therefrom, the subject has an increased risk of developing PSC. In some embodiments, when a human subject is identified as having an increased risk of developing PSC, the human subject is further treated with a therapeutic agent that treats or inhibits PSC and/or an MST1/MST1R pathway agonist, as described herein. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

The present disclosure also provides methods of diagnosing IBD in a human subject. The methods comprise determining or having determined whether the subject has any one or more of the MST1R predicted loss-of-function variant nucleic acid molecule or polypeptide produced therefrom described herein. The methods can also comprise determining or having determined whether the subject has any one or more of the MST1R missense variant nucleic acid molecule or polypeptide produced therefrom described herein. When the subject has an MST1R predicted loss-of-function variant nucleic acid molecule, or an MST1R missense variant nucleic acid molecule, or polypeptide produced therefrom, and has one or more symptoms of IBD, the subject is diagnosed as having IBD. In some embodiments, when a human subject is identified as having IBD, the human subject is further treated with a therapeutic agent that treats or inhibits IBD and/or an MST1/MST1R pathway agonist, as described herein. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

The present disclosure also provides methods of diagnosing PSC in a human subject. The methods comprise determining or having determined whether the subject has any one or more of the MST1R predicted loss-of-function variant nucleic acid molecule or polypeptide produced therefrom described herein. The methods can also comprise determining or having determined whether the subject has any one or more of the MST1R missense variant nucleic acid molecule or polypeptide produced therefrom described herein. When the subject has an MST1R predicted loss-of-function variant nucleic acid molecule, or an MST1R missense variant nucleic acid molecule, or polypeptide produced therefrom, and has one or more symptoms of IBD, the subject is diagnosed as having PSC. In some embodiments, when a human subject is identified as having PSC, the human subject is further treated with a therapeutic agent that treats or inhibits PSC and/or an MST1/MST1R pathway agonist, as described herein. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

The present disclosure also provides molecular complexes comprising any of the MST1R variant nucleic acid molecules (genomic nucleic acid molecules, mRNA molecules, or cDNA molecules), or complement thereof, described herein and any of the alteration-specific primers or alteration-specific probes described herein. In some embodiments, the MST1R variant nucleic acid molecules (genomic nucleic acid molecules, mRNA molecules, or cDNA molecules), or complement thereof, in the molecular complexes are single-stranded. In some embodiments, the MST1R variant nucleic acid molecule is any of the variant genomic nucleic acid molecules described herein. In some embodiments, the MST1R variant nucleic acid molecule is any of the variant mRNA molecules described herein. In some embodiments, the MST1R variant nucleic acid molecule is any of the variant cDNA molecules described herein. In some embodiments, the molecular complex comprises any of the MST1R variant nucleic acid molecules (genomic nucleic acid molecules, mRNA molecules, or cDNA molecules), or complement thereof, described herein and any of the alteration-specific primers described herein. In some embodiments, the molecular complex comprises any of the MST1R variant nucleic acid molecules (genomic nucleic acid molecules, mRNA molecules, or cDNA molecules), or complement thereof, described herein and any of the alteration-specific probes described herein. In some embodiments, the molecular complex comprises a non-human polymerase. In some embodiments, the MST1 variant nucleic acid molecule is Arg703Cys or Arg651STOP. In some embodiments, the MST1 variant nucleic acid molecule is Arg703Cys. In some embodiments, the MST1 variant nucleic acid molecule is Arg651STOP. In some embodiments, the MST1R variant nucleic acid molecule is any of the MST1R variant nucleic acid molecules described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Aggregate Burden

Figure 2:
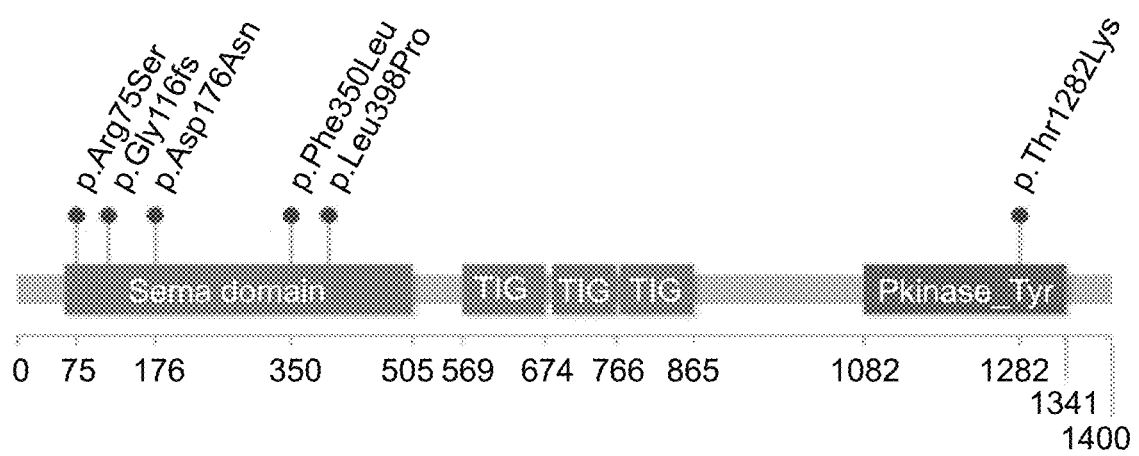
FIG. 2 shows MST1R protein domains highlighting loss-of-function and predicted-deleterious missenses associated with IBD and found in Table 1.

Table 1 shows that the aggregate of all rare predicted loss-of-function (pLOF) and predicted missense variants significantly associates with increased odds of IBD among exome-wide analysis of 4,319 IBD cases and 4,388 cases within the University of Kiel IBD cohort (odds ratio 2.99; p-value 1.62E-06). Table 1 also shows that the aggregate of all rare predicted loss-of-function variants associates with increased odds of IBD among exome-wide analysis of 4,319 IBD cases and 4,388 cases within the University of Kiel IBD cohort (odds ratio 3.90; p-value 2.15E-04) (see also, FIG. 2).

TABLE 1

| Mask | # Cases | Case RR:RA:AA | # Controls | Control RR:RA:AA | AAF | OR (95% CI) | P-value |
|---|---|---|---|---|---|---|---|
| pLoF and predicted deleterious missense variants (M3.1) | 4319 | 4234:85:0 | 4388 | 4359:29:0 | 0.0065 | 2.99 (1.91, 4.68) | 1.62E-06 |
| pLoF variants (M1.1) | 4319 | 4283:36:0 | 4388 | 4380:8:0 | 0.0025 | 3.90 (1.89, 8.03) | 2.15E-04 |

Table 2 shows that the association of the aggregate of all predicted loss-of-function variants replicates in UK Biobank IBD cohort comprised of 396 cases and 137,000 controls at an odds ratio of 2.22 (p-value 0.018) and 3.21 (p-value 0.011), respectively. Table 2 also shows that the association of the aggregate of all rare predicted loss-of-function and predicted missense variants and the aggregate of all rare predicted loss-of-function variants replicates in UK Biobank IBD cohort comprised of 494 cases and 30,000 controls at an odds ratio of 2.21 (p-value 0.048).

TABLE 2

| Cohort | Mask | Case RR:RA:AA | Control RR:RA:AA | AAF | OR (95% CI) | P-value |
|---|---|---|---|---|---|---|
| UKB 150K | pLoF and predicted deleterious missense variants (M3.1) | 387:9:0 | 136174:1414:0 | 0.0190 | 2.22 (1.15, 4.32) | 1.8E-2 |
|  | pLoF variants (M1.1) | 391:5:0 | 137044:544:0 | 0.0035 | 3.21 (1.30, 7.90) | 1.1E-2 |
| GHS 60K | pLoF variants (M1.1) | 488:6:0 | 30978:189:0 | 0.0031 | 2.21 (1.01, 4.87) | 4.8E-2 |

Figure 10:
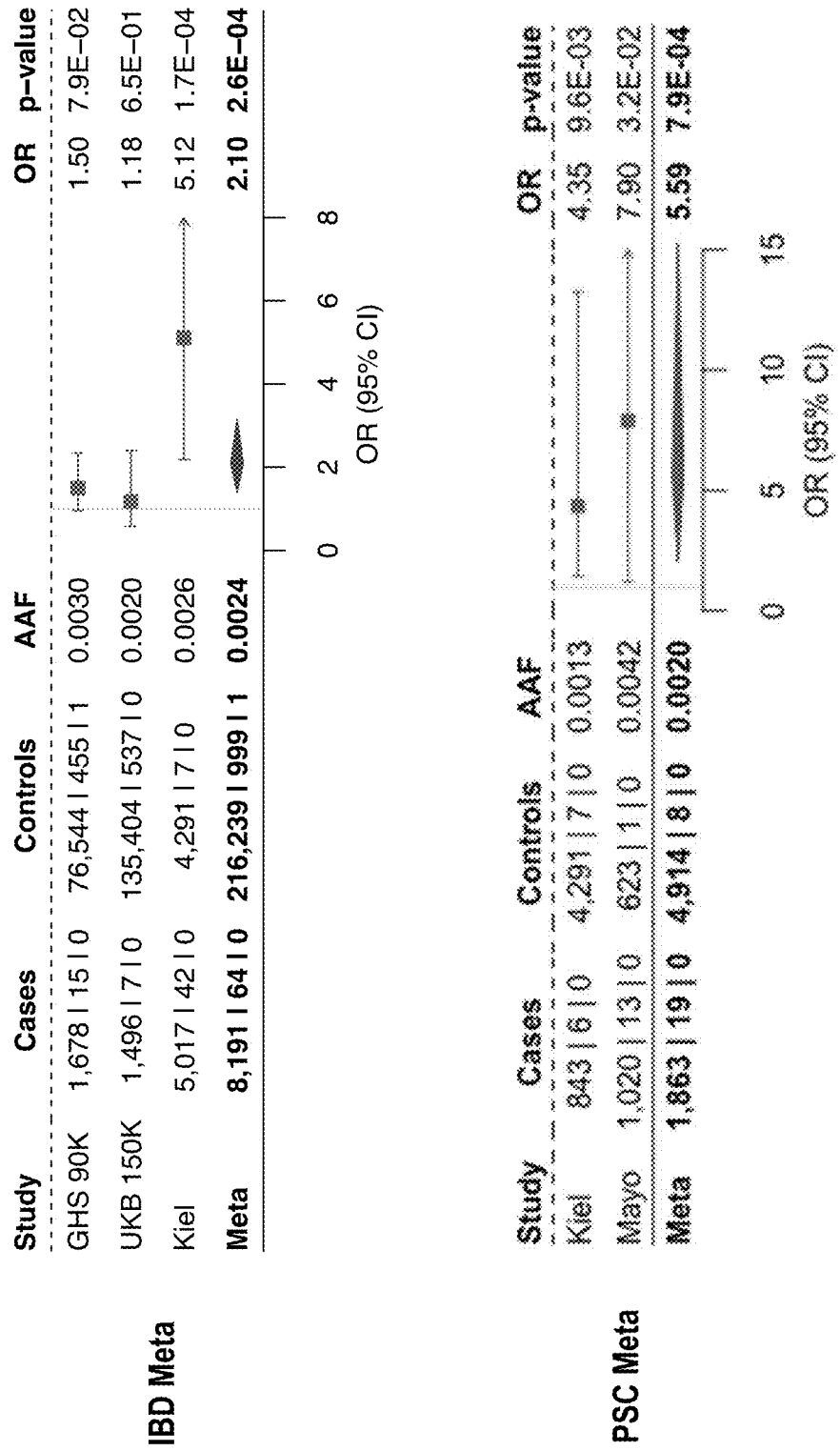
FIG. 10 shows meta analysis of MST1R predicted loss of function with gene burden associations to increased odds of IBD and PSC.

Meta-analysis confirmed this large-effect, rare-variant associations between rare, loss-of-function variants in MST1R to Crohn's (OR=3.12) and PSC (OR=5.59) (see, FIG. 10).

The association of the individual MST1R variants with Crohn's disease is shown in Table 3.

TABLE 3

| Variant | rsID HGVS p. | Case RR:RA:AA | Control RR:RA:AA | CD OR (95% CI) | p-value | AAF |
|---|---|---|---|---|---|---|
| 3:49903264:CG:C | rs758062275 p.Gly116fs | 4,307:13:0 | 4,388:0:0 | 27.47 (4.11, 183.49) | 6.30E-04 | 0.0007 |
| 3:49903084:C:T | rs151106960 p.Asp176Asn | 4,310:10:0 | 4,386:2:0 | 4.27 (0.97, 18.85) | 5.56E-02 | 0.0007 |
| 3:49890026:G:T | rs369707898 p.Thr1282Lys | 4,316:4:0 | 4,387:1:0 | 3.05 (0.48, 19.18) | 2.38E-01 | 0.0003 |
| 3:49902417:A:G | rs199980524 p.Leu398Pro | 4,316:4:0 | 4,386:2:0 | 1.83 (0.53, 6.30) | 3.41E-01 | 0.0003 |
| 3:49902560:A:T | rs199531010 p.Phe350Leu | 4,317:3:0 | 4,385:3:0 | 1.02 (0.96, 1.07) | 5.68E-01 | 0.0003 |
| 3:49903387:G:T | rs35887539 p.Arg75Ser | 4,317:3:0 | 4,386:2:0 | 1.42 (0.02, 98.94) | 8.71E-01 | 0.0003 |

Example 2: Mouse Model of IBD (Prophetic Example)

The effect of the loss of MST1R signaling on the increased risk in IBD mouse models will also be determined. MST1R KO mice will be generated, and challenged in mouse models of IBD. It is anticipated that mice lacking MST1R will be more susceptible to mouse models of IBD. In addition, MST1R transgenic mice that have constitutive MST1R signaling will be generated. It is anticipated that these mice will also be protected in mouse models of IBD.

In vitro experiments will also be performed to determine whether MST1 protein expressing rs3197999 will bind and signal through MST1R. Recombinant protein expressing the MST1 missense rs3197999 will be generated, and macrophage cell lines expressing normal MST1R will be treated with this protein and wildtype protein. Through measurements of signaling downstream of MST1R phospho-AKT/PI3K signaling, it will be determined whether rs3197999 MST1 protein is able to activate MST1R signaling as compared to wildtype MST1 protein. In addition, macrophage cell lines that express MST1R loss-of-function/missense variants will be generated to determine if these mutant proteins can signal by measuring downstream phospho-AKT/PI3K signaling molecules in the presence of exogenous wildtype MST1 ligand.

Example 3: Novel MST1pLoF Mutation is Associated with IBD and PSC

A common MST1 missense variant (r53197999) has been associated with increased odds of IBD and PSC; MST1 rs3197999/p.Arg703Cys (29% allele frequency) has been associated with reduced serum MST1 protein levels (Table 4).

TABLE 4

| Phenotype | Cases RR:RA:AA | Controls RR:RA:AA | Het OR (95% CI) | Hom OR (95% CI) | p-value |
|---|---|---|---|---|---|
| IBD Meta Analysis | 6,009:4922:1137 | 110,756:86,514:16,720 | 1.07 (1.02, 1.12) | 1.37 (1.27, 1.48) | 9.40E−05 |
| Crohn's Meta Analysis | 2,719:2,303:581 | 98,121:76,930:14,988 | 1.08 (1.02, 1.14) | 1.40 (1.27, 1.53) | 2.40E−08 |
| UC Meta Analysi | 1,430:1,181:297 | 98,061:76,888:14,972 | 1.05 (0.97, 1.14) | 1.36 (1.20, 1.54) | 1.20E−04 |
| PSC Meta Analysis | 817:822:243 | 2,542:2,006:374 | 1.27 (1.14, 1.43) | 2.02 (1.68, 2.43) | 9.90E−07 |

Figure 3:
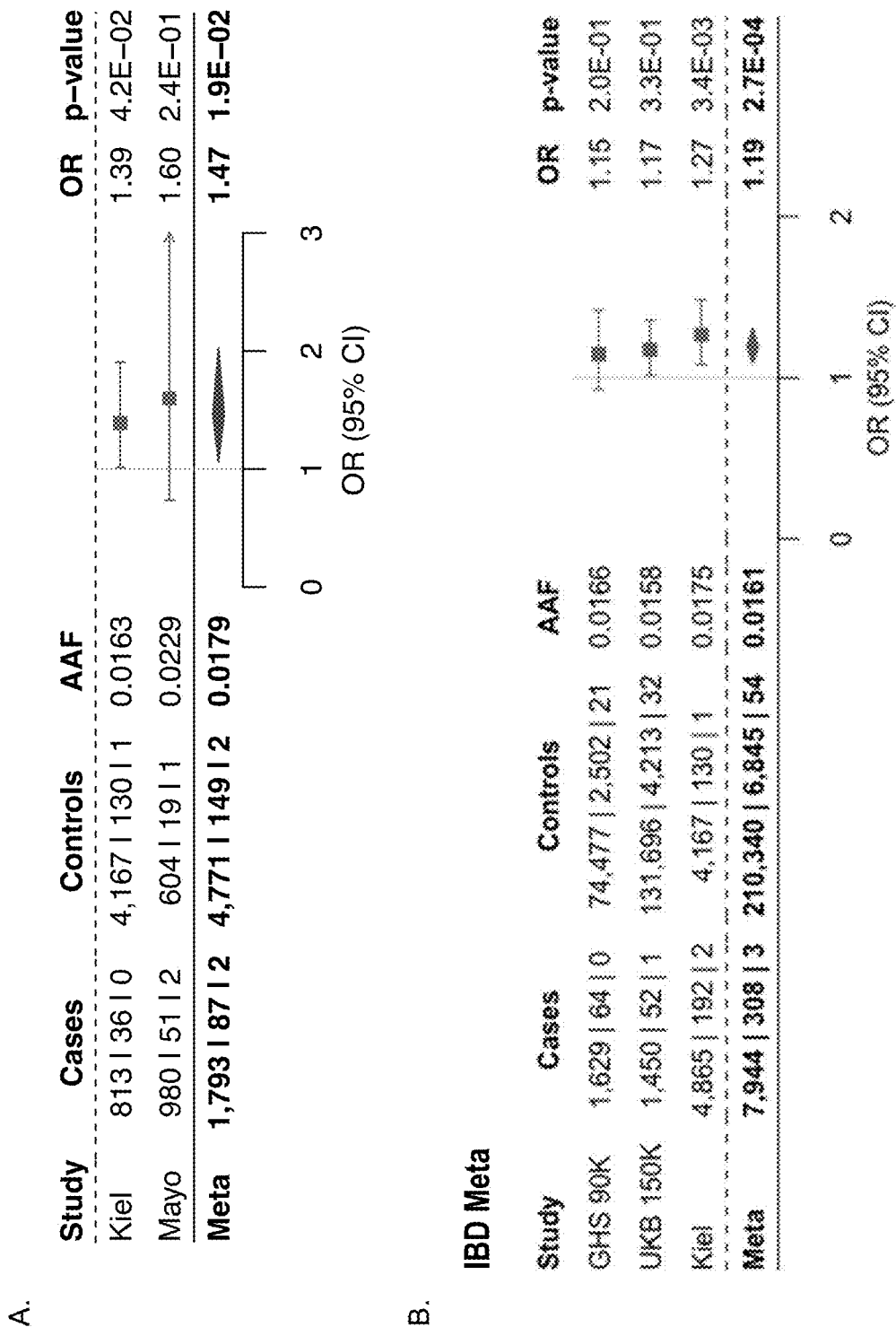
FIG. 3 shows results of meta-analysis of association of MST1 Arg651STOP pLoF mutant with PSC (panel A) and IBD (panel B).

A novel MST1 pLoF mutation (3:49684379:G:A generating a Stop gain; c.1951C>T; p.Arg651*) associating with a larger effect on PSC and IBD disease risk has been identified (Table 5 and FIG. 3), confirming that LoF of MST1 increased disease risk. This effect was greater than that of the MST1 missense mutation.

TABLE 5

| Cohort | Case RR:RA:AA | Control RR:RA:AA | OR (95% CI) | p-value | AAF |
|---|---|---|---|---|---|
| PSC Meta | 1793:87:2 | 4771:149:2 | 1.47 (1.06, 2.04) | 1.90E−2 | 0.018 |
| IBD Meta | 11617:447:4 | 207211:6726:53 | 1.19 (1.09, 1.31) | 2.7E−4 | 0.016 |

Figure 9:
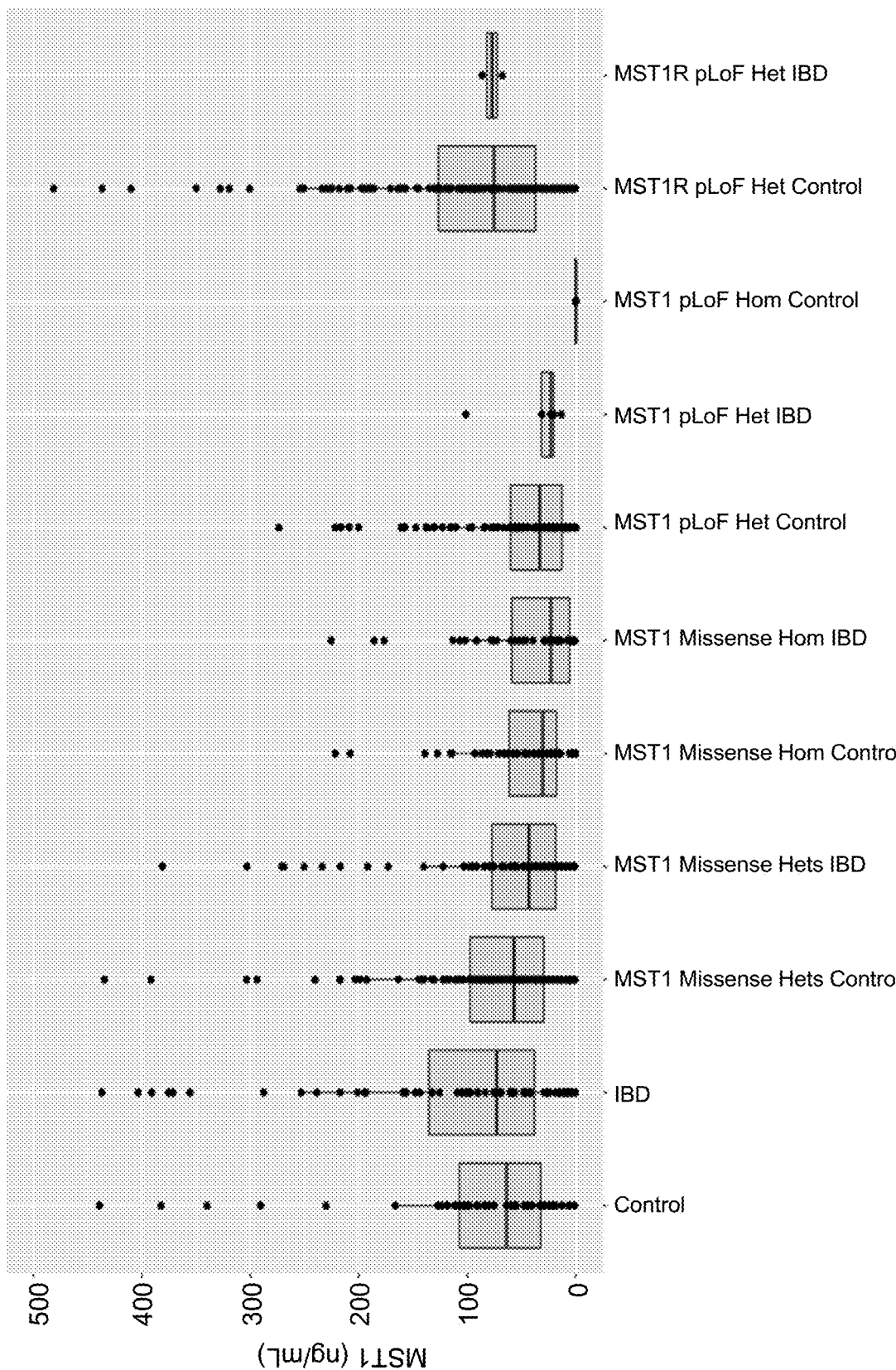
FIG. 9 shows serum levels of WT and variant MST1 and MST1R in patients with IBD.

Serum levels of MST1 were measured in MST1 variant carriers and controls. Serum was obtained from heterozygous and homozygous carriers of MST1 p.R703C, heterozygous and homozygous MST1 p.651*, and from reference carriers (who carried neither MST1 p.R703C or MST1 p.651* variants). Circulating serum MST1 levels were measured using a Luminex assay. The serum levels of carriers of variant MST1 proteins were analyzed. The results show that both MST1 p.R703C missense carriers and novel p.651* pLoF variant carriers have significantly decreased levels of MST1 in serum relative to control reference carriers (FIG. 9). The assay that was used is disclosed at the world wide web at "rndsystems.com/products/human-magnetic-luminex-assay_lxsahm".

Figure 4:
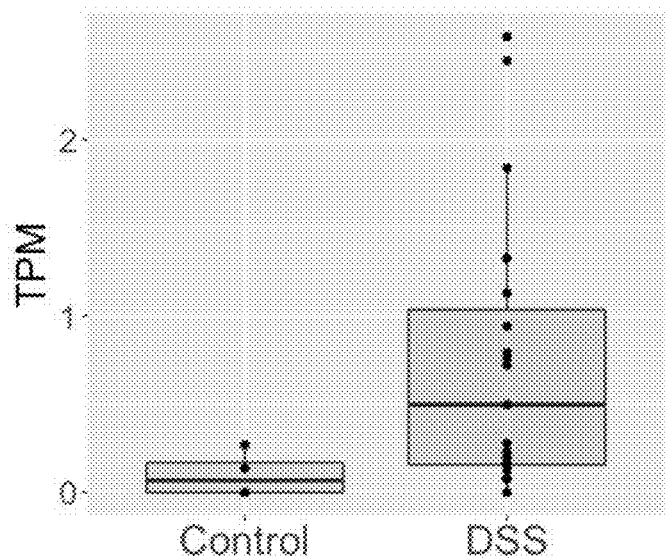
FIG. 4 shows MST1 RNA expression (panel A) and MST1R RNA (panel B) in control and DSS-induced model of colitis mice.
Figure 4:
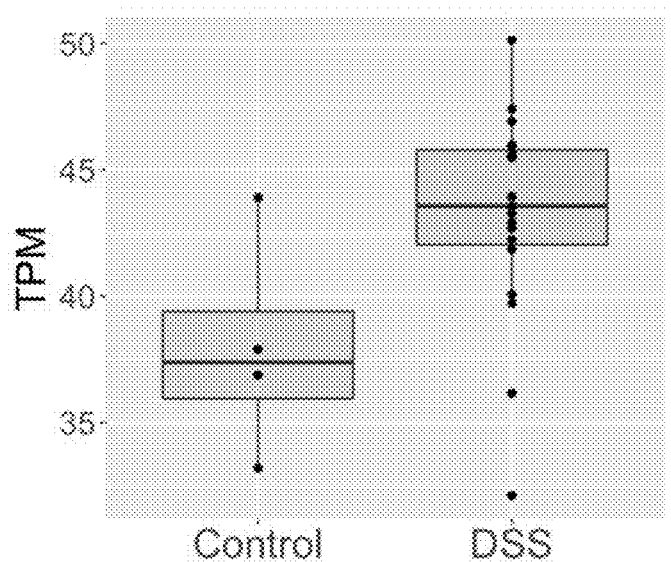
Figure 5:
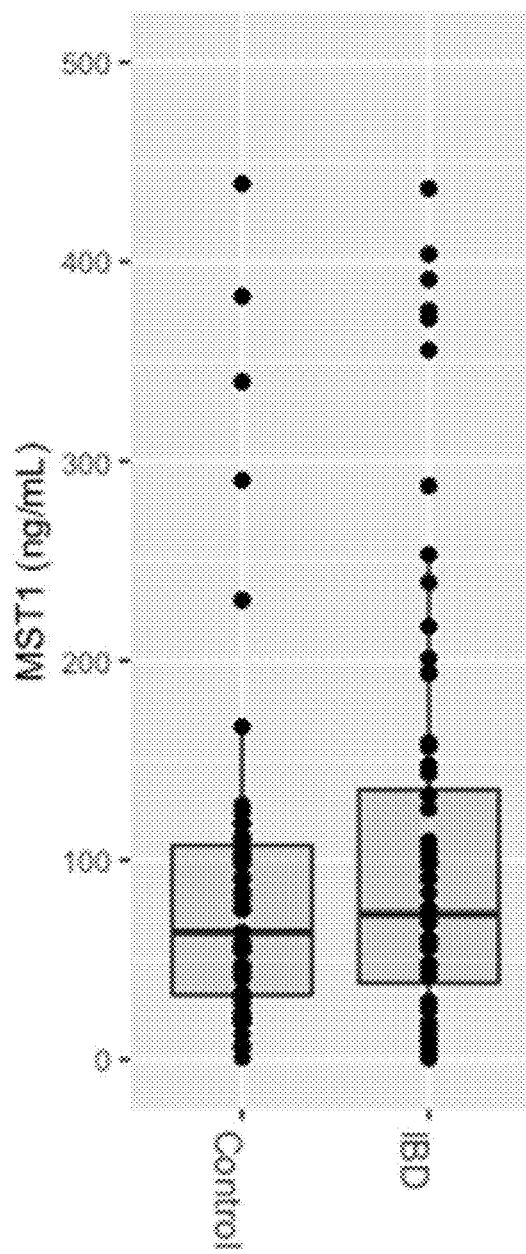
FIG. 5 shows MST1 expression in serum of control and IBD human patients.
Figure 6:
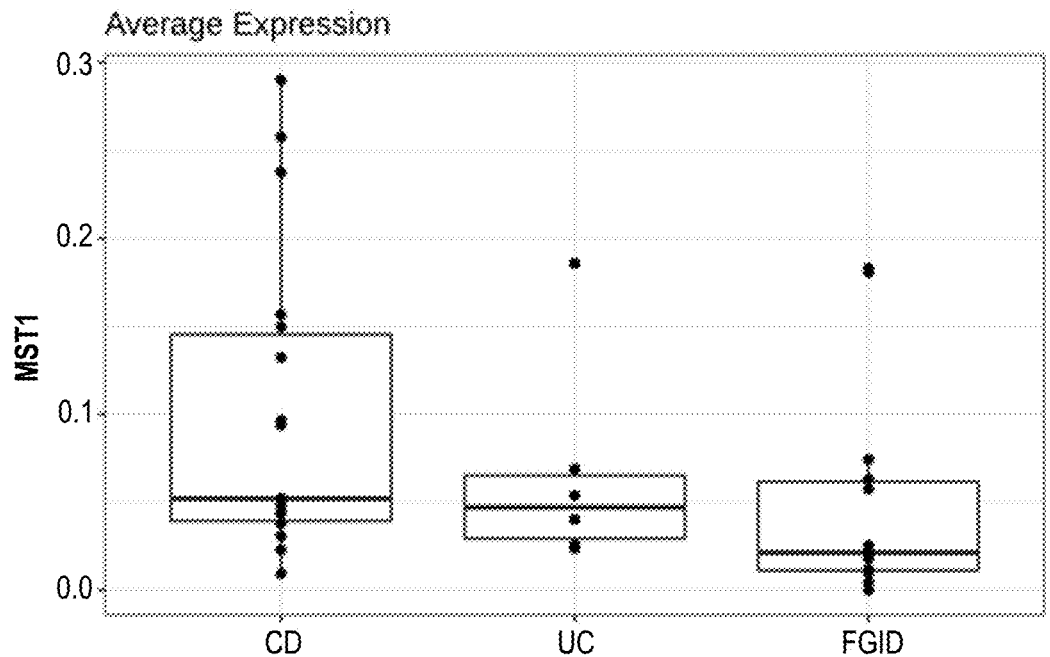
FIG. 6 shows MST1 expression (panel A) and MST1R expression (panel B) in intestinal epithelial cells obtained from healthy controls and human patients having UC or a functional gastrointestinal disorder (FGID).
Figure 6:
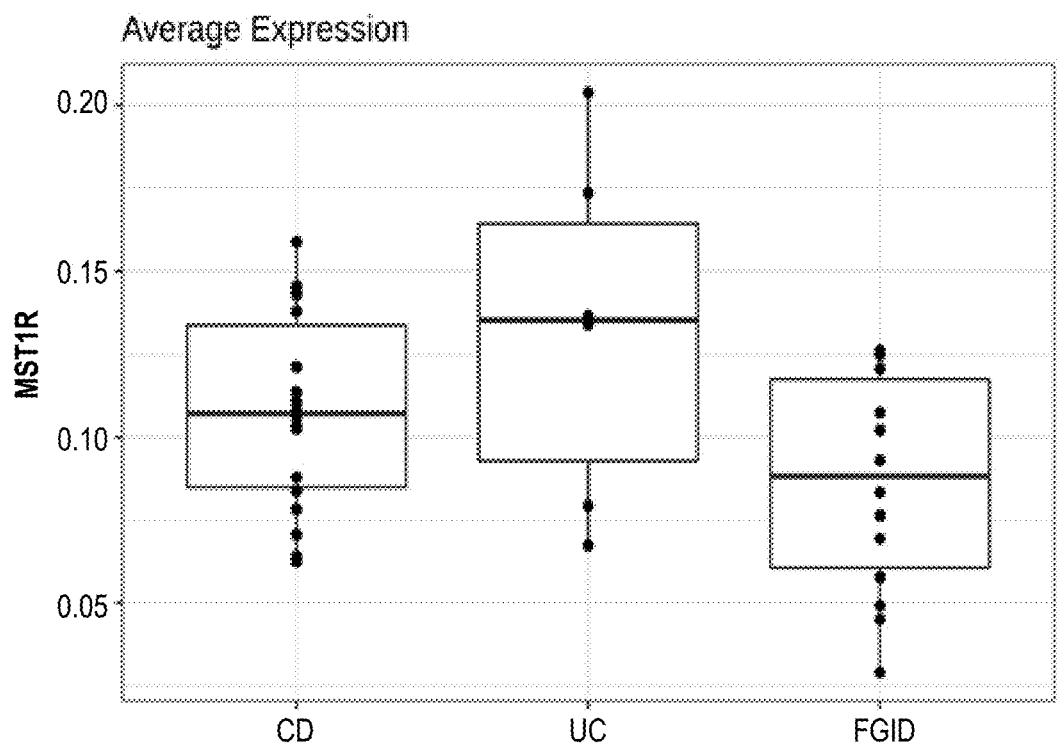
Figure 7:
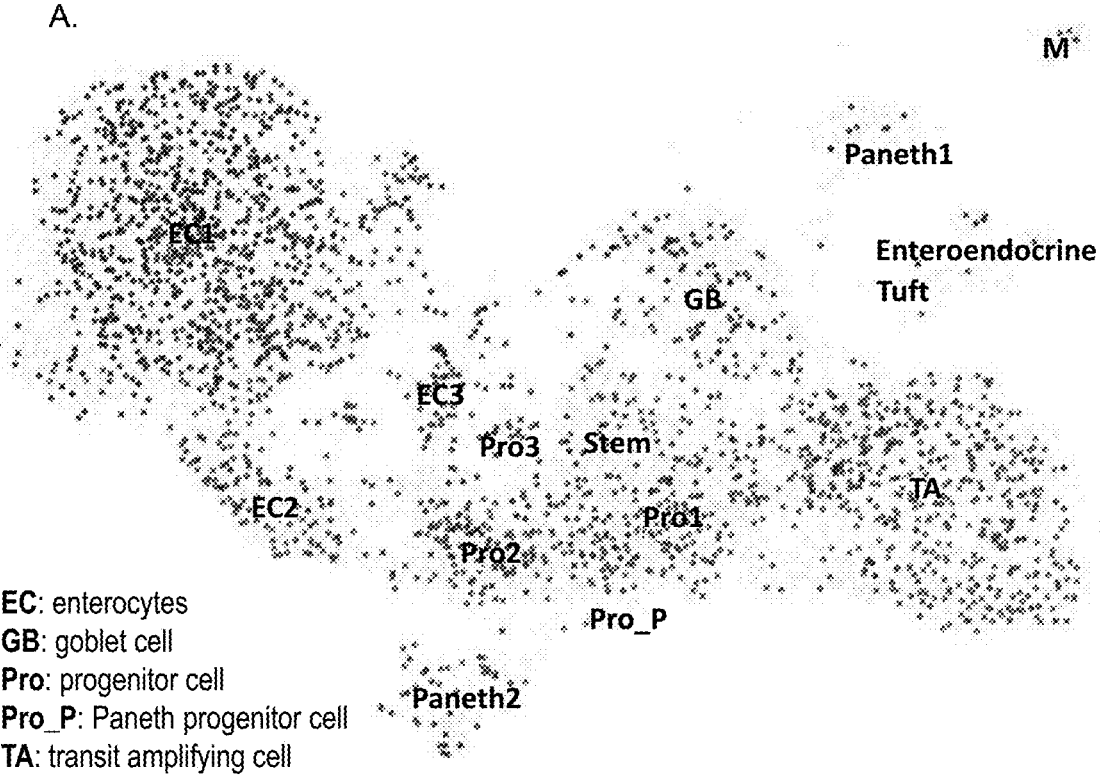
FIG. 7 shows results from single cell RNA sequencing in an IBD population (ulcerative colitis, Crohn's disease and functional gastrointestinal disorders) showing MST1R expression in epithelial cells (panel A) and intestinal immune cells (panel B) and MST1 expression in epithelial cells (panel C) and intestinal immune cells (panel D).
Figure 7:
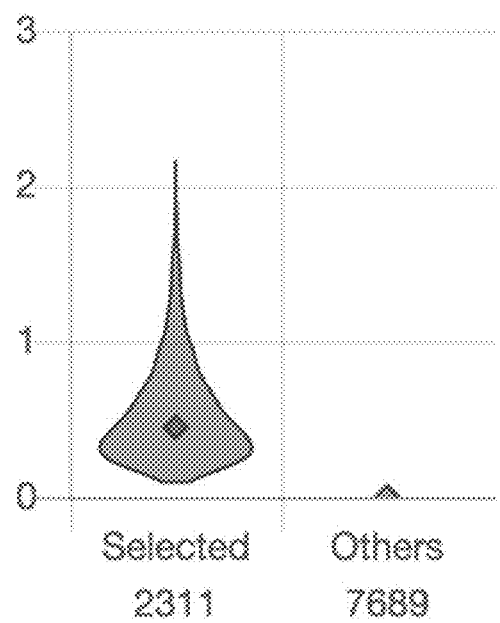
Figure 7:
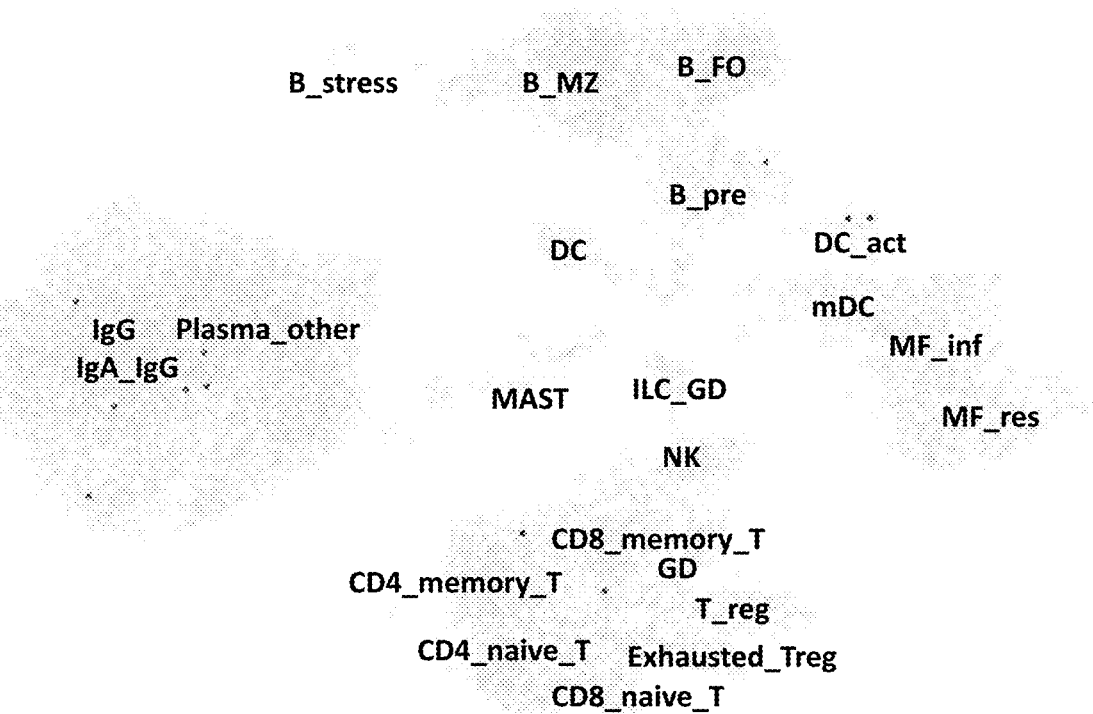
Figure 7:
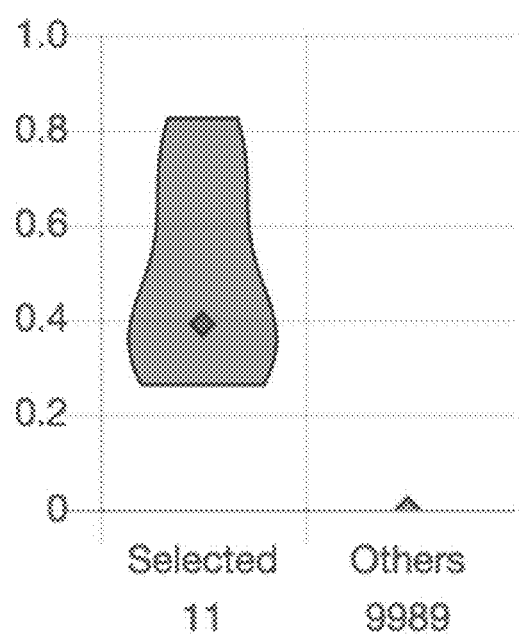
Figure 7:
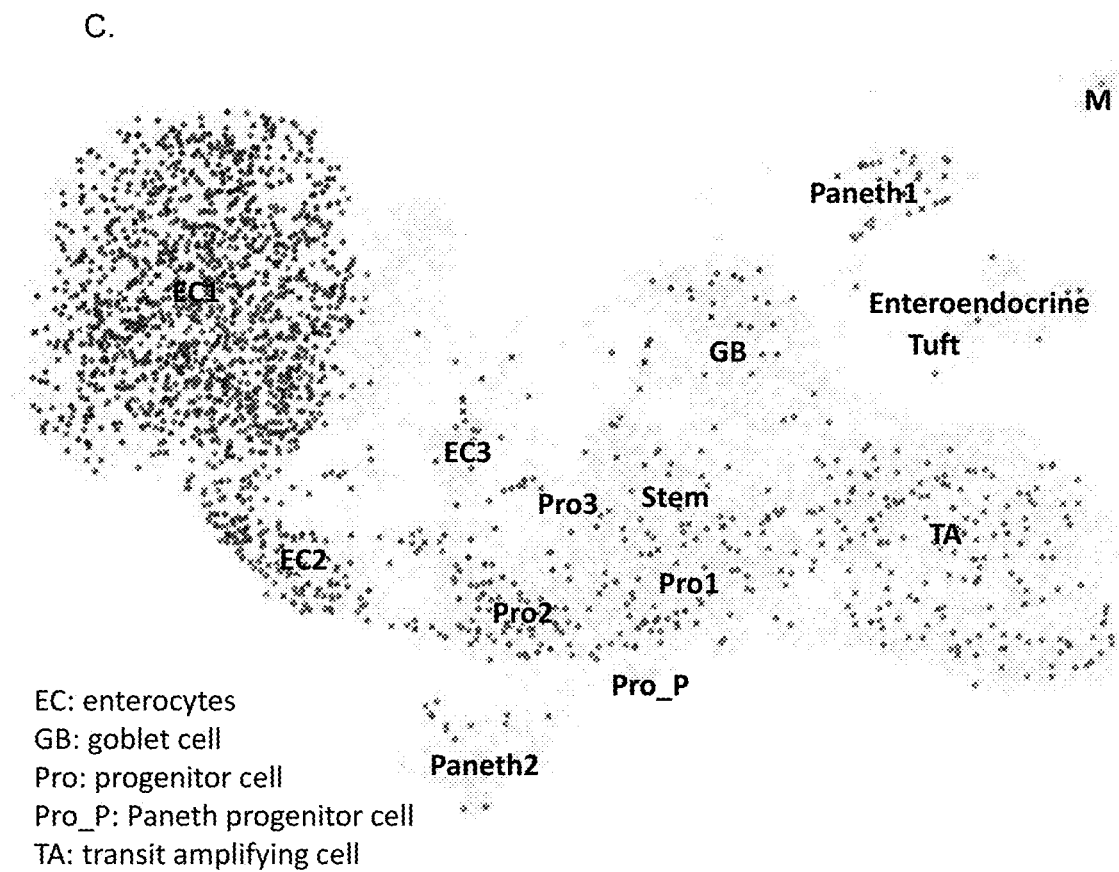
Figure 7:
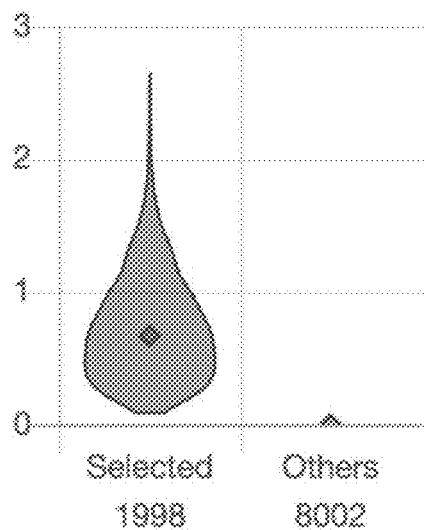
Figure 7:
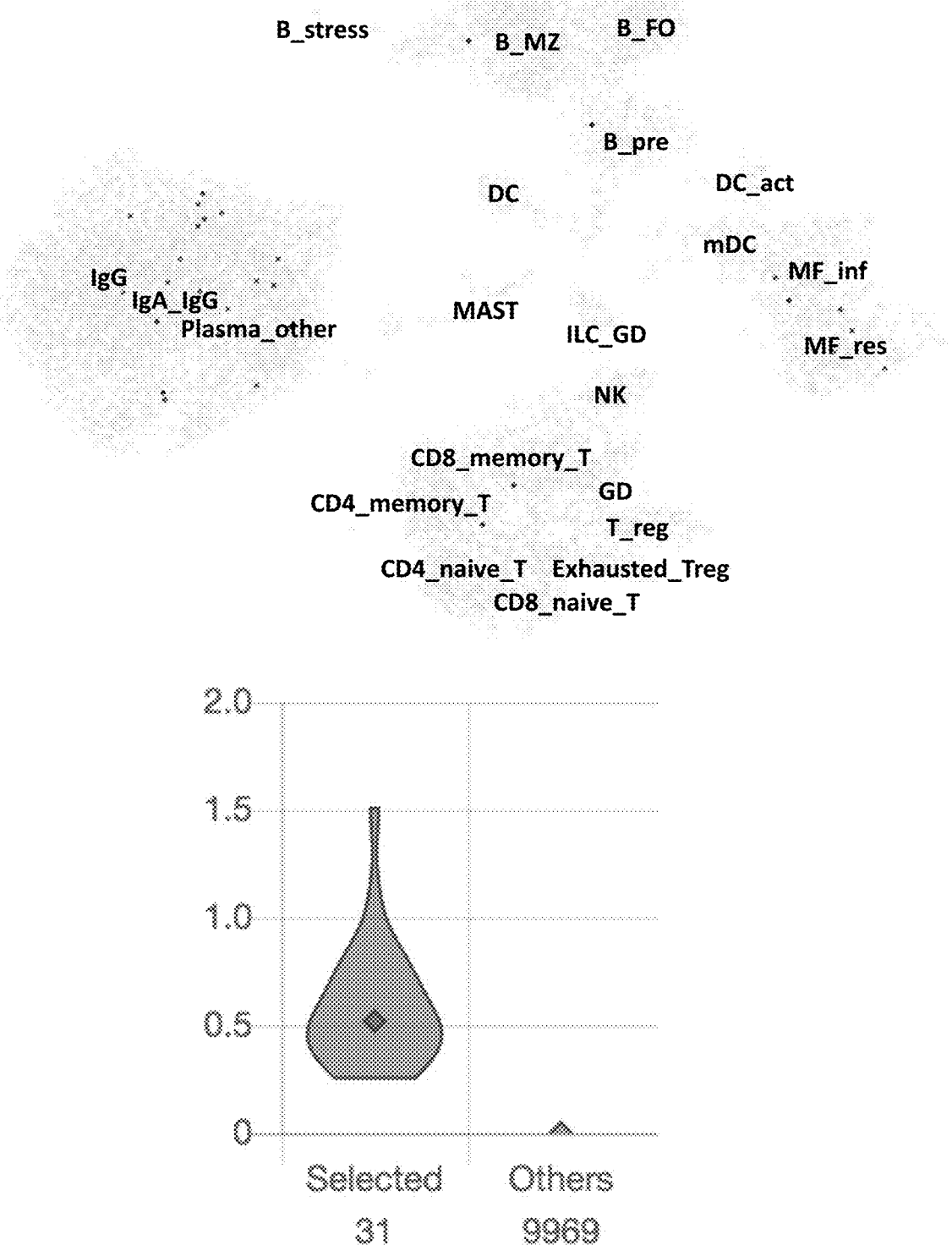

Example 4: Gastrointestinal Disorders Result in Changes of MST1 and MST1R Expression in Mice and in Human Patients The levels of MST1 and MST1R mRNA were examined in mice that have been treated with DSS in order to induce colitis. Bulk RNAseq assays revealed that both MST1 and MST1R expression increase in mouse models of colitis (FIG. 4). MST1 serum levels were assessed in human IBD patients as compared with healthy controls (FIG. 5). Serum was obtained from IBD patients and healthy controls (who did not carry MST1 p.R703C, MST1 p.651*, or MST1R pLOF variants), and MST1 was measured using a Luminex cytokine assay (as above). Analysis of these samples show an increase in MST1 serum concentration between IBD patients compared to healthy controls. MST1 and MST1R also increased in Crohn's disease, ulcerative colitis, and functional gastrointestinal disorder (FGID) patients (FIG. 6). Single cell RNA sequencing analysis was performed on intestinal biopsies of IBD patients with either Crohn's disease (CD), ulcerative colitis (UC), or patients with FGID as controls. Both MST1 and MST1R showed higher expression in small intestine epithelial cells of a human CD patient than in intestine lamina propria cells of a human FGID patient (FIG. 7).

In contrast to the increased wild type MST1/MST1R levels observed in IBD patients, the IBD patients carrying variant MST1 or MST1R showed decreased serum MST1 levels (FIG. 9). There was no difference between IBD and control levels among the variant carriers.

Example 5: Expression of Variant MST1R Constructs

Figure 11:
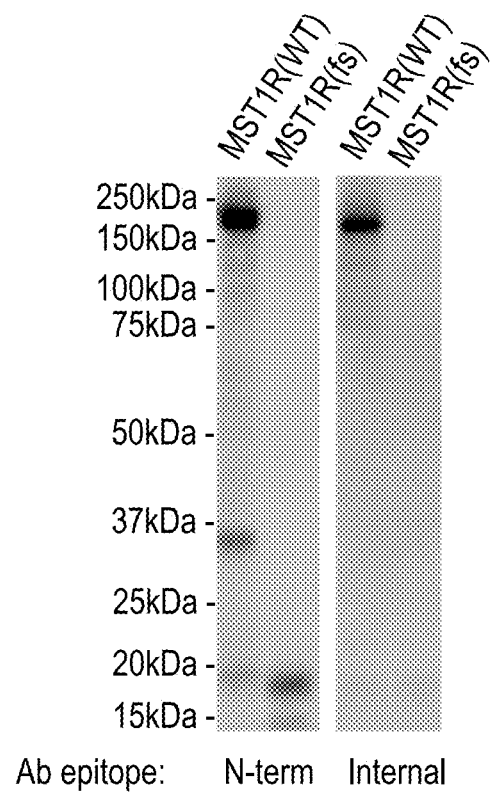
FIG. 11 shows expression of a truncated MST1R protein resulting from the G116fs mutation.

To ascertain whether an ATG codon encoding methionine at the position 464 of MST1R protein could be used as a translation start codon, expression of an MST1R cDNA construct carrying a G116fs mutation was examined. Western blot analysis of a HEK cell line transduced with a cDNA encoding either a full-length, wildtype MST1R or MST1R G116fs showed introduction of the frameshift in the cDNA of MST1R resulted in the translation of a short, truncated protein showing that downstream, in-frame ATG was not activated (FIG. 11).

Figure 12:
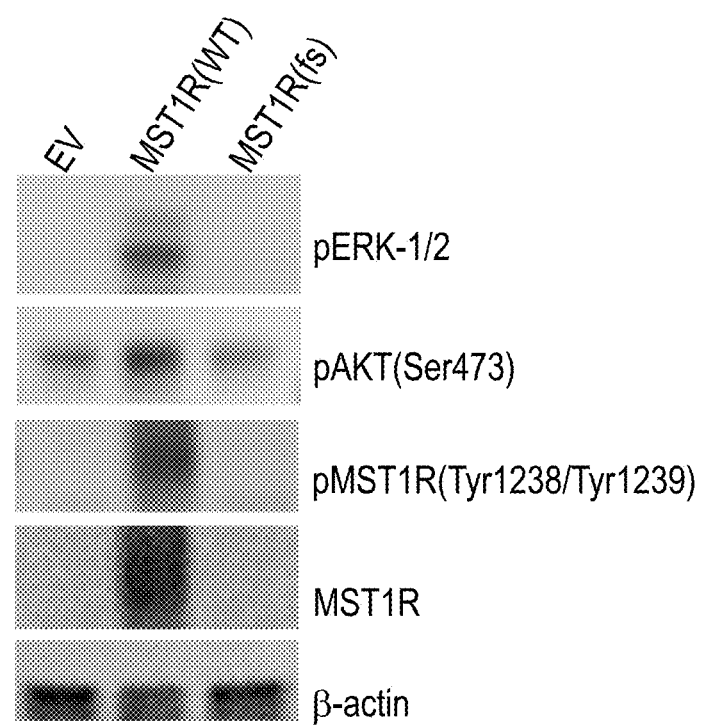
FIG. 12 shows that the MST1R G116fs mutant protein is not expressed in HEK cells and does not activate its downstream targets.

To analyze the properties of the truncated MST1R pLoF protein, HEK cells were transfected with constructs encoding either WT MST1R cDNA or a cDNA encoding an MST1R carrying the frameshift G116fs mutation. Western blot analysis of lysates generated from these cell lines show that while WT MST1R was robustly expressed and activated its downstream signaling targets, including phosphorylated ERK1/2 (pERK1/2), phosphorylated AKT (pAKT), and phosphorylated MST1R (pMST1R), no expression of mutant MST1R was detected and no activation of downstream targets was observed (FIG. 12), demonstrating that the MST1Rfs mutant is a true loss of function mutant.

Example 6: Expression of Variant MST1 Constructs

The results of Example 1 show that the aggregate of rare pLoFs/missense variants in MST1R associates with increased risk of IBD, suggesting loss of MST1R increases the risk of IBD. It may be that increased MST1 protein levels and/or increased MST1/MST1R signaling is protective and/or promotes tissue repair in IBD and PSC.

Figure 13:
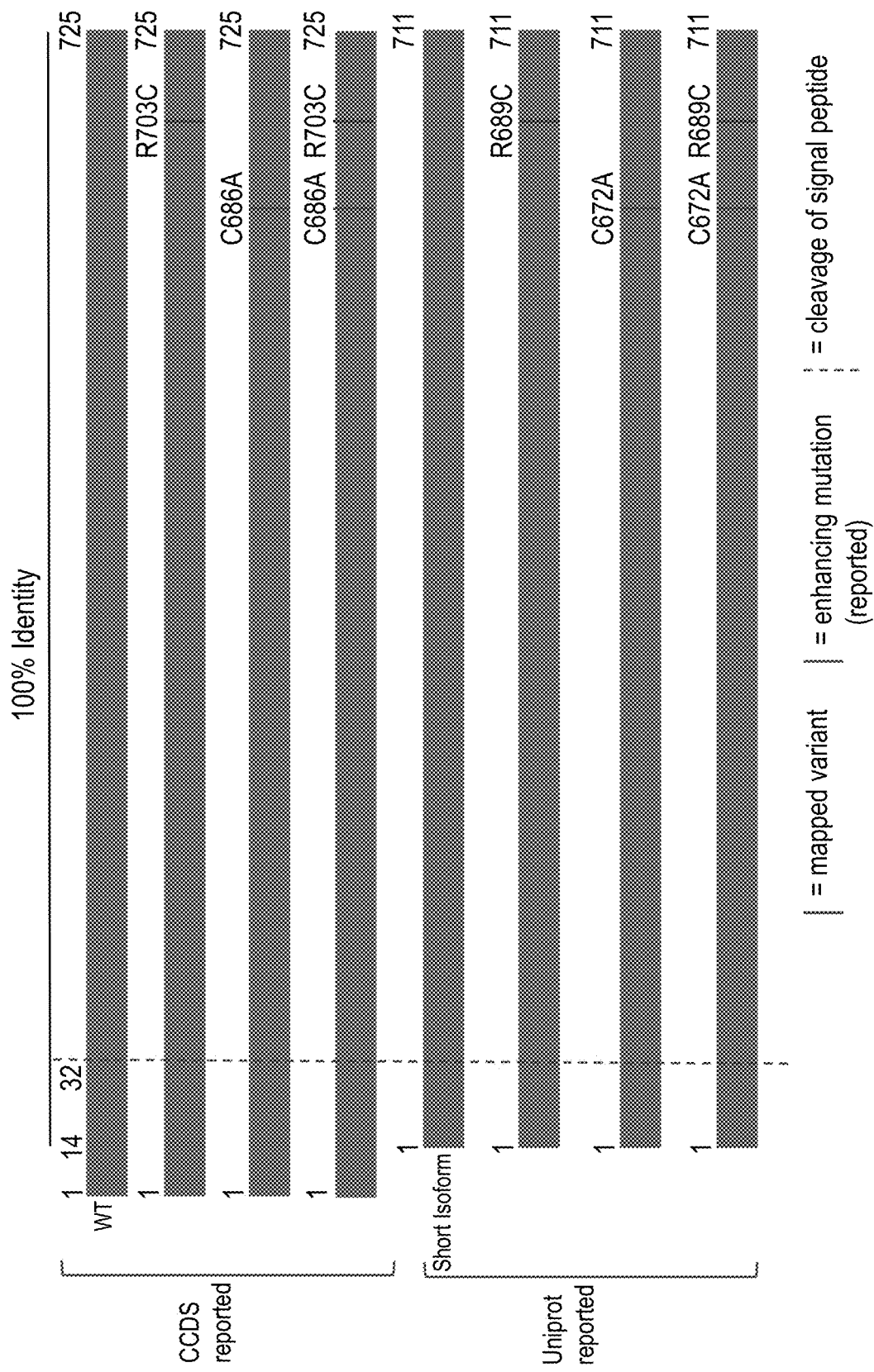
FIG. 13 shows a schematic representation of MST1 constructs used in transfection experiments.
Figure 14:
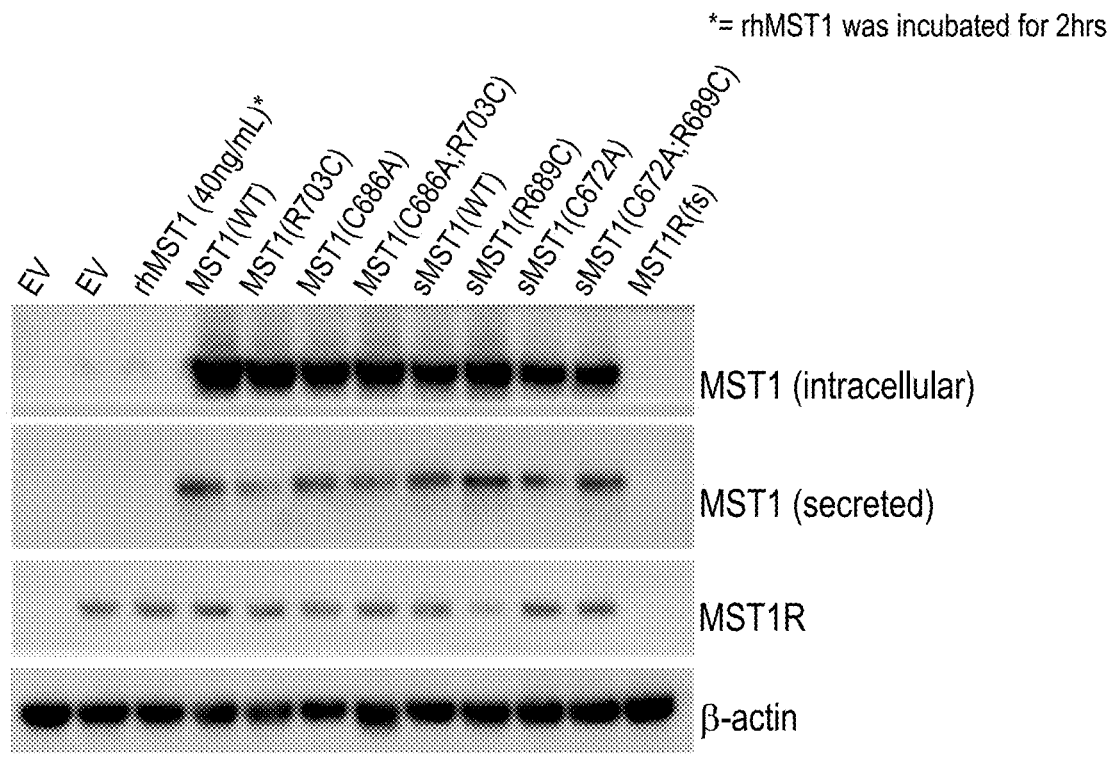
FIG. 14 shows expression and secretion of variant MST1 proteins.

To gauge the possibility of MST1 expression, several constructs encoding WT and variant MST1 cDNAs (FIG. 13) were transfected into HEK cells. Western blot analyses showed that all the variant MST1 constructs can be expressed and are secreted (FIG. 14).

Figure 8:
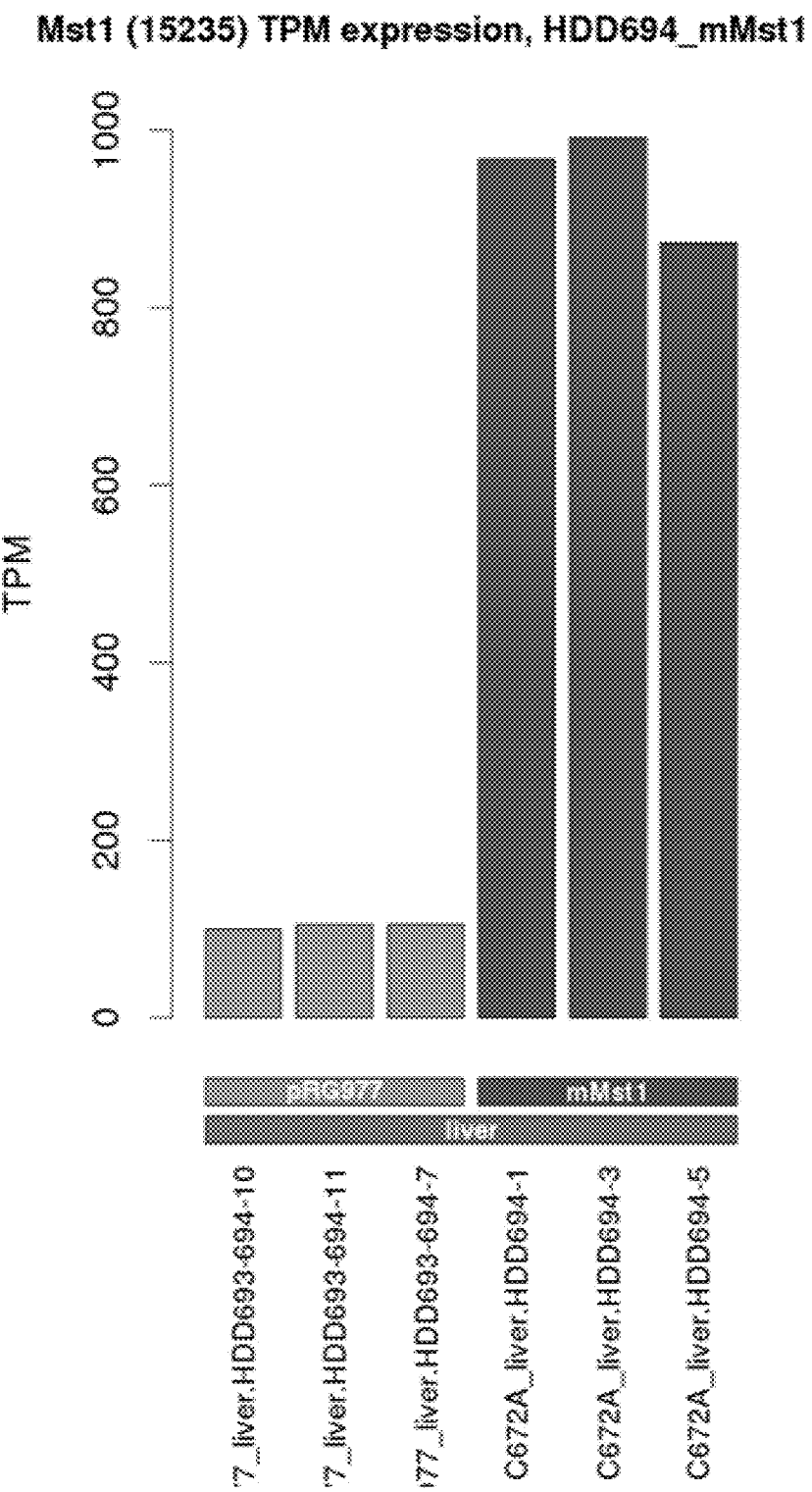
FIG. 8 shows consistent MST1-HDD expression in the livers of 3 control-HDD and 3 mMst1-HDD mice.
Figure 15:
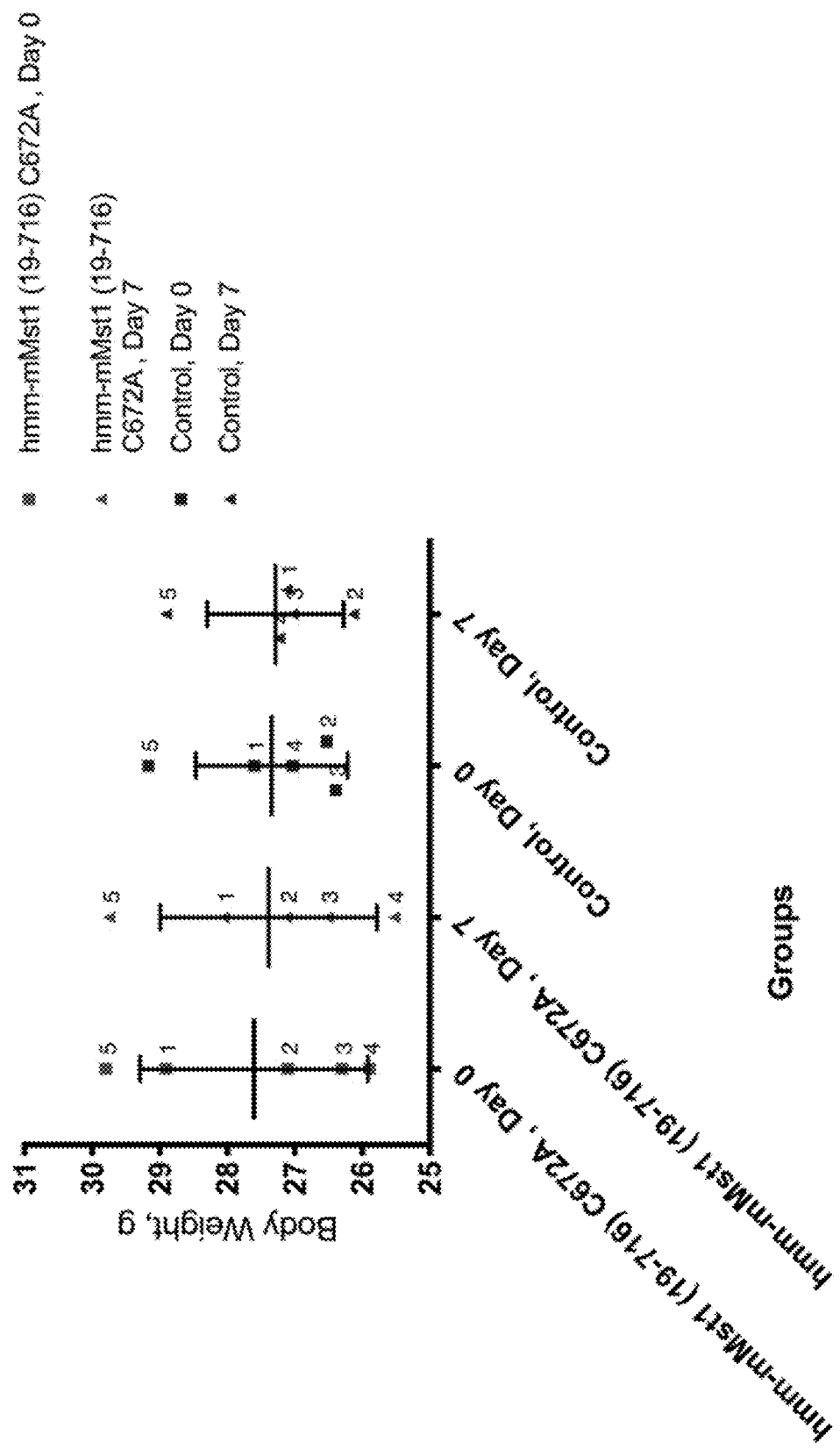
FIG. 15 shows body weight changes in mice expressing the C672A MDT1 mutant protein.
Figure 16:
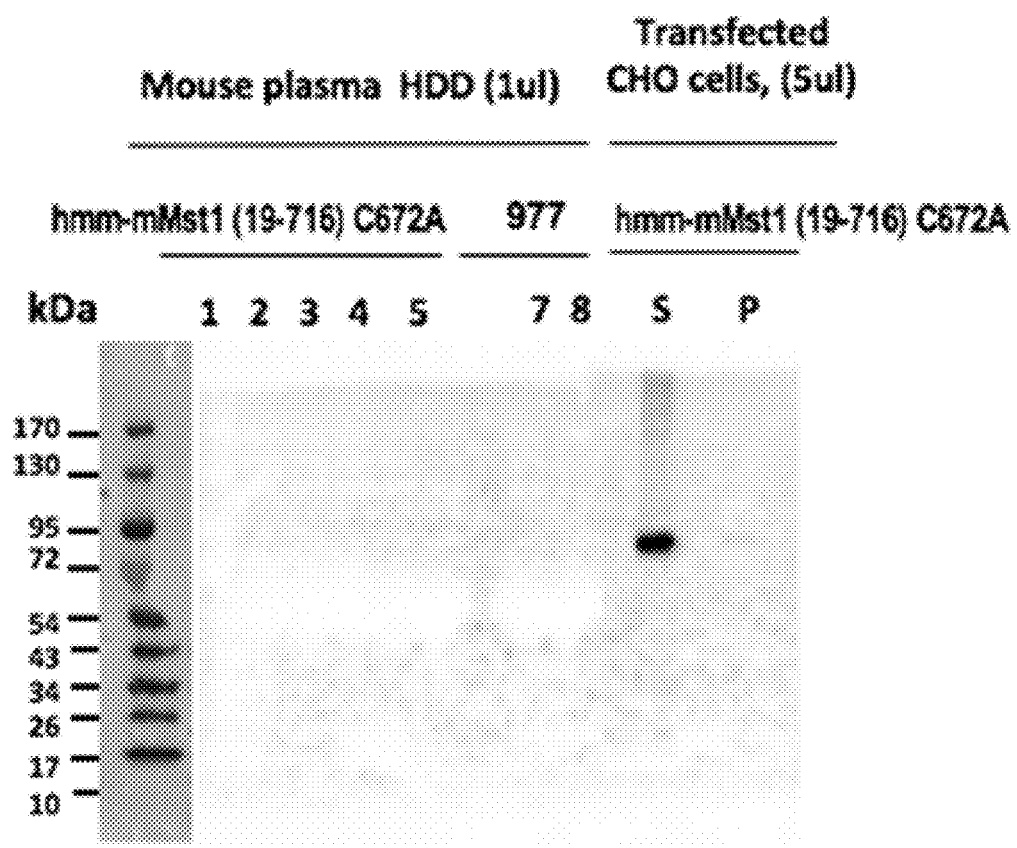
FIG. 16 shows analysis of plasma levels of the C672A MDT1 mutant protein.

Hydrodynamic delivery (HDD) was used to deliver WT MST1 cDNA packaged in an expression construct to mice, leading to overexpression of WT MST1. Mice injected with MST1 HDD construct survived the course of experiment, indicating that MST1 overexpression is not lethal (data not shown). Consistent expression of the control HDD construct was observed in the livers of 3 mice and consistent expression of the mMst1 construct was observed in the livers of 3 mMst1-HDD mice, indicating that these constructs were expressed and that expression was consistent within each group (FIG. 8). In addition, MST1 overexpression did not appear to affect mice body weight (FIG. 15). MST1 plasma levels were below the detection level as shown in a Western blot (FIG. 16) for a protein tag that was included as part of the construct. The tag was likely cleaved and was not detected. The vector was detectable when expressed in a CHO cell line.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

---

What is claimed is:

1. A method of treating a patient having inflammatory bowel disease (IBD) or primary sclerosing cholangitis (PSC), the method comprising administering to the patient an agonist of the Macrophage Stimulating 1 (MST1)/Macrophage Stimulating 1 Receptor (MST1R) pathway, thereby treating the patient, wherein the agonist is an MST1 protein.

2. The method according to claim 1, wherein the MST1 protein is a recombinant MST1 protein.

3. The method according to claim 1, further comprising detecting the presence or absence of an MST1 and/or MST1R variant nucleic acid molecule or variant polypeptide associated with an increased risk of developing IBD and/or PSC in a biological sample from the patient.

4. The method according to claim 3, wherein the MST1 variant nucleic acid molecule associated with an increased risk of developing IBD and/or PSC encodes Arg703Cys or Arg651 STOP.

5. The method according to claim 3, wherein the MST1R variant nucleic acid molecule associated with an increased risk of developing IBD and/or PSC is 3:49903264:CG:C, 3:49903084:C:T, 3:49890026:G:T, 3:49902417:A:G, 3:49902560:A:T, and/or 3:49903387:G:T, or an mRNA molecule produced therefrom, or a cDNA molecule produced from the mRNA molecule.

6. The method according to claim 3, wherein detecting the presence or absence of the MST1 and/or MST1R variant nucleic acid molecule or variant polypeptide associated with an increased risk of developing IBD and/or PSC comprises:
determining whether the patient has an MST1 and/or MST1R variant genomic nucleic acid molecule associated with an increased risk of developing IBD and/or PSC, an MST1 and/or MST1R variant mRNA molecule associated with an increased risk of developing IBD and/or PSC, an MST1 and/or MST1R variant cDNA molecule produced from the mRNA molecule, and/or an MST1 and/or MST1R variant polypeptide associated with an increased risk of developing IBD and/or PSC, by:
obtaining or having obtained a biological sample from the patient; and
performing or having performed an assay on the biological sample to determine whether the patient has an MST1 and/or MST1R variant nucleic acid molecule or variant polypeptide associated with an increased risk of developing IBD and/or PSC.

7. The method according to claim 6, further comprising determining the patient's aggregate burden of having: MST1 and/or MST1R variant genomic nucleic acid molecules associated with an increased risk of developing IBD and/or PSC, MST1 and/or MST1R variant mRNA molecules associated with an increased risk of developing IBD and/or PSC, MST1 and/or MST1R variant cDNA molecules produced from the mRNA molecules, and/or MST1 and/or MST1R variant polypeptides associated with an increased risk of developing IBD and/or PSC.

8. The method according to claim 6, wherein the assay is a genotyping assay for nucleic acid molecules.

9. The method according to claim 6, wherein the assay is an immunoassay for polypeptides.

10. The method according to claim 3, wherein the detecting step, determining step, or assay is carried out in vitro.

11. The method according to claim 3, wherein the detecting step, determining step, or assay comprises sequencing at least a portion of the nucleotide sequence of the MST1 and/or MST1R nucleic acid molecule in the biological sample, wherein the sequenced portion comprises a position corresponding to a predicted loss-of-function variant position, wherein when a variant nucleotide at the predicted loss-of-function variant position is detected, the MST1 and/or MST1R nucleic acid molecule in the biological sample is an MST1 and/or MST1R predicted loss-of-function variant nucleic acid molecule.

12. The method according to claim 11, wherein the detecting step, determining step, or assay comprises:
a) contacting the biological sample with a primer hybridizing to a portion of the nucleotide sequence of the MST1 and/or MST1R nucleic acid molecule that is proximate to a predicted loss-of-function variant position;
b) extending the primer at least through the predicted loss-of-function variant position; and
c) determining whether the extension product of the primer comprises a variant nucleotide at the predicted loss-of-function variant position.

13. The method according to claim 11, wherein the detecting step, determining step, or assay comprises sequencing the entire nucleic acid molecule.

14. The method according to claim 3, wherein the detecting step, determining step, or assay comprises sequencing at least a portion of the nucleotide sequence of the MST1 and/or MST1R nucleic acid molecule in the biological sample, wherein the sequenced portion comprises a position corresponding to a missense variant position, wherein when a variant nucleotide at the missense variant position is detected, the MST1 and/or MST1R nucleic acid molecule in the biological sample is an MST1 and/or MST1R missense variant nucleic acid molecule.

15. The method according to claim 14, wherein the detecting step, determining step, or assay comprises:
a) contacting the biological sample with a primer hybridizing to a portion of the nucleotide sequence of the MST1 and/or MST1R nucleic acid molecule that is proximate to a missense variant position;
b) extending the primer at least through the missense variant position; and
c) determining whether the extension product of the primer comprises a variant nucleotide at the missense variant position.

16. The method according to claim 14, wherein the detecting step, determining step, or assay comprises sequencing the entire nucleic acid molecule.

17. The method according to claim 3, wherein the detecting step, determining step, or assay comprises:
a) amplifying at least a portion of the MST1 and/or MST1R nucleic acid molecule, wherein the portion comprises a predicted loss-of-function variant position;
b) labeling the amplified nucleic acid molecule with a detectable label;
c) contacting the labeled nucleic acid molecule with a support comprising an alteration-specific probe, wherein the alteration-specific probe comprises a nucleotide sequence which hybridizes under stringent conditions to the predicted loss-of-function variant position; and
d) detecting the detectable label.

18. The method according to claim 17, wherein the nucleic acid molecule in the sample is mRNA and the mRNA is reverse-transcribed into a cDNA prior to the amplifying step.

19. The method according to claim 17, wherein the detecting step, determining step, or assay comprises:
contacting the nucleic acid molecule in the biological sample with an alteration-specific probe comprising a detectable label, wherein the alteration-specific probe comprises a nucleotide sequence which hybridizes under stringent conditions to a predicted loss-of-function variant position; and detecting the detectable label.

20. The method according to claim 3, wherein the detecting step, determining step, or assay comprises:
   a) amplifying at least a portion of the MST1 and/or MST1R nucleic acid molecule, wherein the portion comprises a missense variant position;
   b) labeling the amplified nucleic acid molecule with a detectable label;
   c) contacting the labeled nucleic acid molecule with a support comprising an alteration-specific probe, wherein the alteration-specific probe comprises a nucleotide sequence which hybridizes under stringent conditions to the missense variant position; and
   d) detecting the detectable label.

21. The method according to claim 20, wherein the nucleic acid molecule in the sample is mRNA and the mRNA is reverse-transcribed into a cDNA prior to the amplifying step.

22. The method according to claim 20, wherein the detecting step, determining step, or assay comprises:
   contacting the nucleic acid molecule in the biological sample with an alteration-specific probe comprising a detectable label, wherein the alteration-specific probe comprises a nucleotide sequence which hybridizes under stringent conditions to a missense variant position; and
   detecting the detectable label.

23. The method according to claim 3, wherein the MST1 variant nucleic acid molecule associated with an increased risk of developing IBD and/or PSC encodes Arg651STOP.

* * * * *